(12) United States Patent
Gozes et al.

(10) Patent No.: US 10,118,943 B2
(45) Date of Patent: Nov. 6, 2018

(54) COMPOUNDS AND METHODS FOR INHIBITING CELL DEATH

(71) Applicant: Ramot at Tel-Aviv University Ltd., Tel Aviv (IL)

(72) Inventors: Illana Gozes, Ramat-Hasharon (IL); Saar Oz, Ramat-Hasharon (IL); Jacqueline Woang Cheing Tiong, Vancouver (CA)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 202 days.

(21) Appl. No.: 14/401,504

(22) PCT Filed: Mar. 12, 2013

(86) PCT No.: PCT/IB2013/051957
§ 371 (c)(1),
(2) Date: Nov. 14, 2014

(87) PCT Pub. No.: WO2013/171595
PCT Pub. Date: Nov. 21, 2013

(65) Prior Publication Data
US 2015/0141345 A1 May 21, 2015

Related U.S. Application Data

(60) Provisional application No. 61/647,661, filed on May 16, 2012.

(51) Int. Cl.
| | |
|---|---|
| C07K 5/10 | (2006.01) |
| C07K 14/47 | (2006.01) |
| C07K 7/06 | (2006.01) |
| G01N 33/569 | (2006.01) |
| A61K 38/00 | (2006.01) |
| C07K 5/103 | (2006.01) |

(52) U.S. Cl.
CPC .............. *C07K 5/10* (2013.01); *C07K 5/1013* (2013.01); *C07K 7/06* (2013.01); *C07K 14/4711* (2013.01); *G01N 33/56966* (2013.01); *A61K 38/00* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 6,271,011 B1* | 8/2001 | Lee | ...................... | C12N 9/2462 435/200 |
| 8,017,578 B2 | 9/2011 | Brenneman et al. | | |
| 8,324,166 B2* | 12/2012 | Gozes | ................... | A61K 38/08 514/17.7 |
| 2003/0109690 A1 | 6/2003 | Ruben et al. | | |
| 2009/0087472 A1* | 4/2009 | Murphy | ................. | A61B 17/80 424/423 |
| 2010/0216723 A1* | 8/2010 | Gozes | .................... | A61K 38/08 514/13.7 |
| 2013/0330335 A1* | 12/2013 | Bremel | .................... | G06F 19/18 424/134.1 |

FOREIGN PATENT DOCUMENTS

| | | |
|---|---|---|
| WO | 00/61624 A1 | 10/2000 |
| WO | 01/12654 A2 | 2/2001 |
| WO | 2013/040142 A2 | 3/2013 |
| WO | 2013/171591 A2 | 11/2013 |

OTHER PUBLICATIONS

Honnappa et al., Cell, 2009; 138: 366-376.*
Yang et al., Molecular & Cellular Proteomics, 2009; 8: 571-583.*
Archived website downloaded from: web.archive.org/web/20080204224458/http://www.genscri pt.com/peptide_modification.html; 2 pages total; Feb. 4, 2008.*
Sadowski et al., Am J Pathol, 2004; 165: 937-948.*
Barth, et al., "Role of Adenomatous Polyposis Coli (APC) and Microtubules in Directional Cell Migration and Neuronal Polarization," Semin Cell Dev Biol, vol. 19(3), pp. 245-251 (2008).
Brenneman, et al., "A Femtomolar-acting Neuroprotective Peptide," J Clin Invest, vol. 97(10), pp. 2299-2307 (1996).
Brenneman, et al., "Protective Peptides That Are Orally Active and Mechanistically Nonchiral," J Pharmacol Exp Ther, vol. 309(3), pp. 1190-1197 (2004).
De Groot, et al., "Molecular Insights into Mammalian End-binding Protein Heterodimerization," J Biol Chem, vol. 285(8), pp. 5802-5814 (2010).
Divinski, et al., "A Femtomolar Acting Octapeptide Interacts with Tubulin and Protects Astrocytes against Zinc Intoxication," J Biol Chem, vol. 279(27), pp. 28531-28538 (2004).
Divinski, et al., "Peptide neuroprotection through specific interaction with brain tubulin," J Neurochem, vol. 98(3), pp. 973-984 (2006).
Fong, et al., "Interaction of CDK5RAP2 with EB1 to Track Growing Microtubule Tips and to Regulate Microtubule Dynamics," Mol Biol Cell, vol. 20(16), pp. 3660-3670 (2009).
Gozes, et al., "Neurotrophic Effects of the Peptide NAP: A Novel Neuroprotective Drug Candidate," Curr Alzheimer Res, vol. 3(3),pp. 197-199 (2006).
Gozes, et al., "Neuroprotective strategy for Alzheimer disease: Intranasal administration of a fatty neuropeptide," Proc Natl Acad Sci USA, vol. 93(1), pp. 427-432 (1996).
Gozes, et al., "NAP Accelerates the Performance of Normal Rats in the Water Maze," J Mol Neurosci, vol. 19(1-2), pp. 167-170 (2002).

(Continued)

*Primary Examiner* — Christina M Borgeest
(74) *Attorney, Agent, or Firm* — Kilpatrick Townsend & Stockton LLP

(57) ABSTRACT

This invention provides novel compounds and methods for promoting cell survival and/or plasticity, especially in neuronal cells, by targeting the microtubule End Binding (EB) proteins and other associated proteins (e.g., drebrin). Methods for identifying potential modulators of cell death/plasticity are also described.

12 Claims, 20 Drawing Sheets

Specification includes a Sequence Listing.

(56) References Cited

OTHER PUBLICATIONS

Gozes, et al., "From Vasoactive Intestinal Peptide (VIP) Through Activity-Dependent Neuroprotective Protein (ADNP) to NAP: A View of Neuroprotection and Cell Division," J Mol Neurosci, vol. 20(3), pp. 315-322 (2003).

Grigoriev, et al., "STIM1 is a MT-Plus-End-Tracking Protein Involved in Remodeling of the ER," Curr Biol, vol. 18(3), pp. 177-182 (2008).

Holtser-Cochav, et al., "Tubulin is the Target Binding Site for NAP-Related Peptides: ADNF-9, D-NAP, and D-SAL," J Mol Neurosci, vol. 28(3), pp. 303-307 (2006).

Hoogenraad, et al., "Control of neuronal polarity and plasticity—a renaissance for microtubules?" Trends Cell Biol, vol. 19(12), pp. 669-676 (2009).

Hu, et al., "Activity-Dependent Dynamic Microtubule Invasion of Dendritic Spines," J Neurosci, vol. 28(49), pp. 13094-13105 (2008).

Huang, et al., "Modulation of neuronal protein trafficking and function by palmitoylation," Curr Opin Neurobiol, vol. 15(5), pp. 527-535 (2005).

Jang, et al., "DDA3 recruits microtubule depolymerase Kif2a to spindle poles and controls spindle dynamics and mitotic chromosome movement," J Cell Biol, vol. 181(2), pp. 255-267 (2008).

Jiang, et al., "TIP150 interacts with and targets MCAK at the microtubule plus ends," EMBO Rep, vol. 10(8), pp. 857-865 (2009).

Kumar, et al., "GSK3β phosphorylation modulates CLASP-microtubule association and lamella microtubule attachment," J Cell Biol, vol. 184(6), pp. 895-908 (2009).

Laketa, et al., "High-Content Microscopy Identifies New Neurite Outgrowth Regulators," Mol Biol Cell, vol. 18(1), pp. 242-252 (2007).

Maes, et al., "Neuron Navigator: A Human Gene Family with Homology to unc-53, a Cell Guidance Gene from *Caenorhabditis elegans*," Genomics, vol. 80(1), pp. 21-30 (2002).

Oz, et al., "The ADNP Derived Peptide, NAP Modulates the Tubulin Pool: Implication for Neurotrophic and Neuroprotective Activities," PLoS One, vol. 7(12), pp. 1-13 (2012).

Oz, et al., "The NAP motif of activity-dependent neuroprotective protein (ADNP) regulates dendritic spines through microtubule end binding proteins," Molecular Psychiatry, vol. 19, pp. 1115-1124 (2014).

Pascual, et al., "The peptide NAP promotes neuronal growth and differentiation through extracellular signal-regulated protein kinase and Akt pathways, and protects neurons co-cultured with astrocytes damaged by ethanol," J Neurochem, vol. 103(2), pp. 557-568 (2007).

Penzes, et al., "Not Just Actin? A Role for Dynamic Microtubules in Dendritic Spines," Neuron, vol. 61(1), pp. 3-5 (2009).

Shim, et al., "Drebrin, a dendritic spine protein, is manifold decreased in brains of patients with Alzheimer's disease and Down syndrome," Neurosci Lett, vol. 324(3), pp. 209-212 (2002).

Smith-Swintosky, et al., "Activity-Dependent Neurotrophic Factor-9 and NAP Promote Neurite Outgrowth in Rat Hippocampal and Cortical Cultures," J Mol Neurosci, vol. 25(3), pp. 225-238 (2005).

Tanenbaum, et al., "Regulation of localization and activity of the microtubule depolymerase MCAK," Bioarchitecture, vol. 1(2), pp. 80-87 (2011).

Wilkemeyer, et al., "Differential effects of ethanol antagonism and neuroprotection in peptide fragment NAPVSIPQ prevention of ethanol-induced developmental toxicity," Proc Natl Acad Sci USA, vol. 100(14), pp. 8543-8548 (2003).

Wu, et al., "Melanophilin and myosin Va track the microtubule plus end on EB1," J Cell Biol, vol. 171(2), pp. 201-207 (2005).

Gouveia, et al., "In Vitro Reconstitution of the Functional Interplay between MCAK and EB3 at Microtubule Plus Ends," *Current Biology*, vol. 20, pp. 1717-1722 (2010).

Gu, et al., "Microtubules in Dendritic Spine Development," *J Neurosci.*, vol. 28(46), pp. 12120-12124 (2008).

Honnappa, et al., "An EB1-Binding Motif Acts as a Microtubule Tip Localization Signal," *Cell*, vol. 138, pp. 366-376 (2009).

Jaworski, et al., "Dynamic Microtubules Regulate Dendritic Spine Morphology and Synaptic Plasticity," *Neuron*, vol. 61, pp. 85-100 (2009).

Mattie, et al., "Directed microtubule growth, +TIPs and kinesin-2 are required for uniform microtubule polarity in dendrites," *Curr. Biol.*, vol. 20(24), pp. 2169-2177 (2010).

International Search Report for International Application No. PCT/IB2013/051957, dated Jul. 17, 2013.

* cited by examiner

Figure 2

The EB1 binding motif was outlined by Honnappa *et al.* (*Cell* 138, 366, Jul 23, 2009) showing the conservation of the EB1 binding partners.

```
hsMACF2      THRFT FRACSRPSTAKPSKIPTPQRKSPASKLDKSSKR*-5493
hsAPC        YNFSPRKSSADSTSARPSQIPTPVNKNTKKRDSKTDSIE-2824
hsCLASP2     SSGVQRVINKSASAQKRSKIPRSQCCSREASPSRLSVAR-515
hsCLASP2     QGCSRRASPSRLSVARSSRIPRPSVSQGCSREASRESSR-339
hsSTIM1      DTPSPVQDSRALQASRNTRIPHLAGKKAVAEEDNGSTGE-663
hsMCAK       PLQENVTIQKQKRRSVNSKIPAPKESLRSRSTRMSTVSE-119
─────────────────────────────────────────────────────────
hsp140Cap    GSNETSSPVSRKPSASRTSIPVLTSPCARNSSISF*    -1183
hsDDA3       PRPQGAAAKSSSQLPIPSAIPRPASRMPLTSRSVPPGRG-302
mmMelan      LRAAGLLVKPSGKPRRKSGIPIFLPRVTEKLDRIPKTPP-515
```

Conservation of the SxIP Motif in Mammalian +TIPs
Sequence alignment of mammalian +TIPs containing basic and serine-rich sequence regions with the SxIP motifs highlighted in orange. Basic and acidic residues are highlighted in blue and red, respectively. Known serine phosphorylation sites in APC and MCAK are underlined and in bold. The dashed line separates proteins where SxIP motif-dependent microtubule tip tracking has been experimentally verified in this work (top sequences) from those that are predicted to be important (bottom sequences). The sequence of the 12-residue MACF2 construct (MACF12LZ), which is sufficient to track microtubule tips as a dimeric GFP-fusion in cells (Figure 2E), is indicated with a bar on top of the alignment. For sequence accession numbers, see Experimental Procedures. Species identifiers are: hs, *Homo sapiens*; mm, *Mus musculus*. The asterisks in MACF2 and p140Cap indicate the C termini of these proteins.

Figure 3

Comparison of the EB1 binding motif (SxIP)

*Figure shows multiple sequence alignment of MAPRE1/2/3 proteins from mouse, rat, and human.* colored rectangular indicate the binding cavity interacting residues.
MAPRE - Microtubule-associated protein, RP/EB family.

Saar Oz & Prof. Gozes

Figure 4
(a)
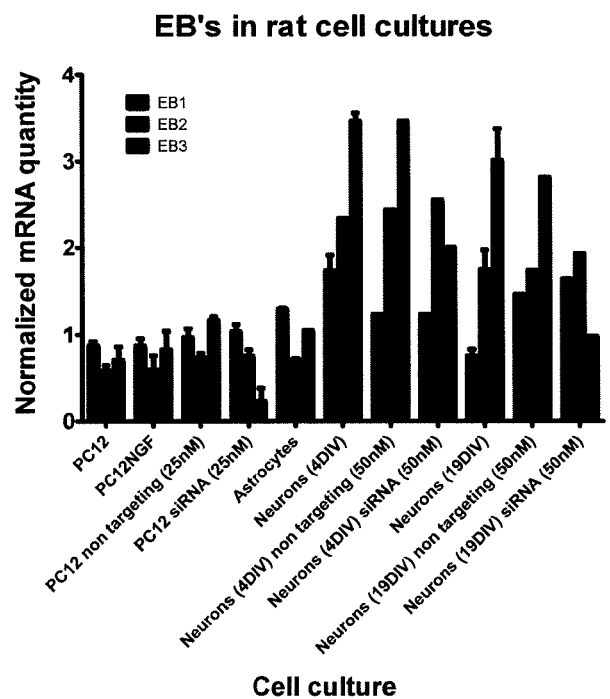
(b)
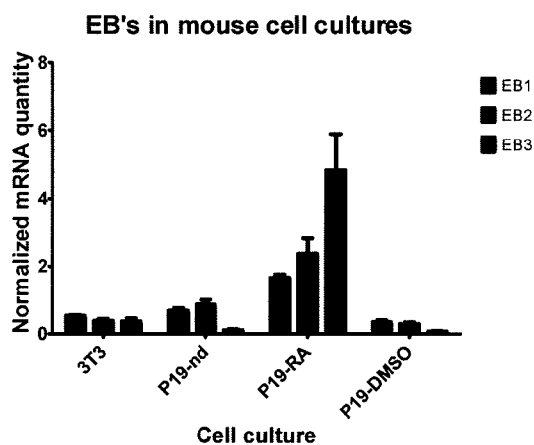

| Load | Load | Load | Load |
|---|---|---|---|
| (EB3+NAPVSIPQ) | (EB3+NAPVSKIPQ) | (EB3+NAPVAAAAQ) | (EB3+NAPVSAIPQ) |
| =10μl ~ 0.16μg | =10μl ~ 0.151μg | =10μl ~ 1μg | =10μl ~ 0.3μg |

| FT1 =10μl ~0.06μg | FT1 =10μl ~0.119μg | FT1 =10μl ~0.06μg | FT1 =10μl ~0.7μg |
|---|---|---|---|
| FT2 =10μl ~0.1μg | FT2 =10μl ~0.065μg | FT2 =10μl ~0.6μg | FT2 =10μl ~0.7μg |
| W1 =45μl ~0μg | W1 =45μl ~0.2μg | W1 =45μl ~1.6μg | W1 =45μl ~0.08μg |
| W2 =45μl ~0μg | W2 =45μl ~0.045μg | W2 =45μl ~0.3μg | W2 =45μl ~0.2μg |
| E1=40μl ~0μg | E1=40μl ~0μg | E1=40μl ~0μg | E1=40μl ~0μg |
| E2=40μl ~0μg | E2=40μl ~0.05μg | E2=40μl ~0.4μg | E2=40μl ~0.5μg |
| E3=40μl ~0.3μg | E3=40μl ~0.6μg | E3=40μl ~1μg | E3=40μl ~0.3μg |

Figure 7
(a)
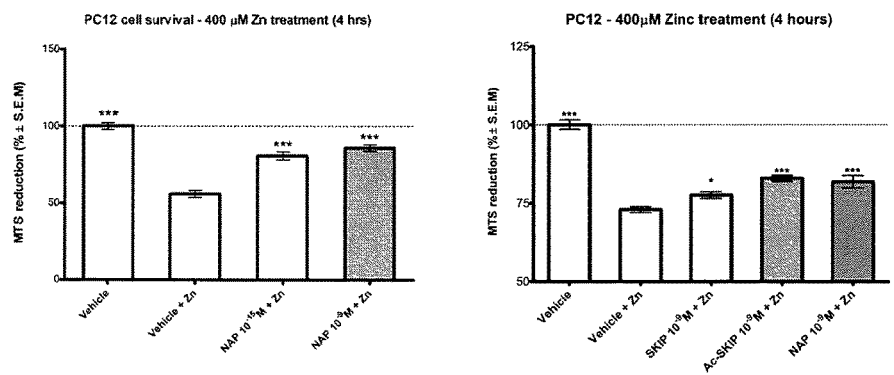
(b)
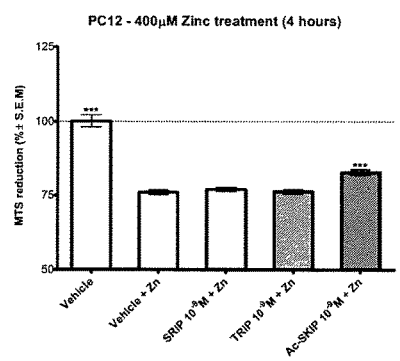

Figure 9
(a)
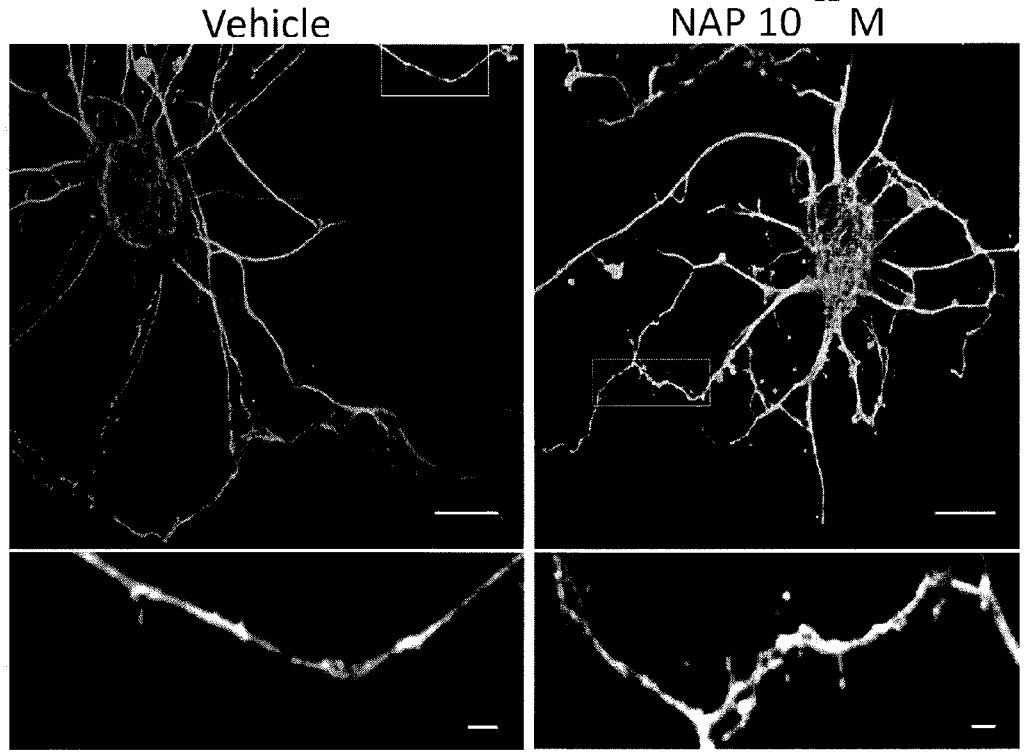
(b)
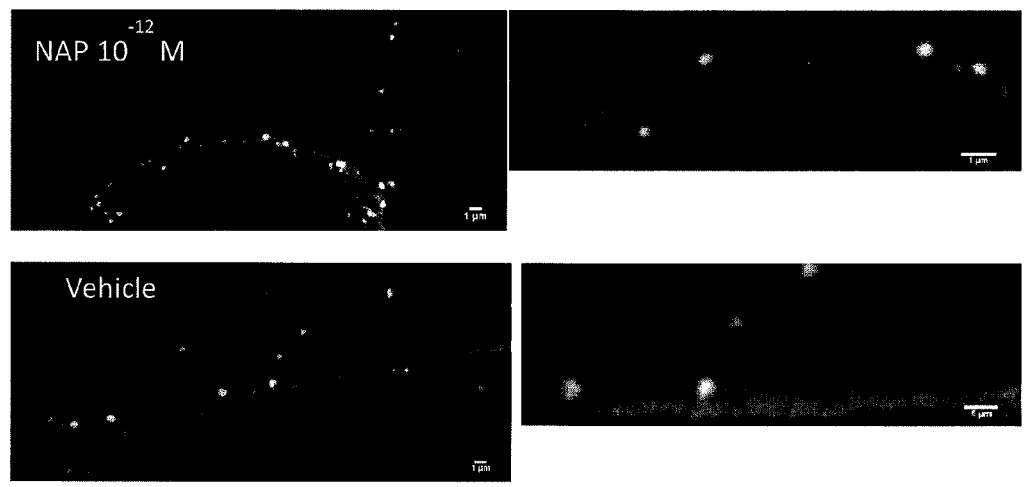

Figure 10
(a)
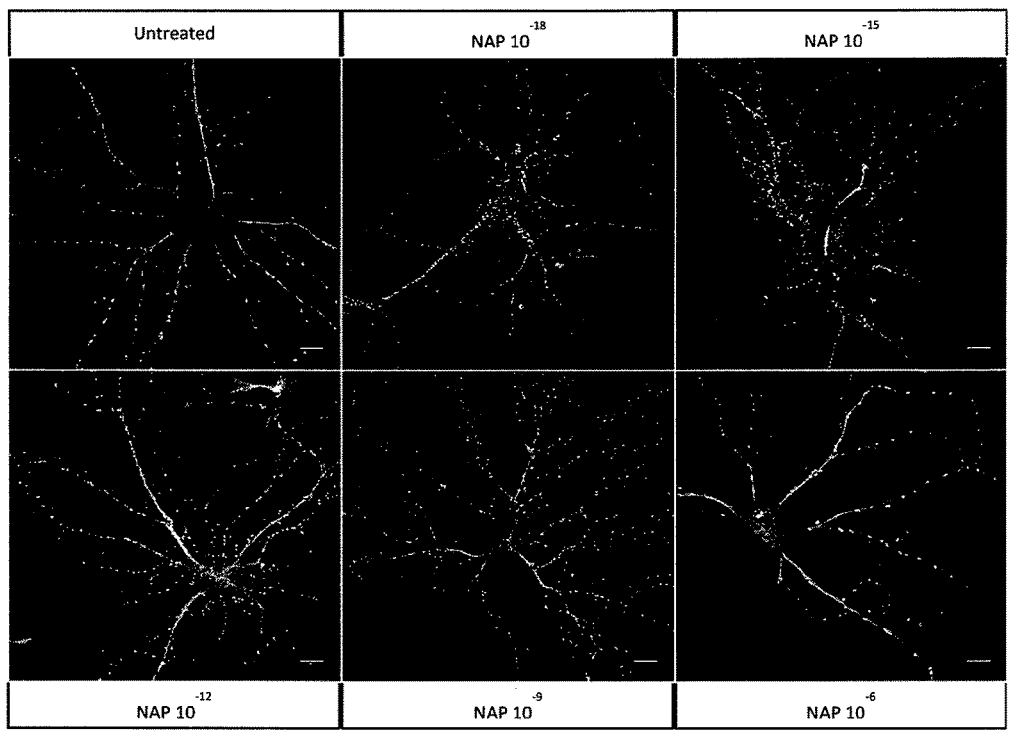
(b)
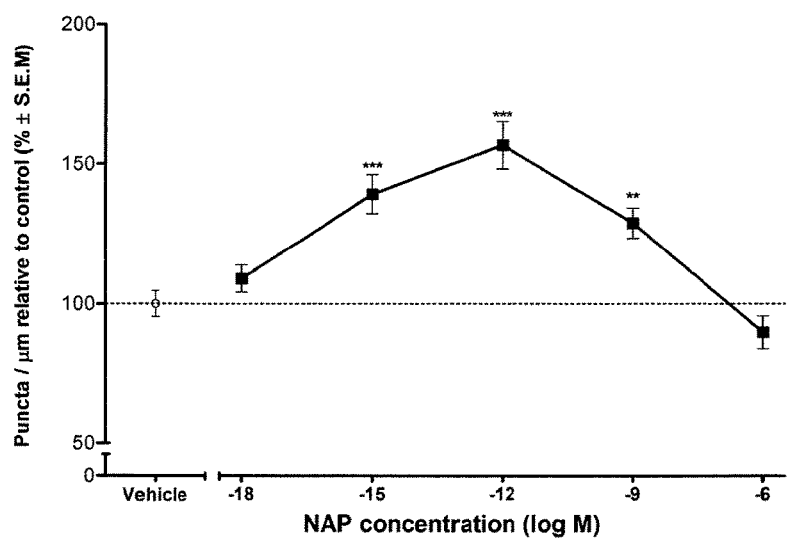

Figure 10 (Continued)
(c)
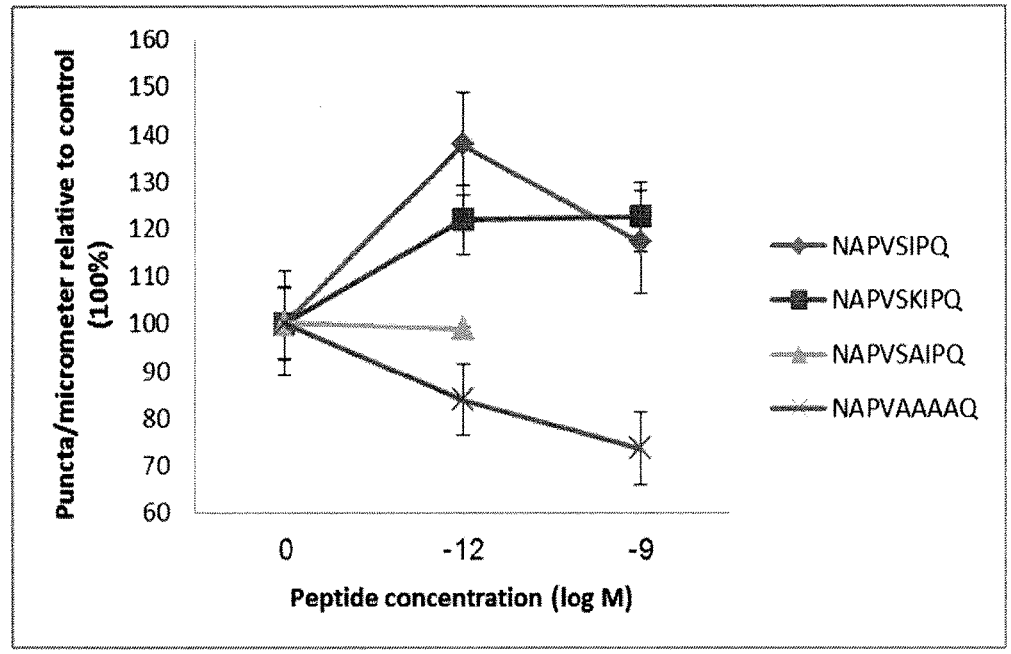
(d)
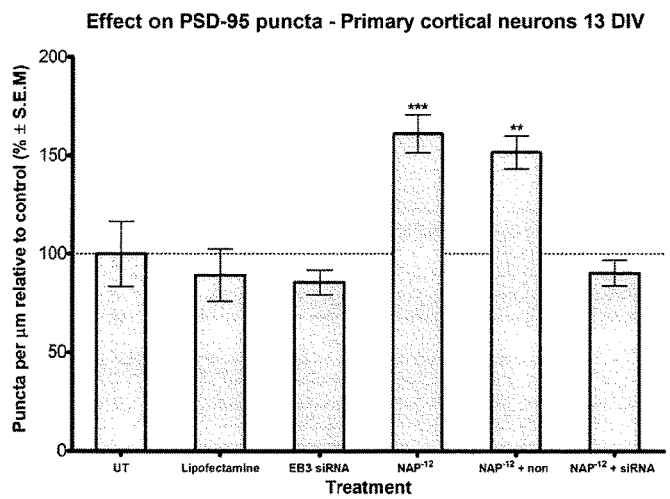

Figure 11
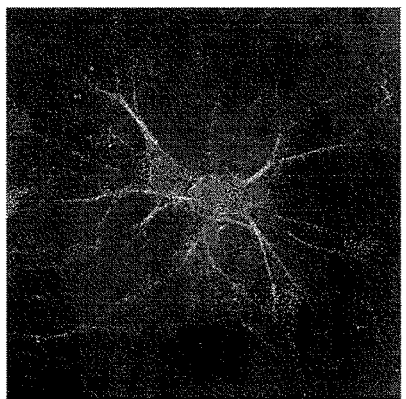
$10^{-12}$M NAP treatment for two hours resulted in a marked increase in PSD-95 expression (green) in isolated cortical neurons in culture (2 hour treatment) - treated above, non-treated below.
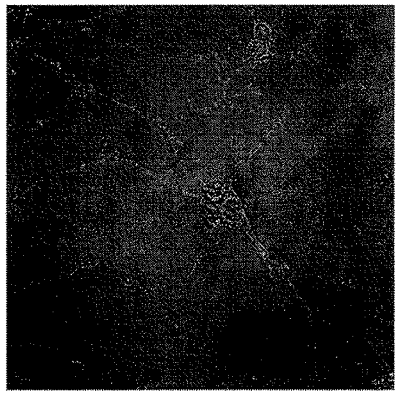

Structure–activity relation for NAP protection of cortical cultures from TTX toxicity.

Figure 14
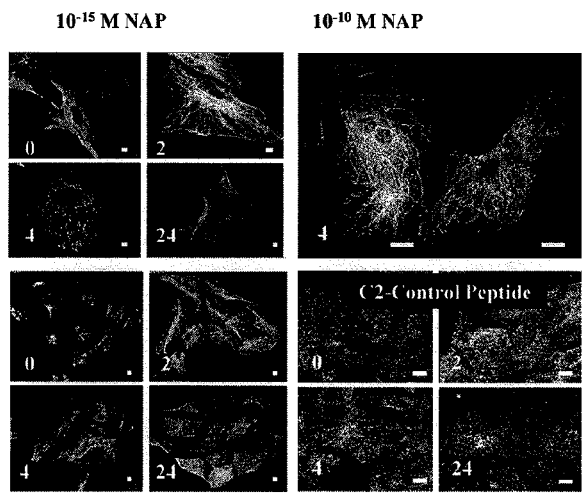
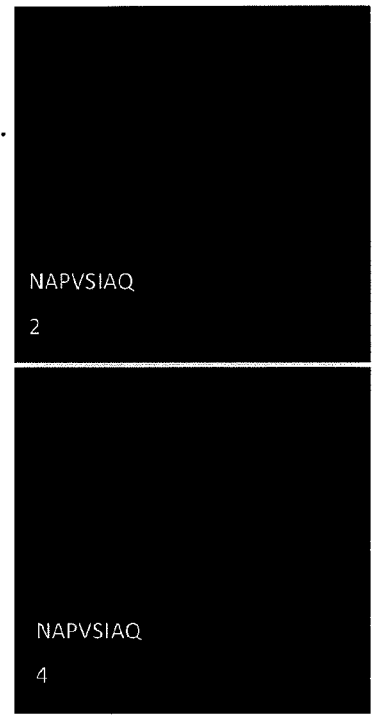
Divinski, Mittleman and Gozes, JBC, 2004
NAPVSIPQ affects the microtubule network –
see 4hr treatment (4), this is not maintained with
$10^{-15}$M NAPVSIAQ, which does not seem to bind to EB.
$10^{-15}$ M NAP      $10^{-10}$ M NAP

Figure 15
A.
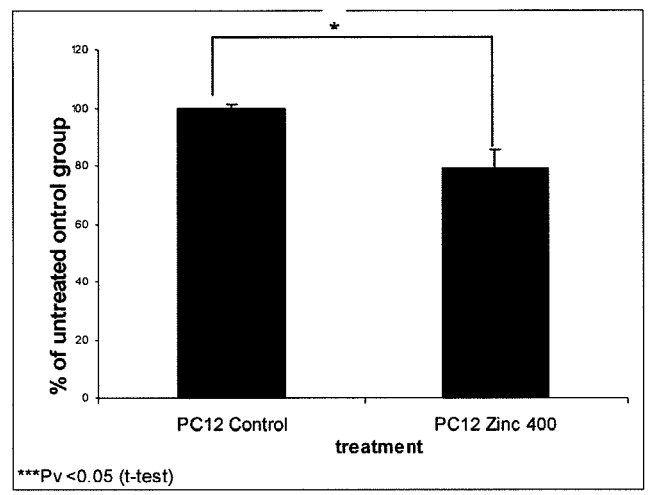
B.
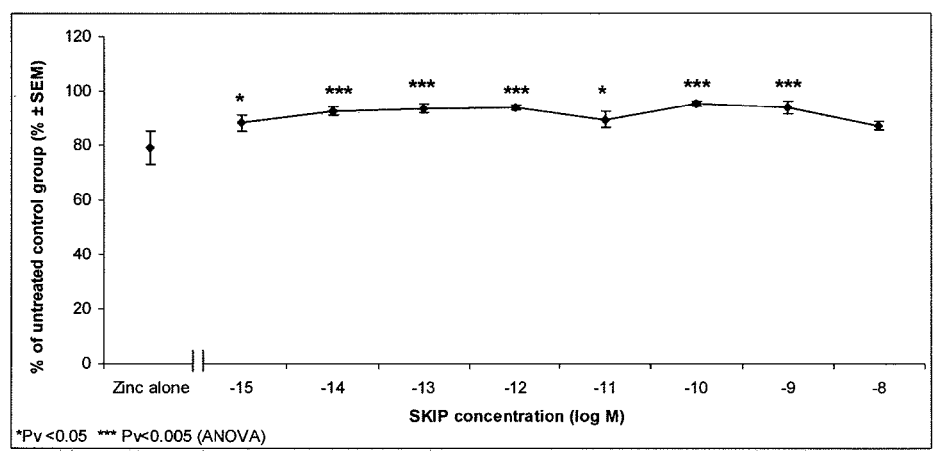

Figure 16
A.
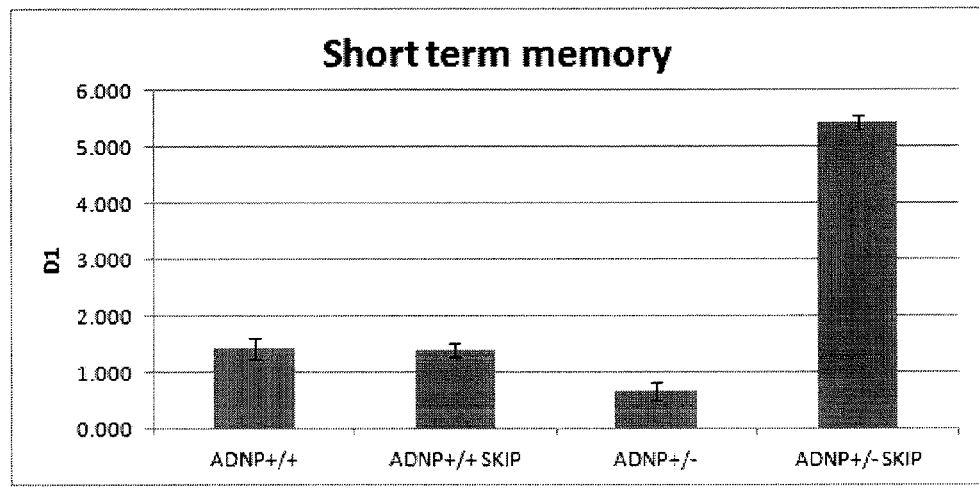
B.
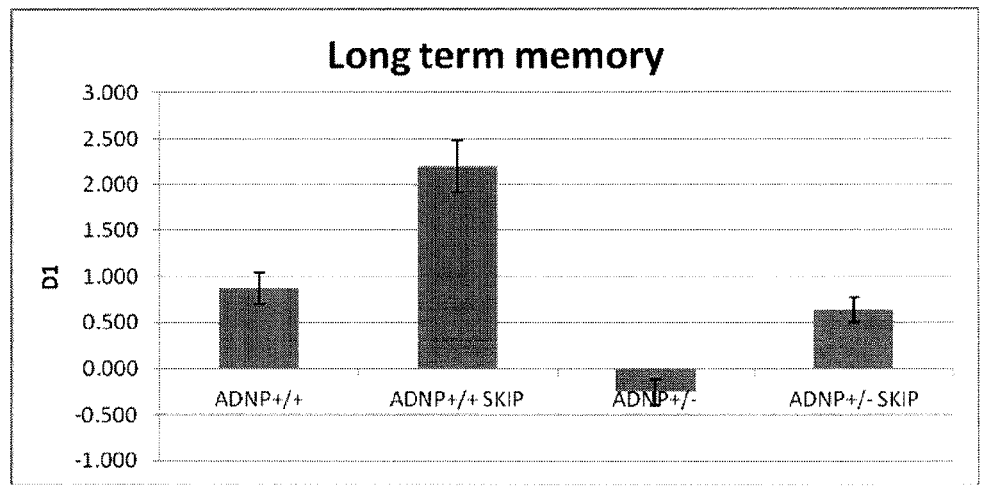

Figure 19
Zinc + NAPVSGIPQ (after 180 min with MTS)
A.
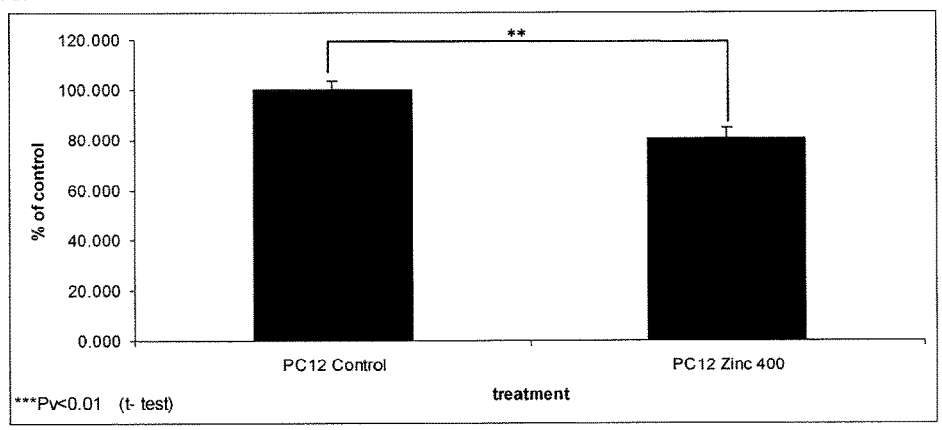
B.
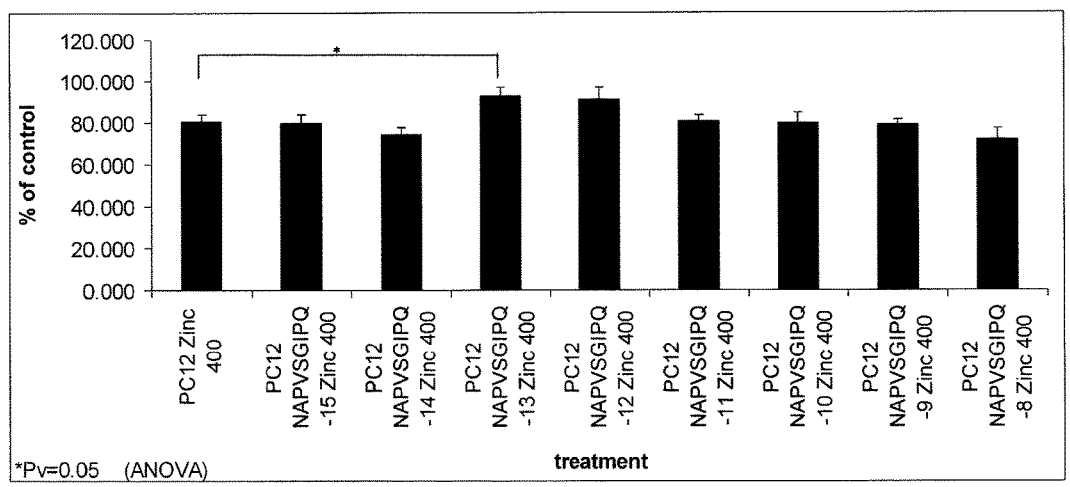

US 10,118,943 B2

COMPOUNDS AND METHODS FOR INHIBITING CELL DEATH

RELATED APPLICATIONS

This application is the U.S National Stage Entry under § 371 of International Application No. PCT/IB2013/051957, filed Mar. 12, 2013, which claims priority to U.S. Provisional Patent Application No. 61/647,661, filed May 16, 2012, the contents of which are hereby incorporated by reference in the entirety for all purposes.

BACKGROUND

The plus ends of growing microtubules (MTs) accumulate a diverse group of MT-associated proteins including the end-binding (EB) protein family. Like other MT plus-end tracking proteins (+TIPs), EB proteins mediate interactions between the ends of MTs, organelles, and protein complexes as well as altering MT stability. Of the three EB family members, EB3 is preferentially expressed in the CNS and is used to track MT dynamics. EB1 was shown to interact with a conserved binding site in +TIPS—namely, SxIP. EB3 is associated with cellular differentiation, and it may form a dimer with EB1 and act also in neuroprotection.

Some recent reports have shown EB3 interaction with PSD-95 at the level of the dendritic modeling and plasticity. See, e.g., Sweet et al., *Bioarchitecture* 2011, 1(2):69-73; Sweet et al., *J. Neurosci.* 2011, 31(30):1038-1047. Thus, EB3 plus-end decorated MTs control actin dynamics and regulate spine morphology and synaptic plasticity, through interaction with PSD-95, and NMDA receptor activation.

BRIEF SUMMARY OF THE INVENTION

This invention relates to novel compounds, e.g., peptides, that possess biological activities including promoting cell survival and/or inhibiting cell death upon exposure to a toxic agent, or promoting cell plasticity, especially in neuronal cells, e.g., protecting synaptic vitality against synaptic disruption and death. The present invention also illustrates for the first time a mechanism of action in protection against cell death: the microtubule End Binding (EB) proteins (e.g., EB3 protein) play an active role in the process and are therefore potential targets for modulating cell susceptibility to apoptosis.

In a first aspect, this invention provides an isolated peptide that protects cells from apoptosis, especially in neuronal cells, e.g., protecting synaptic vitality against synaptic disruption and death. This peptide contains a core sequence of (1) SKIP (Ser-Lys-Ile-Pro, SEQ ID NO:6); (2) SGIP (Ser-Gly-Ile-Pro, SEQ ID NO:7); (3) SRIP (Ser-Arg-Ile-Pro, SEQ ID NO:8); or (4) a core sequence of NAPVSx-IPQ (SEQ ID NO:1, for example NAPVSGIPQ, SEQ ID NO:5) or a conservatively modified variant thereof (e.g., NAPVTxIPQ), and it has up to 40 amino acids at either or both of its N-terminus and the C-terminus. Further, the peptide may contain one or more lipohylic moieties. The peptide has the biological activity of inhibiting cell death, especially in neuronal cells. In some cases, the core amino acid sequence is NAPVSKIPQ (SEQ ID NO:2). In some cases, the peptide has up to 20 amino acids at either or both of the N-terminus and the C-terminus. In other cases, the peptide consists of the core amino acid sequence, such as SKIP (SEQ ID NO:6), SGIP (SEQ ID NO:7), SRIP (SEQ ID NO:8), or SEQ ID NO:2 or 5. In some embodiments, the peptide is modified at one or more locations, for example, the peptide may be acetylated at the N-terminus or at an internal K residue, or it may be lipidated at the N-terminus, or it may be amidated at the C-terminus. In some embodiments, the core amino acid sequence comprises at least one D-amino acid, and may have all D-amino acids. One example is all D-amino acid SKIP (SEQ ID NO:6), and another example is acetyl-SKIP-NH$_2$. In one example, the peptide is not NAPVSRIPQ.

In a second aspect, this invention provides a method for identifying modulators that promote cell survival or cell plasticity by detecting binding between a candidate compound and an EB protein, or by detecting the ability of a candidate compound to promote the expression of an EB protein. In one first method for identifying a modulator of cell survival, at least these steps are performed: (1) contacting, under conditions permissible for protein-modulator binding, an EB protein with a candidate compound; (2) detecting binding between the EB protein and the candidate compound; and (3) identifying the candidate compound as a modulator of cell survival or plasticity when binding between the EB protein and the candidate compound is detected. In a second, cell-based method for identifying a modulator of cell survival or plasticity, at least these steps are performed: (1) contacting a cell that expresses an EB protein, under conditions permissible for the expression of the EB protein, with a candidate compound; (2) detecting the expression level of the EB protein in the cell; and (3) identifying the candidate compound as a modulator that promotes cell survival or plasticity when an increased expression level of the EB protein in the cell is detected, and identifying the candidate compound as a modulator that suppresses cell survival or plasticity when a decreased expression level of the EB protein in the cell is detected. In either of these methods, the EB protein may be an EB1 protein, or an EB2 protein, or an EB3 protein, which may be derived from any suitable species (e.g., a human or rodent version of the EB protein). In either method, step (1) may further comprise providing another protein, for example any one of those identified in Tables 2 and 3 (e.g., a drebrin protein of a suitable species) to interact with the EB protein and the candidate compound. In the cell-based method, the cell used during the screening process may express both EB1 and EB3 proteins, or it may express an EB protein and another protein identified in Tables 2 and 3. In some examples, the cell is a neuronal cell, such as a PC12 cell. In some cases, cell plasticity is neuronal plasticity or synaptic plasticity.

In a third aspect, the present invention provides a method for promoting cell survival/plasticity or inhibiting cell death by contacting the cell with an effective amount of a modulator that promotes cell survival or plasticity. Such a modulator may be of any chemical nature: it may be a peptide described in the first aspect of this invention; it may be a compound that, when administered to a cell in an adequate amount, can increase EB protein expression; it may be a modulator the promotes cell survival/plasticity as identified by the screening method described in the second aspect of this invention. In some cases, the cell is a neuronal cell, which may be present in a patient's body. In some cases, the modulator is a peptide comprising or consisting of the amino acid sequence of (1) SKIP (SEQ ID NO:6); (2) SGIP (SEQ ID NO:7); (3) SRIP (SEQ ID NO:8); or (4) SEQ ID NO:1, SEQ ID NO:2, or SEQ ID NO:5. The modulators of cell survival/plasticity as described herein or identified by the screening methods described herein can be used for treating a patient suffering from a condition involving excessive cell death or inadequate neuronal or synaptic plasticity, e.g., any one of neurodegenerative disorders, including but not limited to, Alzheimer's disease, Parkinson's disease, corticobasal ganglionic degeneration, progressive supranuclear palsy, progressive bulbar palsy, amyotrophic lateral sclerosis, Pick's atrophy, diffuse Lewy body disease, multiple sclerosis, Huntington's disease, a neurodegenerative pathology associated with aging, and a pathological change resulting from a focal trauma (such as stroke, focal ischemia, hypoxic-ischemic encephalopathy, closed head trauma, or direct trauma), peripheral neuropathy, retinal neuronal degeneration (e.g., retinopathy, such as different types of age-related macular degeneration), or dopamine toxicity. Further, these modulators may also be used for treating a patient suffering from a condition involving impaired neuronal plasticity, such as mental disorders and neurodevelopmental disorders including but not limited to anxiety disorders (e.g., any one of specific phobias, generalized anxiety disorder, social anxiety disorder, panic disorder, agoraphobia, obsessive-compulsive disorder, and post-traumatic stress disorder), mood disorders (e.g., major depression, dysthymia, and bipolar disorder), psychiatric disorders (e.g., schizophrenia, delusional disorder, and schizoaffective disorder), personality disorders (e.g., paranoid, schizoid, and schizotypal personality disorders, antisocial, borderline, histrionic or narcissistic personality disorders; anxious-avoidant, dependent, or obsessive-compulsive personality disorders, and adjustment disorders), eating disorders (e.g., anorexia nervosa, bulimia nervosa, exercise bulimia or binge eating disorder), sleep disorders (e.g., insomnia), sexual or gender identity disorders, impulse control disorders (e.g., kleptomania and pyromania), substance abuse disorders, dissociative identity disorders (e.g., depersonalization disorder or multiple personality disorder), developmental disorders (e.g., autism spectrum disorders, oppositional defiant disorder, conduct disorder, and attention deficit hyperactivity disorder or ADHD).

In another aspect, this invention provides a composition that comprises (1) a modulator that promotes cell survival/plasticity as described herein; and (2) a physiologically/pharmaceutically acceptable excipient. Such a composition is useful for promoting cell survival/plasticity or for suppressing undesired cell death, especially in neuronal cells, e.g., protecting synaptic vitality against synaptic disruption and death, or improving synaptic plasticity. One example is treating a patient suffering from a condition involving excessive cell death or inadequate neuronal or synaptic plasticity, e.g., any one of neurodegenerative disorders, including but not limited to, Alzheimer's disease, Parkinson's disease, corticobasal ganglionic degeneration, progressive supranuclear palsy, progressive bulbar palsy, amyotrophic lateral sclerosis, Pick's atrophy, diffuse Lewy body disease, multiple sclerosis, Huntington's disease, a neurodegenerative pathology associated with aging, and a pathological change resulting from a focal trauma (such as stroke, focal ischemia, hypoxic-ischemic encephalopathy, closed head trauma, or direct trauma), peripheral neuropathy, retinal neuronal degeneration (e.g., retinopathy, such as different types of age-related macular degeneration), or dopamine toxicity. Another example is treating a patient suffering from a condition involving impaired neuronal plasticity, such as mental disorders and neurodevelopmental disorders including but not limited to anxiety disorders (e.g., any one of specific phobias, generalized anxiety disorder, social anxiety disorder, panic disorder, agoraphobia, obsessive-compulsive disorder, and post-traumatic stress disorder), mood disorders (e.g., major depression, dysthymia, and bipolar disorder), psychiatric disorders (e.g., schizophrenia, delusional disorder, and schizoaffective disorder), personality disorders (e.g., paranoid, schizoid, and schizotypal personality disorders, antisocial, borderline, histrionic or narcissistic personality disorders; anxious-avoidant, dependent, or obsessive-compulsive personality disorders, and adjustment disorders), eating disorders (e.g., anorexia nervosa, bulimia nervosa, exercise bulimia or binge eating disorder), sleep disorders (e.g., insomnia), sexual or gender identity disorders, impulse control disorders (e.g., kleptomania and pyromania), substance abuse disorders, dissociative identity disorders (e.g., depersonalization disorder or multiple personality disorder), developmental disorders (e.g., autism spectrum disorders, oppositional defiant disorder, conduct disorder, and attention deficit hyperactivity disorder or ADHD). A further aspect of this invention is a screening method for identifying modulators that promote cell survival or cell plasticity by detecting binding between a candidate compound and a target protein, or by detecting the ability of a candidate compound to promote the expression of a target protein. Instead of using an EB protein as the target protein as described above, any one of the proteins identified in Tables 2 and 3 may be used in the screening methods in the same manner as described herein. In some cases, any one of these proteins may be used in combination with an EB protein in the binding assay for identifying a potential modulator. In some cases, two or more of the proteins identified in Tables 2 and 3 may be used together in the screening process, especially in the cell-based assay format.

An additional aspect of this disclosure relates to compounds that the inventors have identified as possessing biological activities similar to the peptides described above, e.g., capable of promoting cell survival and/or plasticity, and/or inhibiting cell death, especially when a toxic agent is exposed to the cells, including neuronal cells. While not intended to be bound to any particular theory of mechanism of action, the inventors believe that these compounds act in a fashion similar to the peptides described above in exerting their biological activity, e.g., protecting neuronal cells against cytotoxicity. These compounds are initially identified based on their interaction with the EB proteins (e.g., binding with the EB3 or EB1 protein in an in silico assay). These compounds include: diltiazem, trazodone, acetophenazine, carphenazine, flumazenil, quetiapine, risperidone, fluvoxamine, thiothixene, almotriptan, and methysergide. More information relating to these compounds are provided in Table 4 of this application. These compounds, as well as any other compounds that may be identified through the same or similar screening methods, can be used for promoting cell survival and/or inhibiting cell death in the same or similar manner that the above-described peptides may be used according to this invention.

BRIEF DESCRIPTION OF THE DRAWINGS

FIG. 2: The EB1 binding domain. Similar binding domains are indicated in other members of the EB family, the original scheme by the inventors as presented on the figure was recently corroborated (Laht et al., *Biochem Biophys Acta*, Feb. 21, 2012).

FIG. 3: EB1, 2, 3 protein sequence alignment. Protein sequence alignment of EB1,2,3 (MAPRE1,2,3) from mouse, rat and human origin showing high similarity. Alignment was done using UniProt ClustalW (Higgins et al., *Methods Enzymol* 266:383, 1996). Uniprot identifiers are shown on the left. Colored rectangular indicate the binding cavity interacting residues as reported (Honnappa et al., *Cell* 138: 366, 2009).

FIG. 4: EB1, 2, 3 mRNA expressions in cell cultures. Quantitative RNA analysis (a) Rat cell cultures: rat non-differentiated pheochromocytoma (PC12) cell line, differentiated PC12 cells treated with NGF and primary cultures of astrocytes and neurons grown for 4 days in-vitro (4DIV) or 19DIV. siRNA silencing (in the indicated concentration) of EB3 in PC12 cells and primary neuronal culture compared to cells treated with non-targeting siRNA. (b) Mouse cell cultures: mouse fibroblasts NIH3T3 cell line, non-differentiated (nd) P19 teratocarcinoma cell line, P19 differentiated into neuro-glial-like by retinoic acid (RA) and to cardiomyocyte like cells by DMSO. Neuronal differentiated cells exhibited a relative high expression of EB3, which is specifically inhibited by targeted EB3 RNA silencing.

FIG. 7: NAP protects PC12 cells from zinc intoxication. (a) Zinc treatment (400 µM) resulted in PC12 cell death which was protected against by NAP treatment. Results of mitochondrial activity (MTS cell viability) are shown—100—is 100% survival—control without zinc treatment. (ANOVA, $p<0.0001$, $n=18$, post hoc comparison were made in reference to vehicle +Zn treatment). (b) NAP, NAPVSKIPQ (SKIP) and Acetyl-NAPVSKIPQ (Ac-SKIP), ($10^{-9}$M) each separately significantly increased survival. The protection by the three peptides was similar. (ANOVA, $p<0.0001$, $n=12$-30, post hoc comparison were made in reference to vehicle +Zn treatment). (c) Other peptides tested such as NAPVSRIPQ (SRIP) and NAPVTRIPQ (TRIP) were inactive. Results were similar to the control results. Ac-SKIP was used as an active control. (ANOVA, $p<0.0001$, $n=12$, post hoc comparison were made in reference to vehicle +Zn treatment).

Figure 1:
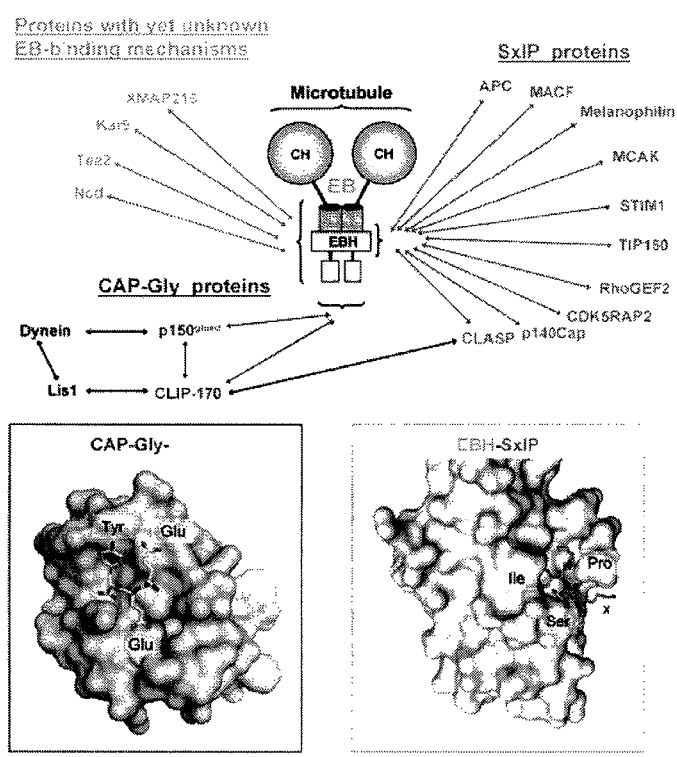
FIG. 1: MT plus-end tracking proteins (+TIPs). +TIPs localize to growing MT ends where they form dynamic interaction networks. These networks rely on a limited number of protein modules and linear sequence motifs such as the calponin homology (CH), EB homology (EBH) and cytoskeleton-associated protein glycine-rich (CAP-Gly) domains, and EEY/F and SxIP sequence motifs (top part). These elements mediate the interaction with each other and MTs, and typically display affinities in the low micromolar range. End-binding (EB) proteins are now generally accepted to represent core components of +TIP network assemblies as they autonomously track growing MT plus-ends independently of any binding partners. Moreover, EB proteins directly associate with almost all other known +TIPs and by doing so target them to growing MT plus-ends. SxIP motifs act as a general 'MT tip localization signal' by interacting with the EBH domain of EB proteins. Likewise, EEY/F motifs of EB proteins and α-tubulin guide CAP-Gly proteins to MT tips. EBH-SxIP and the CAP-Gly-EEY/F interactions X-ray crystallography analysis (bottom part). The two distinct binding modes revealed by these structures offer a molecular basis for understanding the majority of known interaction nodes in dynamic +TIP networks (adopted from BMR: Dynamic Protein Interactions, Michel O. Steinmetz Paul Scherrer Institute).

| | Source of Variation | | | | |
|---|---|---|---|---|---|
| | DF | SS | MS | F | P |
| Between Groups | 5 | 0.526 | 0.105 | 6.888 | <0.001 |

All Pairwise Multiple Comparison Procedures (Student-Newman-Keuls Method): NAP protects in the control situations, but not in the presence of EB3 silencing.

FIG. 9: MT in dendritic protrusions. Cortical neurons were treated with vehicle or NAP ($10^{-12}$M) at 13 DIV for 2 hrs and then fixed and stained. (a) Representative images showing dendritic protrusion exhibiting Tyr-MT (red) Glu-MT (green) or both. Bars: 10 µm. Bars in magnified areas 1 µm. (b) Representative images showing dendritic protrusion exhibiting Tyr-MT (red) Glu-MT (blue) and PSD-95 (green). Images on the right side are a magnification of the central area of the left side images. Bars: 1 µm.

FIG. 10: Treatment with NAP increases PSD-95 accumulation in dendritic spines. Methods: 1. Primary cultures of neurons were prepared as follows. Newborn rats were sacrificed on postnatal day 1. Cerebral cortex tissue was then dissected and dissociated individually from each pup with the Papain Dissociation System (PDS; Worthington Biochemical Corporation) according to the manufacturer's instructions. 2. Cells were fixed with ice cold methanol, blocked with 2% bovine serum albumin (BSA) and 5% normal goat serum in Tris buffered saline containing tween 20 (TBS-T; 20 mM Tris pH 7.5, 136.8 mM NaCl, and 0.05% v/v Tween 20), and incubated with primary antibody followed by the appropriate secondary antibody. 3. Primary antibodies that were used include: monoclonal anti PSD-95 (ab-2723, Abcam), monoclonal anti Tyr-α-tubulin antibody (YL1/2) (VMA1864, Abcys, Paris, France), polyclonal anti Glu-α-tubulin antibody (L4) (AbC0101, Abcys, Paris, France), DyLight 488-labeled secondary goat anti-mouse IgG, DyLight 633-labeled secondary goat anti-rabbit IgG (KPL, Gaithersburg, Md., USA), Cy3-conjugated secondary goat anti-Rat IgG, (Jackson ImmunoResearch). 4. Images were collected with a Leica SP5 confocal laser scanning microscope (Mannheim, Germany) with 63× oil immersion optics, laser lines at 488, 561, 633 nm. Identical confocal laser scanning microscopy (CLSM) parameters (e.g., scanning line, laser light, gain, and offset etc.) were used for control and NAP treated cells.

Legend: Cortical neurons were treated with vehicle or NAP ($10^{-18}$M-$10^{-9}$M) at DIV 13 for 2 hrs and then fixed and stained for Tyr-tubulin, Glu-tubulin and PSD-95. (a) Representative images of cortical neurons stained for Tyr-tubulin (red), PSD-95 (green), Glu-tubulin (blue). Bars: 10 µm. (b) Comparison of the effect on PSD-95 density. Results show that the density of PSD-95 puncta was significantly increased in neurons treated with NAP for 2 hrs when compared to vehicle controls. Zinc reduced cell viability by ~25 percent (P<0.0001, ANOVA, Dunnett post hoc, n=25 dendrites per treatment). NAP, SKIP and Ac-SKIP ($10^{-9}$M) each separately significantly increased survival (*P<0.05, ***P<0.001). (c) Comparison of the derivative peptides effect on PSD-95 density. Results show that the density of PSD-95 puncta was significantly increased in neurons treated for 2 hrs with NAPVSIPQ or NAPVSKIPQ when compared to vehicle controls, and was not affected by the NAPVSAIPQ or NAPVAAAAQ peptides. (ANOVA, p<0.0001, n=14-48 dendrites per treatment). (d) 13 DIV cortical neurons were either untreated (UT), treated with transfection reagent (Lipofectamine RNAiMAX), treated with siRNA against EB3, treated with NAP ($10^{-12}$M), treated with NAP ($10^{-12}$M) and non-targeting control siRNA (non), or treated with NAP ($10^{-12}$M) and siRNA against EB3. 2 hrs treatment with $10^{-12}$M NAP increased PSD-95 expression by 75% and this was completely inhibited by 48 hours EB3 silencing. (ANOVA, p<0.0001, n=18 dendrites per treatment).

FIG. 11: Treatment with NAP increases PSD-95 accumulation in dendritic spines. Methods: 1. Primary cultures of neurons were prepared as follows: Newborn rats were sacrificed on postnatal day 1. Cerebral cortex tissue was then dissected and dissociated individually from each pup with the Papain Dissociation System (PDS; Worthington Biochemical Corporation) according to the manufacturer's instructions (as in FIG. 10). 2. Antibodies—monoclonal anti PSD-95 (ab-2723, Abcam) (as in FIG. 10), DyLight 488-labeled secondary goat anti-mouse IgG. Hoechst dye was used to visualize nuclei. 3. Cells were fixed with ice cold methanol, blocked with 2% bovine serum albumin (BSA) and 5% normal goat serum in Tris buffered saline containing tween 20 (TBS-T; 20 mM Tris pH 7.5, 136.8 mM NaCl, and 0.05% v/v Tween 20), and incubated with primary antibody followed by the appropriate secondary antibody. 4. Images were collected with Images were collected with a Leica SP5 confocal laser scanning microscope (Mannheim, Germany) with 40× oil immersion optics, laser lines at 488, 561, 633 nm. Identical confocal laser scanning microscopy (CLSM) parameters (e.g., scanning line, laser light, gain, and offset etc.) were used for control and NAP treated cells.

Legend: Representative images showing PSD-95 expression in primary cortical neurons treated with NAP ($10^{-12}$M) or vehicle (control). Cortical neurons were treated with vehicle or NAP ($10^{-12}$M) at DIV 13 for 2 hours and were then fixed and stained for PSD-95. Field view of primary cortical neurons (visible light/phase contrast) stained for PSD-95 (green) is seen. This figure differs from FIG. 10, as it is viewed under different magnification and different illumination.

Figure 12:
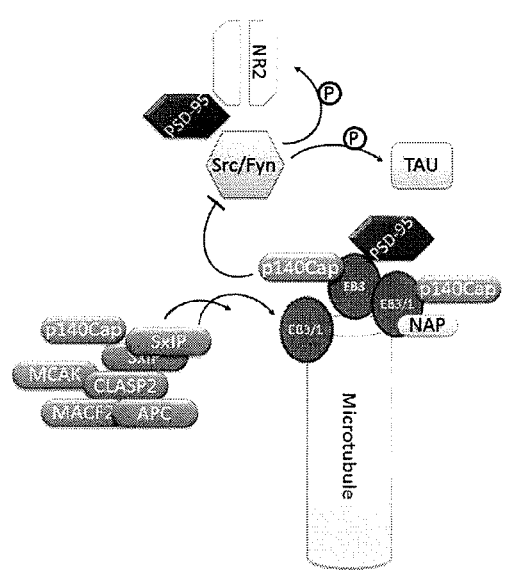

FIG. 12: Proposed mechanism of action for NAP. NAP interacts with EB3 or EB3/EB1 dimer. This interaction promotes and increases other SxIP proteins like p140Cap to interact with EB's. These SxIP proteins regulate, for example, Src/Fyn which in turn regulates phosphorylation of tau. Alternatively, NAP acts as an interfering peptide that prevents depolymerizing +TIPs while maintaining MT dynamics.

Figure 13:
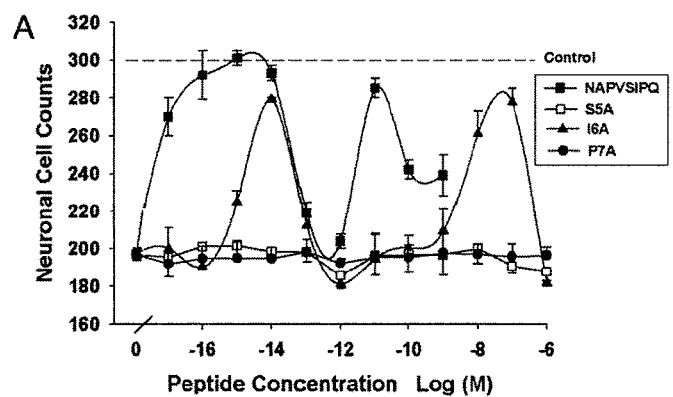

FIG. 13: Protection of cortical culture by NAP-like peptides.

FIG. 14: NAPVSIPQ affects the microtubule network.

FIG. 15: Rat pheochromocytoma cells (PC12) were seeded on Poly-D-Lysine coated 96-well tissue culture dishes in high concentration (30,000 cells/well). On the day of the experiment the cells were treated with $ZnCl_2$ (400 µM) either alone or in combination with different concentration of SKIP for 4 h. After 4 h the cell viability was analyzed by MTS assay. (A) The exposure of the PC12 cells to $ZnCl_2$ induced a significant reduction in the cell viability. (B) SKIP (SEQ ID NO:6) at concentrations of $10^{-15}$M, $10^{-9}$M showed protection against Zn intoxication (significantly higher viability compared to Zn alone). All values are from one experiment performed in hexplicate. The experiment was repeated several times showing protection at various concentrations.

FIG. 16: SKIP (SEQ ID NO:6) treatment increases the relative discrimination between novel and familiar objects. Animal performance in the object recognition memory test is shown. Data are expressed as mean (±SEM) total time (s) spent exploring all objects designated by relative discrimination index (D1) in Phase 2 (A) and Phase 3 (B). Two identical objects were presented during Phase 1, and one of the identical objects was replaced by a novel object during Phases 2 and 3. The ADNP-deficient mice tended to spend less time in exploring the new objects during Phases 2 and 3 as compared to control mice (ADNP+/+). SKIP (SEQ ID NO:6) treatment improved short and long term memory for the ADNP-deficient mice. The data was analyzed using the following formula: D1=b−a, when 'a' designated the time of exploration of the familiar object and 'b' designated the time of exploration of the novel object. The formula evaluates the discrimination capacity of the mice between the novel object and the familiar object. The results were tested statistically using ANOVA test ([*] p<0.05).

Figure 17:
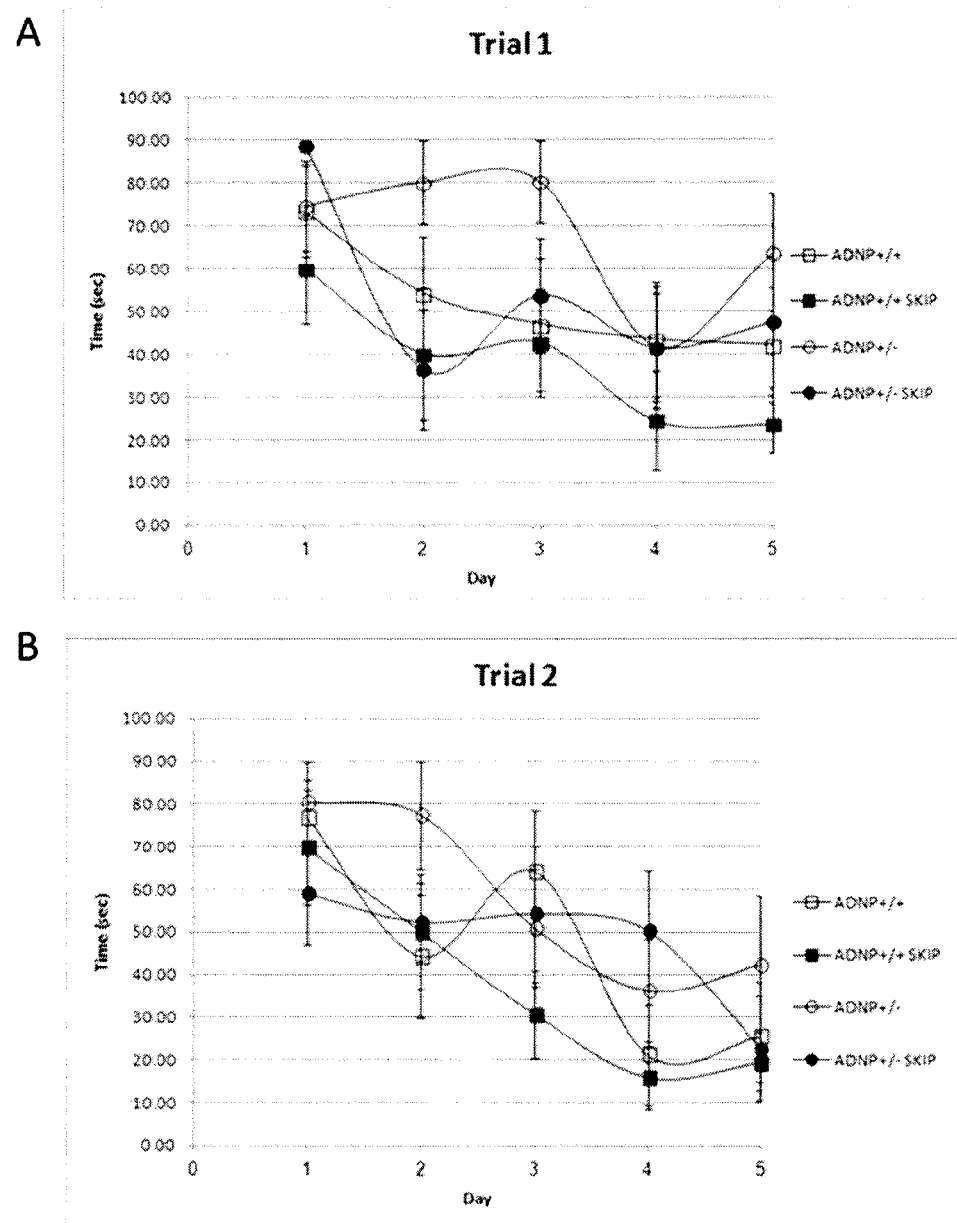

FIG. 17: ADNP+/− male mice exhibit spatial learning deficiencies: improvements by SKIP (SEQ ID NO:6) treatment. Two daily water maze tests were performed: first (A) and second (B). Males (ADNP+/+, n=14; ADNP+/−, n=13) were compared. Tests were performed over 5 consecutive days. Latency measured in seconds (mean±S.E.) to reach the hidden platform in its new daily location is depicted. A, ADNP+/− male mice were impaired compared with control animals. Treatment with SKIP (SEQ ID NO:6) for 1 month (twice a day) improved the memory. B, statistically significant difference (p<0.05, two tailed t-test) between the ADNP+/+ mice and ADNP+/− mice on the 5$^{th}$. SKIP (SEQ ID NO:6) treatment resulted in improvement in the behavior of the ADNP-deficient mice, bringing them to the control levels.

Figure 18:
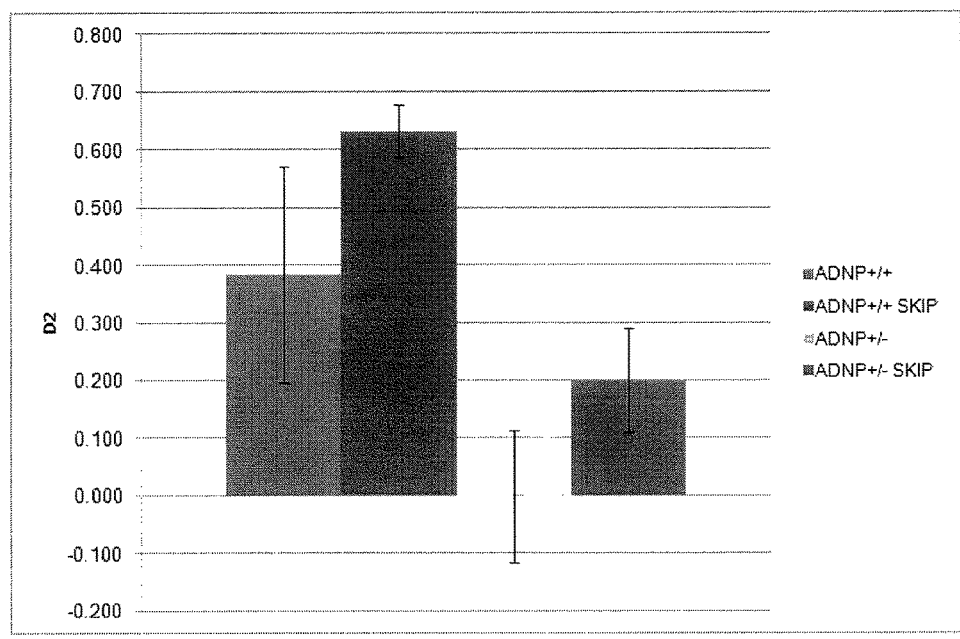

FIG. 18: ADNP+/− male mice exhibit risky behavior in the elevated plus maze test. The number of total arm entries (counts) and time spent in the open-arms for 5 min are presented. Data are expressed as mean±SEM. ANOVA test showed a significant difference (P<0.01) of the time spent in the open and closed arms between ADNP+/+ mice and ADNP+/− mice. SKIP (SEQ ID NO:6) treatment resulted in improvement in the risky behavior of the ADNP-deficient mice.

FIG. 19: Peptide NAPVSGIPQ (SEQ ID NO:5) exhibits protective activity in PC12 cells after exposure to $ZnCl_2$ (400 µM). The same experimental procedure was followed as in the experiments shown in FIG. 15. NAPVSGIPQ (SEQ ID NO:5) at concentration of $10^{-13}$M showed protection against Zn toxicity (significantly higher viability compared to Zn alone).

DEFINITIONS

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO 01/12654, which may improve stability, oral availability and other drug-like characteristics of the compound containing such D-amino acids. In such embodiments, one or more, and potentially all of the amino acids of the peptides of this invention will have D-chirality. The therapeutic use of peptides can be enhanced by using D-amino acids to provide longer half-life and duration of action. However, many receptors exhibit a strong preference for L-amino acids, but examples of D-peptides have been reported that have equivalent activity to the naturally occurring L-peptides, for example, pore-forming antibiotic peptides, beta amyloid peptide (no change in toxicity), and endogenous ligands for the CXCR4 receptor. In this regard, NAP and related polypeptides also retain activity in the D-amino acid form (Brenneman et al., *J. Pharmacol. Exp. Ther.* 309(3):1190-7 (2004); U.S. Pat. No. 8,017,578).

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (1), Leucine (L), Valine (V); and
8) Phenylalanine (F), Tyrosine (Y), Tryptophan (W) (see, e.g., Creighton, Proteins (1984)).

The terms "polypeptide," "peptide," and "protein" are used interchangeably herein to refer to a polymer of amino acid residues. Generally, a peptide refers to a short polypeptide. The terms apply to amino acid polymers in which one or more amino acid residue is an analog or mimetic of a corresponding naturally occurring amino acid, as well as to naturally occurring amino acid polymers.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing the interaction between a protein or peptide and another agent or compound (e.g., an antibody), refers to a binding reaction that is determinative of the presence of the protein in a heterogeneous population of proteins and other biologics. Thus, under designated assay conditions, the specified binding agent (e.g., an antibody) binds to a particular protein at least two times the background and does not substantially bind in a significant amount to other proteins present in the sample. Specific binding to an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background.

The term "subject" or "patient" refers to any mammal, in particular human, at any stage of life.

The term "contacting" is used herein interchangeably with the following: combined with, added to, mixed with, passed over, incubated with, flowed over, etc. Moreover, the peptides or other apoptosis modulators of the present invention can be "administered" by any conventional method such as, for example, parenteral (e.g., intravenous, subcutaneous, intradermally or intramuscularly), oral, topical, intravitreal and inhalation (e.g., intranasal) routes.

As used herein "treatment" includes both therapeutic and preventative treatment of a condition, such as treatment for alleviating ongoing symptoms and prevention of disease progression or onset of further symptoms, or for avoidance or reduction of side-effects or symptoms of a disease. As used herein the term "prevent" and its variations do not require 100% elimination of the occurrence of an event; rather, the term and its variation refer to an inhibition or reduction in the likelihood of such occurrence.

As used herein, "condition" and "disease" include incipient conditions or disorders, or symptoms of a disease, incipient condition or disorder.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that protein gives rise to essentially one band in an electrophoretic gel. Particularly, it means that the protein is at least 85% pure, more preferably at least 95% pure, and more preferably at least 99% pure.

"An amount sufficient (or effective)" or "an effective amount" or a "therapeutically effective amount" is that amount of a therapeutic agent at which the agent exhibits its activity for the intended purpose of its administration. In therapeutic applications, an amount adequate to accomplish this is defined as the "therapeutically effective dose." For example, an effective amount for a neuroprotective agent (e.g., a peptide containing the core amino acid sequence of SEQ ID NO:1) of the invention is an amount that when administered to a patient suffering from or at risk of developing a disorder involving excessive and underdesired neuronal cell death (e.g., a neurodegenerative disorder), the agent is capable to reducing or substantially eliminating excessive cell death in neuronal cells, or reducing or substantially eliminating the risk of developing a neurodegenerative disorder.

The term "neuroprotective activity" is used in this application to refer to a biological activity exhibited by a compound, e.g., a peptide, that measurably reduces, prevents, or eliminates apoptosis in neuronal cells upon exposure to a toxic agent known to cause death in cells of such variety. For example, whether or not a given compound possesses "neuroprotective activity" can be tested and verified by methods known in the art and/or described herein, including but not limited to, a pheochromocytoma (PC12) cell survival assay involving Zinc toxicity.

As used herein, the term "EB protein" encompasses a group of highly conserved microtubule plus-end tracking proteins, their homologs, orthologs, and variants. There are three main EB proteins in the mammalian species, EB1, EB2, and EB3. The proteins encoded by the MAPRE family are encompassed within the "EB proteins." For example, the amino acid sequences for human and rodent EB proteins and known variants can be found at the NCBI worldwide website (ncbi.nlm.nih.gov). The GenBank Accession numbers for some rodent EB polynucleotide sequences are set forth in Table 1.

10 human EB protein sequences are available

Accession: Q9UPY8.1; GI: 20138791
Accession: NP_001243349.1; GI: 374081840
Accession: NP_001137299.1; GI: 219842327
Accession: NP_036458.2; GI: 10800412
Accession: Q15555.1; GI: 60390165
Accession: Q15691.3; GI: 20138589
Accession: NP_001137298.1; GI: 219842325
Accession: NP_055083.1; GI: 10346135
Accession: AAK07557.1; GI: 12751131
Accession: AAK07556.1; GI: 12751130

-continued

Mouse

EB1: Accession: Q61166.3; GI: 60390180
EB2: Accession: Q8R001.1; GI: 60390207
EB3: Accession: Q6PER3.1; GI: 60390186

Rat

EB1: Accession: Q66HR2.3; GI: 60389848
EB2: Accession: Q3B8Q0.1; GI: 108860788
EB3: Accession: Q5XIT1.1; GI: 60389846

As used in this application, an "increase" or a "decrease" refers to a detectable positive or negative change in quantity from a comparison basis, e.g., an established baseline value of the level of an mRNA encoding an EB protein. An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

The term "cell death" is used in this application interchangeably with the term "apoptosis" to refer to a process known as the programmed cell death (PCD), which involve a series of biochemical events leading to characteristic changes in cell morphology and function, and ultimately, to cell death. These changes include blebbing, cell shrinkage, nuclear fragmentation, chromatin condensation, and chromosomal DNA fragmentation. In this application, this term is used in contrast to "necrosis," which is a form of traumatic cell death that results from acute cellular injury.

The term "cell plasticity," as used in this application, refers to a cell's ability to alter its functional and/or morphological features in response to an internal or external stimulating event. Neuronal or synaptic plasticity refers to the ability of a neuron cell or synapse to change its internal characteristic in response to its history. Such plasticity can include the ability of the entire brain structure and the brain itself to undergo changes from past experience.

As used herein, the term "expression" encompasses both the transcription of a DNA coding sequence into corresponding RNA, indicated by the presence and quantity of the RNA, and the translation of the encoding RNA into a protein product, indicated by the presence and quantity of the protein. In other words, the "expression" of a gene product can be determined and quantified at the level of either the corresponding RNA or corresponding protein.

DETAILED DESCRIPTION OF THE INVENTION

Activity-dependent neurotrophic factors (ADNF) are polypeptides that have neurotrophic or neuroprotective activity as measured with in vitro cortical neuron culture assays described by, e.g., Hill et al., *Brain Res.* 603:222-233 (1993); Brenneman & Gozes, *J Clin. Invest.* 97:2299-2307 (1996), Gozes et al., *Proc. Natl. Acad. Sci. USA* 93, 427-432 (1996). Two well-known ADNF polypeptides comprise an active core site having the amino acid sequence of SALL-RSIPA (often referred to as "SAL") and NAPVSIPQ (often referred to as "NAP"), respectively.

The surprising finding of the present inventors is that the neuroprotective peptides NAP (NAPVSIPQ), NAPVSKIP and SKIP (SEQ ID NO:6) interact with the microtubule (MT) End Binding protein 3 (EB3), which will infer interaction with other EB proteins (e.g., EB1 and EB2). Given (1) the structural similarities among different EB proteins, (2) the fact that the SIP motif is required for NAP activity, and (3) that NAP has a preferential neuroprotection/neurotrophic activity and does not interact with cancer cells, the inventors hypothesized that NAP (NAPVSIPQ) interacts with EB3 (or with the EB family of proteins). In their studies, affinity chromatography showed association of NAP with EB3.

In the studies presented herein, NAP showed significant dose-dependent increase in PSD-95 expression in dendritic spine like structures in cortical neurons in culture. Silencing EB3 mRNA abolished NAP activity, implicating EB3 in the NAP-related neurotrophic effects. Based on NAP structure, several additional novel peptides derived from hybrid sequences of EB3—binding +TIPs and NAP were synthesized including, NAPVSKIPQ; NAPVSAIPQ; NAPVAAAAQ. NAPVSKIPQ mimicked NAP activity, while 1) NAPVSAIPQ, 2) NAPVAAAAQ, 3) NAPVTRIPQ and 4) NAPVSRIPQ were inactive. NAP has been previously shown to protect against MT breakdown and tubulin aggregation in the presence of toxic concentration of zinc that were associated with neuronal and glial death. In a pheochromocytoma (PC12) cell survival assay, the novel NAPVSKIPQ provided protection against zinc toxicity, mimicking NAP activity. Acetyl-NAPVSKIPQ-NH$_2$ also provided cell protection. Similarly, NAPVSGIPQ and the 4-amino acid peptide SKIP (SEQ ID NO:6) provided protection. The NAP target EB3 (or the EB family of proteins) and interacting peptides and peptide mimetics are claimed as a discovery platform/assay system and novel neurotrophic, neuroprotective compounds.

I. Peptides

The peptides of this invention can be obtained by various means well known in the art, such as by chemical synthesis or recombinant production.

A. Chemical Synthesis

The peptides useful according to this invention can be produced chemically, e.g., by systematically adding one amino acid at a time, followed by screening of the resulting peptide for biological activity, as described herein. In some cases, one or more of the amino acids in the core active sites may be substituted by a D-amino acid. In addition, various substitutions may be made to amino acid residues outside of the core sites.

Peptides comprising non-standard amino acids can also be made. In some embodiments, at least one of the amino acids of the active core sequence is a non-standard amino acid. In some embodiments, 2, 3, 4, 5, or more of the amino acids is a non-standard amino acid. In some cases, all amino acids are non-standard amino acid (such as D-amino acid) in a core active site. Examples of non-standard amino acids are alpha-aminoisobutyric acid, N-methylated amino acids, amino acids with a D chiral center, aza-tryptophan, etc. A wide range of non-standard amino acids are commercially available, e.g., at Genzyme Pharmaceuticals (Cambridge, Mass.).

Peptide sequences, including those with non-standard amino acids, can be generated synthetically using commercially available peptide synthesizers to produce any desired polypeptide (see Merrifield, *Am. Chem. Soc.* 85:2149-2154

(1963); Stewart & Young, *Solid Phase Peptide Synthesis* (2nd ed. 1984)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids, or non-standard amino acids, in the sequence is a method for the chemical synthesis of the peptides of this invention. Techniques for solid phase synthesis are described by Barany & Merrifield, *Solid-Phase Peptide Synthesis*; pp. 3-284 in *The Peptides: Analysis, Synthesis, Biology*. Vol. 2: *Special Methods in Peptide Synthesis*, Part A.; Merrifield et al 1963; Stewart et al. 1984). The NAP-derived and other peptides of this invention can be synthesized using standard Fmoc protocols (Wellings & Atherton, *Methods Enzymol.* 289:44-67 (1997)). Furthermore, liquid phase sequential synthesis can be used as well.

B. Recombinant Production

In addition to chemical synthesis, the peptides of this invention, especially those of relatively longer lengths, can be prepared by recombinant DNA methodology. Generally, this involves creating a nucleic acid sequence that encodes the polypeptide, placing the nucleic acid in an expression cassette under the control of a particular promoter, and expressing the protein in a host cell. Recombinantly engineered cells known to those of skill in the art include, but are not limited to, bacteria, yeast, plant, filamentous fungi, insect (especially employing baculoviral vectors), and mammalian cells.

The recombinant nucleic acids are operably linked to appropriate control sequences for expression in the selected host. For *E. coli*, exemplary control sequences include the T7, trp, or lambda promoters, a ribosome binding site and, optionally, a transcription termination signal. For eukaryotic cells, the control sequences can include a promoter and, optionally, an enhancer, e.g., derived from immunoglobulin genes, SV40, cytomegalovirus, etc., a polyadenylation sequence, and splice donor and acceptor sequences.

The plasmids of the invention can be transferred into the chosen host cell by methods such as, for example, the calcium chloride transformation method for *E. coli* and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant polypeptides can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology* Vol. 182: *Guide to Polypeptide Purification* (1990)). Optional additional steps include isolating the expressed polypeptide to a higher degree, and, if required, cleaving or otherwise modifying the peptide, including optionally renaturing the polypeptide.

One of skill can select a desired polypeptide of the invention based upon the sequences provided and upon knowledge in the art regarding proteins generally. Knowledge regarding the nature of proteins and nucleic acids allows one of skill to select appropriate sequences with activity similar or equivalent to the polypeptides disclosed herein.

One of skill will recognize many ways of generating alterations in a nucleic acid sequence encoding a given peptide sequence. Polypeptide sequences can also be altered by changing the corresponding nucleic acid sequence and expressing the polypeptide. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other known techniques (see Giliman & Smith, *Gene* 8:81-97 (1979); Roberts et al., *Nature* 328:731-734 (1987)).

After chemical synthesis, recombinant expression or purification, the polypeptide(s) may possess a conformation substantially different than the native conformations of the constituent polypeptides. In this case, it is helpful to denature and reduce the polypeptide and then to cause the polypeptide to re-fold into the preferred conformation. Methods of reducing and denaturing peptides and inducing re-folding are known to those of skill in the art (see Debinski et al., *J. Biol. Chem.* 268:14065-14070 (1993); Kreitman & Pastan, *Bioconjug. Chem.* 4:581-585 (1993); and Buchner et al., *Anal. Biochem.* 205:263-270 (1992)). Debinski et al., for example, describe the denaturation and reduction of inclusion body peptides in guanidine-DTE. The peptide is then refolded in a redox buffer containing oxidized glutathione and L-arginine.

The peptides described in this invention can be evaluated by screening techniques in suitable assays for the desired characteristic, e.g., promoting cell survival/plasticity or inhibiting/reducing cell death upon external assault. For instance, the peptides, as well as other compounds that modulate cell death/survival, described in the present invention can be screened by employing suitable assays described herein or known to those skilled in the art.

One of skill will recognize that modifications can be made to the polypeptides without diminishing their biological activity. Some modifications may be made to facilitate the cloning, expression, or intake of the polypeptide by the target cells or tissue. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

C. Modification of Peptides

In some cases it might be desirable to further modify the peptides of the present invention, for example, to increase the stability or bioavailability of the peptide. One example of such modification is acetylation of the peptides at a suitable site (e.g., the N-terminus of the peptide or the internal $NH_2$ group on a Lys residue). Acetylation can be achieved by chemical reaction or enzymatic reaction, both methods known in the art.

Other examples of peptide modification include glycosylation, PEGylation, lipidation, amidation, or addition of a tag sequence for ease of purification and subsequent handling. For instance, a peptide may be amidated at its C-terminus to form —CO—$NH_2$ (replacing the OH), especially in multiple natural peptides. Furthermore, it is possible to place an additional peptide tail to a peptide of this invention to improve certain desired characteristics, e.g., to increase permeability of the peptide.

D. Functional Assays of Peptides and Other Compounds with Anti-Apoptosis Activity The novel peptides and other compounds described herein are useful for the method of this invention due to their activity in promoting cell survival, or suppressing cell death upon exposure to cytotoxicity. Furthermore, the present invention allows for initial screening of additional compounds, which can be widely diverse in their chemical nature, as possible modulators of cell survival and cell death. Functional assays are performed to verify the biological activity of these peptides or other possible modulators.

A variety of cell culture-based methods are known in the art, as well as described in this application, for testing and demonstrating a compound's potential effects on cell survival. For instance, a cell viability assay using a suitable cell type (e.g., a cultured neuronal cell line such as PC12 cells) may be employed to compare the cell count, the rate of cell division, and/or the level of cell metabolism in the presence or absence of a potential modulator under test conditions (e.g., when cells are subject to treatment of a toxic agent such as Zinc at a harmful concentration). While a potential modulator of cell survival could have either positive or negative effects on the cells' susceptibility to cell death, when the presence of a compound leads to increased cell survival, the compound is deemed an inhibitor or suppressor of cell death; conversely, when the presence of a compound leads to decreased cell survival, the compound is deemed an enhancer of cell death.

E. Functional Assays for Compounds Promoting Cell Plasticity

The novel peptides and other compounds described herein are also useful for the method of this invention due to their activity in promoting, protecting, or increasing cell plasticity, especially neuronal plasticity or synaptic plasiticy. Furthermore, the present invention allows for initial screening of additional compounds, which can be widely diverse in their chemical nature, as possible modulators of cell plasticity. Functional assays are performed to verify the biological activity of these peptides or other possible modulators.

A variety of cell culture-based methods are known in the art, as well as described in this application, for testing and demonstrating a compound's potential effects on cell plasticity. For instance, a PSD-95 expression assay using primary cortical neuron cultures established from suitable animals may be performed to confirm a compound's activity in promoting cell plasticity. More specifically, primary cultures of neurons are prepared by first taking cerebral cortex tissue from newborn rats on postnatal day 1. The cerebral cortex tissue is then dissected and dissociated individually from each animal. Cells are fixed with ice cold methanol, blocked (e.g., with bovine serum albumin (BSA) and normal goat serum), and incubated with primary antibody (e.g., monoclonal antibody against PSD-95), optionally followed by the appropriate secondary antibody for imaging purposes. Images of primary neuronal cultures are taken and compared between cultures with or without being exposed to a test compound. An increased PSD-95 expression is indicative of the test compound being capable of promoting or protecting cell plasticity, especially neuronal plasticity.

II. Screening Methods for Identifying Modulators of Cell Survival or Plasticity

A. Screening Methods Based on Binding with EB Proteins

By illustrating the role of EB proteins during the cell death/survival or plasticity process, the present invention allows identification of modulators of cell susceptibility to apoptosis or cell plasticity by screening among candidate compounds for such potential modulators based on such compounds' physical interaction or binding with at least one of the EB proteins, e.g., a human or rodent version of an EB protein.

Various methods are known in the art for detecting binding between a known protein and potential "binders" of any chemical nature. Such methods are also described in detail in this application. For example, a candidate compound may be immobilized on a solid substrate, and a solution containing a suitable EB protein is incubated with the substrate under conditions that permit the binding between the EB protein and a potential "binder" molecule. After a proper washing step, the presence of the EB protein is then detected, e.g., by an antibody that specifically recognizes the EB protein, or by the presence of a detectable label previously conjugated to the EB protein. The binding of the EB protein and any given test compound would indicate the compound to be a potential modulator of cell death/cell survival. One example of such binding assay is the affinity chromatography described in the examples of this application. Chips containing a large, immobilized test compound library, e.g., protein arrays or proteomic chips, will be useful for this purpose. Typically, a positive control, such as a peptide known to bind to an EB protein (e.g., NAP peptide that is known to bind EB3 protein), as well as a negative control, such as a peptide known to not bind to EB proteins, are included in the screen assay to ensure accurate determination of binding between a candidate agent and an EB protein.

B. Screening Methods Based on Effects on Expression of EB Proteins

The present invention further provides for the screening of potential modulators of cell death/survival or cell plasticity from a large collection of molecules of any chemical nature based on a modulator's effects on the expression of an EB protein. Any such effect on EB protein expression may be detected and monitored at either mRNA level or protein level.

Similar to the EB protein binding assay format, candidate compounds may be screened as a first, preliminary step to quickly identify as potential modulators of cell death/survival or cell plasticity, which may then be subject to further testing for functional verification. In some cases, the effect on EB protein expression is tested in a cell-based assay system, where a suitable cell type (e.g., a neuronal cell) that endogenously expresses one or more EB proteins is exposed to a candidate compound under conditions that permits EB protein expression in the cells. The level of the EB protein and/or mRNA is then measured and compared between cell samples where the candidate compound is present or absent. When an increased expression of EB protein or mRNA is detected, the test compound is deemed a potential modulator that promotes cell survival or cell plasticity, or an inhibitor or suppressor of cell death. Conversely, if a decreased expression of EB protein or mRNA is detected, the test compound is deemed a potential modulator that increases cell susceptibility to cell death or inhibits cell plasticity, i.e., a promoter of cell death or inhibitor of cell plasticity.

Also similar to the EB protein binding assays described above, appropriate positive and negative controls are often used in the assays to ensure the proper operation of the experimental system. Finally, a preliminarily identified cell death/survival or plasticity modulator based on its effect on the expression of an EB protein is subject to functional verification using the functional assays described in the last section.

C. Functional Assays

The screening assays described above often serve as a useful tool to preliminarily identify, from a large pool of candidate compounds, possible modulators of cell survival or cell plasticity. To fully verify and more precisely determine the functional effects of these potential modulators, functional assays described in the last section are typically performed subsequent to the initial screening step.

III. Pharmaceutical Compositions and Administration

The pharmaceutical compositions comprising the modulators that promote cell survival or modulate cell plasticity as described in this application (e.g., a peptide having the amino acid sequence set forth in SEQ ID NO:2 or SEQ ID NO:5 or the 4-amino acid peptide SKIP, including the version with N-terminus acetylation or lipophilization and/or C-terminus amidation, as well as all D-amino acids, or any one of the compounds named in Table 4) are suitable for use in a variety of drug delivery systems. The polypeptides can be administered systemically, e.g., by injection (intravenous, subcutaneous, intradermal, or intramuscular), or by oral administration, or by nasal administration, or a local administration such as using a dermal patch, under the tongue pellet etc. The methods for various routes of delivery are well known to those of skill in the art.

Suitable formulations for use in the present invention are found in Remington's *Pharmaceutical Sciences* (17th ed. 1985)). For a brief review of methods for drug delivery, see Langer, *Science* 249:1527-1533 (1990). Suitable dose ranges are described in the examples provided herein, as well as in WO96/11948.

As such, the present invention provides for therapeutic compositions or medicaments comprising one or more of the polypeptides described hereinabove in combination with a pharmaceutically or physiologically acceptable excipient, wherein the amount of polypeptide is sufficient to provide a therapeutic effect, e.g., to improve the neurodegenerative condition a patient is receiving the treatment for.

In a therapeutic application, the modulators of the present invention are embodied in pharmaceutical compositions intended for administration by any effective means, including parenteral, topical, oral, nasal, pulmonary (e.g. by inhalation) or local administration. Nasal pumps/sprays, eye drops, and topical patches can be used.

The invention provides compositions for parenteral administration that comprise a solution of a modulator (e.g., a peptide comprising SKIP), as described above, dissolved or suspended in an acceptable carrier, such as an aqueous carrier. Parenteral administration can comprise, e.g., intravenous, subcutaneous, intradermal, intramuscular, or intranasal administration. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the modulators are preferably supplied in finely divided form along with a surfactant and propellant. Accordingly, in some embodiments, the pharmaceutical composition comprises a surfactant such as a lipophilic moiety to improve penetration or activity. Lipophilic moieties are known in the art and described, e.g., in U.S. Pat. No. 5,998,368. The surfactant must be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (see, e.g., Gozes et al., *J Mol Neurosci.* 19:167-70 (2002)).

In therapeutic applications, the modulators of the invention are administered to a patient in an amount sufficient to reduce or eliminate symptoms of a condition involving undesirable cell death, such as a neurodegenerative disorder. An amount adequate to accomplish this is defined as "therapeutically effective dose." Amounts effective for this use will depend on, for example, the particular peptide employed, the particular form of a pharmaceutical composition in which the peptide is present (e.g., a peptide of SEQ ID NO:2 or SKIP v. an acetylated peptide of SEQ ID NO:2 or SKIP), the type of disease or disorder to be treated and its severity, the manner of administration, the weight and general state of health of the patient, and the judgment of the prescribing physician.

For example, an amount of a cell survival or cell plasticity modulator, e.g., a peptide of SEQ ID NO:2 or SKIP or any one of the compounds listed in Table 4, falling within the range of a 100 ng to 30 mg dose given intranasally once a day would be a therapeutically effective amount. Alternatively, dosages may be outside of this range when on a different schedule (such as by injection or oral ingestion). For example, dosages can range from 0.0001 mg/kg to 10,000 mg/kg, and can be about 0.001 mg/kg, 0.1 mg/kg, 1 mg/kg, 5 mg/kg, 50 mg/kg or 500 mg/kg per dose. Doses may be administered hourly, every 4, 6 or 12 hours, with meals, daily, every 2, 3, 4, 5, 6, or 7 days, weekly, every 2, 3, 4 weeks, monthly or every 2, 3 or 4 months, or any combination thereof. The duration of dosing may be single (acute) dosing, or over the course of days, weeks, months, or years, depending on the condition to be treated. Those skilled in the art can determine the suitable dosage and administration frequency depending on the particular circumstances of individual patients.

EXAMPLES

The following examples are provided by way of illustration only and not by way of limitation. Those of skill in the art will readily recognize a variety of non-critical parameters that could be changed or modified to yield essentially the same or similar results.

Example 1: Microtubule End Binding (EB) Proteins—the Neuroprotective/Neurotrophic NAP (Davunetide) Target Introduction The plus ends of growing MTs accumulate a diverse group of MT-associated proteins, collectively referred to as the plus-end-tracking proteins (+TIPs). +TIPs encompass a large number of unrelated proteins, motor and nonmotor proteins, regulatory proteins, and adaptor proteins. One +TIP binding protein family is the end-binding (EB) protein family. Like other +TIPs, EB proteins mediate interactions between the ends of MTs, organelles, and protein complexes as well as altering MT stability. EB3 is preferentially expressed in the CNS and is used to track MT dynamics (E. S. Sweet et al., *J Neurosci* 31, 1038 (Jan. 19, 2011)). EB3 further interacts with post synaptic density protein, PSD-95 at the level of the dendritic modeling and plasticity (E. S. Sweet et al., *J Neurosci* 31, 1038 (Jan. 19, 2011)). Thus, EB3 plus-end decorate MTs, control actin dynamics and regulate spine morphology and synaptic plasticity, through interaction with PSD-95, and NMDA receptor activation (L. C. Kapitein et al., *J Neurosci* 31, 8194 (Jun. 1, 2011)). EB1 was shown to interact with a conserved binding site in +TIPS—namely, SxIP (S. Honnappa et al., *Cell* 138, 366 (Jul. 23, 2009)). Similarly, it was recently shown that plexins membrane proteins associated with neurite growth interact with the three EB proteins with a SxIP (SGIP) motif (P. Laht, K. Pill, E. Haller, A. Veske, *Biochim Biophys Acta*, (Feb. 21, 2012)). Unlike EB1, EB3 shows specificity to the nervous system. On the other hand, it has been reported that EB3 and EB1 heterodymerize to form a dimer, and EB proteins exhibit intricate control on each other (e.g., www.ncbi.nlm.nih.gov/pubmed/19255245). As such, EB1 may be required for the biological activity of EB1/EB3 dimer.

The EB protein family is an evolutionarily conserved family of proteins, which in mammals are encoded by the MAPRE gene family and include EB1, EB2 (RPI) and EB3 (J. P. Juwana et al., *Int J Cancer* 81, 275 (Apr. 12, 1999); L. K. Su, Y. Qi, *Genomics* 71, 142 (Jan. 15, 2001)). In animal cells, EB proteins may constitute the "core" of the plus end complex because they interact directly with most other known TIPs including dynactin large subunit p150Glued, APC, CLASPs, spectraplakins, RhoGEF2, and a catastrophe-inducing kinesin KLP10A (J. M. Askham, K. T. Vaughan, H. V. Goodson, E. E. Morrison, *Mol Biol Cell* 13, 3627 (October, 2002); W. Bu, L. K. Su, *The Journal of biological chemistry* 278, 49721 (Dec. 12, 2003); L. A. Ligon, S. S. Shelly, M. Tokito, E. L. Holzbaur, *Mol Biol Cell* 14, 1405 (April, 2003); S. L. Rogers, U. Wiedemann, U. Hacker, C. Turck, R. D. Vale, *Curr Biol* 14, 1827 (Oct. 26, 2004); S. Honnappa, C. M. John, D. Kostrewa, F. K. Winkler, M. O. Steinmetz, *EMBO J* 24, 261 (Jan. 26, 2005); V. Mennella et al., *Nat Cell Biol* 7, 235 (March, 2005); Y. Mimori-Kiyosue et al., *The Journal of cell biology* 168, 141 (Jan. 3, 2005); K. C. Slep et al., *The Journal of cell biology* 168, 587 (Feb. 14, 2005)). EB1 was initially identified in a yeast two hybrid screen as a protein that interacts with the C-terminus of the adenomatous polyposis coli (APC) tumor suppressor protein, EB1 is also a specific marker of growing MT tips (L. K. Su et al., *Cancer research* 55, 2972 (Jul. 15, 1995)). RNA interference mediated deletion of EB1 from cells leads to an increase time that a MT spends pausing and EB1 also increases rescue frequency as well as reduces catastrophe frequency and depolymerization rates. EB1 protein links MT to actin protrusion and cell polarity through signaling pathways involving PKC (J. M. Schober, G. Kwon, D. Jayne, J. M. Cain, *Biochemical and biophysical research communications* 417, 67 (Jan. 6, 2012)). Overall, EB1 recently emerged as a master regulator of dynamic +TIP interaction networks at growing MT ends (S. Honnappa, C. M. John, D. Kostrewa, F. K. Winkler, M. O. Steinmetz, *EMBO J* 24, 261 (Jan. 26, 2005); N. Galjart, F. Perez, *Curr Opin Cell Biol* 15, 48 (February, 2003); S. Honnappa et al., *Mol Cell* 23, 663 (Sep. 1, 2006)). The EB proteins are often small globular dimers that contain two highly conserved domains that are connected by a linker sequence. The N-terminal part of the EB protein consists of a calponin homology (CH) domain, which is necessary and sufficient for binding to MTs and recognizing growing MT ends (Y. Komarova et al., *The Journal of cell biology* 184, 691 (Mar. 9, 2009)). The second domain is a coiled coil region, which determines their dimerization (S. Honnappa, C. M. John, D. Kostrewa, F. K. Winkler, M. O. Steinmetz, *EMBO J* 24, 261 (Jan. 26, 2005); K. C. Slep et al., *The Journal of cell biology* 168, 587 (Feb. 14, 2005)). EB3 is a homologue of EB1 and shares a 54% identity to EB1. EB3 is especially abundant in the central nervous system, where it binds to APC2/APCL, the brain specific form of APC, and it is expressed to lesser degree in muscles (A. Straube, A. Merdes, *Curr Biol* 17, 1318 (Aug. 7, 2007); H. Nakagawa et al., *Oncogene* 19, 210 (Jan. 13, 2000)). EB3-depleted cells show disorganized MT and fail to stabilize polarized membrane protrusions. EB3 is necessary for the regulation of MT dynamics and MT capture at the cell cortex (A. Straube, A. Merdes, *Curr Biol* 17, 1318 (Aug. 7, 2007)). Drebrin, an F-actin-associated protein, binds directly to EB3. In growth cones, this interaction occurs specifically when drebrin is located on F-actin in the proximal region of filopodia and when EB3 is located at the tips of MT invading filopodia. When this interaction is disrupted, the formation of growth cones and the extension of neurites are impaired. Drebrin targets EB3 to coordinate F-acting MT interactions that underlie neuritogenesis (S. Geraldo, U. K. Khanzada, M. Parsons, J. K. Chilton, P. R. Gordon-Weeks, *Nat Cell Biol* 10, 1181 (October, 2008)). EB3 is a major regulator of spine plasticity by influencing actin dynamics within the dendritic spine. EB3 binds directly to p140Cap, which is localized at the postsynaptic density and is an inhibitor of Src tyrosine kinases (J. Jaworski et al., *Neuron* 61, 85 (Jan. 15, 2009)). All mammalian EB proteins are very similar in structure, but it appears that EB2 is the most divergent family member showing differences in expression, as well as interactions with MTs and binding partners (E. E. Morrison, *Cell Mol Life Sci* 64, 307 (February, 2007)). Protein depletion and rescue experiments showed that EB1 and EB3, but not EB2, promote persistent MT growth by suppressing catastrophes (Y. Komarova et al., *Mol Biol Cell* 16, 5334 (November, 2005)). Where investigated, it appears that interactions identified for EB1 can be replicated by EB3 but not EB2. It was shown that CLIP-170 and a closely related protein CLIP-115 bind directly to EB1 and EB3 while displaying a lower affinity for EB2. This interaction depends on the C terminal tails of the EB proteins, which are strikingly similar to those of alpha tubulin (Y. Komarova et al., *Mol Biol Cell* 16, 5334 (November, 2005)). EB1 and EB3 increase the number of neurites in PC12 cells while EB2 blocks neurite elongation (V. Laketa, J. C. Simpson, S. Bechtel, S. Wiemann, R. Pepperkok, *Mol Biol Cell* 18, 242 (January, 2007)). EB1 preferentially heterodimerizes with EB3, while, EB2 does not seem to form heterotypic complexes. Heterotypic complex formation between EB1 and EB3, thus, generates an additional EB variant which is expected to display yet a different functional profile when compared with its homotypic counterparts. These findings also suggest that EBs are not present in separate pools but, rather, form a common pool undergoing continuous exchange within the cytoplasm. A consequence of this consideration is that in cells that co-express different EB species, their functions cannot be contemplated and analyzed separately from each other (C. O. De Groot et al., *The Journal of biological chemistry* 285, 5802 (Feb. 19, 2010)).

EB proteins bind to multiple partners and until now two major binding modes have been described: through the association of a linear SxIP motif with the hydrophobic cavity of the EBs and through the binding of CAP-Gly domains to the C-terminal EEY motif of the EBs. Using live cell imaging experiments and in vitro reconstitution assays, it was demonstrated that a short polypeptide motif, Ser-x-Ile-Pro (SxIP), is used by numerous +TIPs, including APC, CLASPs (CLIP associating proteins), MCAK (mitotic centromere associated kinesin), TIP150, MACF (MT-actin crosslinking factor), STIM1 (stromal interaction molecule 1), p140Cap, Navigators, melanophilin, RhoGEF2, CDK5RAP2 and DDA3, for localization to MT tips in an EB1-dependent manner. Highly conserved C-terminal domain of EB1 recognizes this short linear sequence motif found in a large number of important +TIPs for MT plus-end tracking. The most prominent contacts involve Ser5477, Ile5479, and Pro5480, which occupy the positions 1, 3, and 4 of the SxIP motif (S. Honnappa et al., *Cell* 138, 366 (Jul. 23, 2009)). A recent report showed that the serine residues around the SxIP motifs of CLASP2 are phosphorylated by GSK3f3, disrupting MT plus end tracking (P. Kumar et al., *The Journal of cell biology* 184, 895 (Mar. 23, 2009)). These data support the view that phosphorylation in the vicinity of SxIP motifs negatively regulates the localization of +TIPs to MT ends by decreasing their affinity to EB1 (S. Honnappa et al., *Cell* 138, 366 (Jul. 23, 2009)).

Given the: (1) structural similarities between the different EB proteins and the lately found plexin binding to EBs, (2) the fact that the SIP motif is required for NAP activity (M. F. Wilkemeyer et al., *Proc Natl Acad Sci USA* 100, 8543 (Jul. 8, 2003)), (3) the fact that the SIP motif is also found in activity-dependent neuroprotective factor (ADNF)—SALL-RSIPA (M. Bassan et al., *J Neurochem* 72, 1283 (March, 1999)), (P. Laht, K. Pill, E. Haller, A. Veske, *Biochim Biophys Acta*, (Feb. 21, 2012)) that NAP (as well as SALL-RSIPA) have a preferential neuroprotection/neurotrophic activity (I. Gozes et al., *J Mol Neurosci* 20, 315 (2003); I. Gozes, I. Spivak-Pohis, *Curr Alzheimer Res* 3, 197 (July, 2006)), and interact with MTs (M. Holtser-Cochav, I. Divinski, I. Gozes, *J Mol Neurosci* 28, 303 (2006)), the present inventors hypothesized that NAP (NAPVSIPQ) interacts with EB3. Given the fact that EB3 can form dimers with EB1, and interaction with EB1 is also envisaged. EB2 blocks neurite elongation (V. Laketa, J. C. Simpson, S. Bechtel, S. Wiemann, R. Pepperkok, *Mol Biol Cell* 18, 242 (January, 2007)) and hence—if associated with NAP activity, the manner of interaction is different.

As eluded to above, NAP has been previously shown to protect against MT breakdown and tubulin aggregation in the presence of toxic concentration of zinc that were associated with neuronal and glial death (I. Divinski, M. Holtser-Cochav, I. Vulih-Schultzman, R. A. Steingart, I. Gozes, *J Neurochem* 98, 973 (August, 2006); I. Divinski, L. Mittelman, I. Gozes, *J Biol Chem* 279, 28531 (Jul. 2, 2004)).

Materials and Methods
Bioinformatics—Pattern Search:
http://www.genome.jp/tools/motif/
http://wwvv.algosome.com/resources/human-proteome/motif-pattern-matcher.html
http://pir.georgetown.edu/pirwww/search/pattern.shtml#
http://prosite.expasy.org/cgi-bin/prosite/PSScan.cgi
http://bioware.ucd.ie/~compass/cgi-bin/formParser.py
Cell Culture Systems
P19 Cells Mouse embryonic teratocarcinoma cells (P19 cells) were obtained from the American Type Culture Collection (ATCC, Bethesda, Md., USA); an initial control batch was a kind gift of Dr. Roi Atlas and the late Prof. Irith Ginzburg from the Weizmann Institute of Science, Rehovot, Israel. P19 cells were grown in minimal essential medium (alpha-MEM, Biological Industries, Beit Haemek, Israel) containing 5% fetal calf serum, 100 U/ml penicillin and 0.1 mg/ml streptomycin (Biological Industries) in a 5% $CO_2$ incubator at 37° C.

Neuronal or Cardiomyocyte Induced P19 Differentiation

For induction of differentiation, $1 \times 10^6$ P19 cells were cultured in 90 mm bacteriological grade dishes with their usual growth medium and supplemented with 1 µM all-trans retinoic acid (RA, Sigma, St. Louis, Mo., USA) to induce neuronal and astroglial differentiation (E. M. Jones-Villeneuve, M. W. McBurney, K. A. Rogers, V. I. Kalnins, *J Cell Biol* 94, 253 (August, 1982)) or 0.8% dimethylsulfoxide (DMSO, Sigma) to induce cardiac and skeletal muscle differentiation, as previously described (A. Habara-Ohkubo, *Cell Struct Funct* 21, 101 (April, 1996); I. S. Skerjanc, *Trends Cardiovasc Med* 9, 139 (July, 1999); M. A. van der Heyden, L. H. Defize, *Cardiovasc Res* 58, 292 (May 1, 2003); Mandel et al., *J. Mol. Neurosci.* 35:127, 2008). Four days later, cell aggregates were suspended with trypsin-C (Biological Industries) and transferred to poly-L-lysine (Sigma) coated tissue culture dishes. The cells were grown in RA/DMSO-free Dulbecco's modified Eagle's medium (DMEM) containing 2.5% fetal calf serum, 4 mM L-glutamine and antibiotics (Biological Industries) for additional four days to induce neuronal and astroglial or cardiac and skeletal muscle phenotype. As controls to the differentiated conditions, both non-differentiated cells as well as cells that went through the differentiation process in the absence of the inducer were evaluated.

Rat Cerebral Cortical Astrocyte Cell Cultures

Newborn rats (Harlan, Jerusalem, Israel) were sacrificed by decapitation, and the brain was removed (D. E. Brenneman et al., *J Pharmacol Exp Ther* 309, 1190 (June, 2004)). The tissue was minced with scissors and placed in Hank's balanced salts solution 1 (S1), containing HBSS (Biological Industries, Beit Haemek, Israel), 15 mM HEPES buffer, pH 7.3 (Biological Industries, Beit Haemek, Israel), and 0.25% trypsin (Biological Industries) in an incubator at 37° C. 5% $CO_2$ for 20 min. The cells were then placed in 5 mL of solution 2 (S2) containing 10% heat inactivated fetal serum (Biological Industries), 0.1% gentamycin sulphate solution (Biological Industries), and 0.1% penicillin-streptomycin-nystatin solution (Biological Industries) in Dulbecco's modified Eagle's medium (DMEM, Sigma, Rehovot, Israel). The cells were allowed to settle and are then transferred to a new tube containing 2.5 mL of S2 and triturated using a Pasteur pipette. Cell density was determined using a hemocytometer (Neubauer Improved, Germany) and $15 \times 10^6$ cells/15 mL S2 are inoculated into each 75-$cm^2$ flask (Corning, Corning, N.Y., USA). Cells are incubated at 37° C. 10% $CO_2$. The medium was changed after 24 h, and cells are grown until confluent.

Rat Cerebral Cortical Astrocyte Cell Subcultures

The flasks were shaken to dislodge residual neurons and oligodendrocytes that may be present. Flasks were then washed with 10 mL cold HBSS×1, HEPES 15 mM. 5 mL of versene-trypsin solution (BioLab, Jerusalem, Israel) were added to each flask, and the flasks are incubated at room temperature for 5 min to remove astrocytes. The flasks were shaken to dislodge the cells. The versenetrypsin solution was neutralized with 5 mL of S2. The cell suspension was collected and centrifuged at 100 g for 10 min. The supernatant was removed and the cells resuspended in S2. Cells were inoculated into 75-cm² flasks or plated in 35-mm dishes (Corning, Corning, N.Y., USA) and incubated until confluence at 37° C. 10% $CO_2$.

Primary Neuronal Cultures

Cerebral cortex tissue from newborn rats was dissected and dissociated individually from each pup with the Papain Dissociation System (PDS), (Worthington Biochemical Corporation) according to the manufacturer's instructions. Cortical neurons were maintained in Neurobasal medium (NB), (Gibco) supplemented with NeuroCult B27-SM1 (STEM-CELL), 1% Glutamax (Gibco), and grown on poly-D-lysine-coated cell culture glass cover slips. The cells were incubated in 5% $CO_2$ in a humidified incubator at 37° C.

PC12 Cells

PC12 cells (Pheochromocytoma cells) (ATCC, Bethesda, Md., USA) were seeded at 3×104 cells/cm² on poly-L-Lysine coated plastic tissue culture dishes (Corning, Lowell, Mass., USA) to form an adherent monolayer. Cells were maintained in Dulbecco's modified Eagle's medium (DMEM) supplemented with 10% horse serum (HS), 5% fetal calf serum (FCS), 2 mM glutamine, 100 U/ml penicillin and 100 mg/ml streptomycin (Biological Industries, Beit Haemek, Israel). PC12 differentiation was induced by nerve growth factor (NGF, Sigma) at concentrations of 50 ng/ml by replacing half of the medium every other day until the cells acquired a differentiated morphology. Differentiated cells were defined as bearing two or more neurites with lengths equal to or more than twice the diameter of the cell body (P. Lamoureux et al., *The Journal of cell biology* 110, 71 (January, 1990)). The cells were incubated in 5% $CO_2$ in a humidified incubator at 37° C. The cells were sub-cultured every 5 days at a 4:1 split ratio by pipetting. The medium was changed every 2 or 3 days after adhesion.

NIH3T3 Cells

NIH3T3 (mouse fibroblasts) (ATCC, Bethesda, Md., USA) were cultured in DMEM containing 10% heat inactivated fetal calf serum, 2 mM L-Glutamine, 100 units/mL penicillin, and 0.1 mg/mL streptomycin (Biological Industries) in 5% $CO_2$ at 37° C. (growth conditions). Every 3-4 days cells were split using trypsin-EDTA solution B (Biological Industries).

Immunostaining

Cultured cells plated on glass coverslips were fixed and permeabilized simultaneously, with 3% paraformaldehyde, 0.075% glutaraldehyde (Fluka Biochemika) in MT-buffer (80 mM PIPES pH 6.8, 1 mM $MgCl_2$, 2 mM EGTA, 5% Glycerol) with 0.5% TritonX-100, for 10 min, quenched with 1 mg/ml $NaBH_4$ in PBS, blocked with 2% BSA and 5% normal goat serum in TBS-T (20 mM Tris pH 7.5, 136.8 mM NaCl, and 0.05% v/v Tween 20), and incubated with primary antibodies followed by the appropriate secondary antibodies. Nuclei were visualized with Hoechst dye.

Confocal Microscopy and Image Analysis

Images were collected with a Leica SP5 confocal laser scanning microscope (Mannheim, Germany) with 63× oil immersion optics, laser lines at 488, 561, 633 nm or with LSM 510 META (Zeiss, Jena, Germany) confocal laser scanning microscope with 63× oil immersion optics, laser lines at 488, 568, 633 nm. When comparing fluorescence intensities, identical CLSM parameters (e.g., scanning line, laser light, gain, and offset etc.) were used. All of the fluorescent signals acquired were above the autofluorescent background as measured from a control slide stained with secondary antibody without a primary antibody. To compare the relative levels of protein expression, the average integrated density (AID) image analysis procedure was used for cell immunostains. In brief, integrated density is defined by the sum of the values of the pixels in the selected region of interest (ROI). This is equivalent to the product of Area and Mean Gray Value. AID for the positive stained area was determined by measuring the fluorescent intensity of the ROI, which is above the positive cut-off intensity. Positive cut-off intensities were determined based on the fluorescence intensities histogram for each antibody staining. For measurements of the MT containing area in a given cell, the chosen focal plane was the one showing the maximal area on the z-axis (focal axis). Analysis was done using the MICA software (Cytoview, Petach Tikva, Israel) and ImageJ (NIH, Bethesda, Md., USA).

Peptides

Peptides were purchased form Hy-Labs (Rehovot Israel). All peptides were dissolved in double distilled water to a concentration of 1 mM and then diluted in water in 1:10 steps up to the required concentration.

List of Peptides:

| Short name | Sequence |
|---|---|
| NAP/SIP | NAPVSIPQ |
| SKIP | NAPVSKIPQ |
| SAIP | NAPVSAIPQ |
| AAAA | NAPVAAAAQ |
| SRIP | NAPVSRIPQ |
| TRIP | NAPVTRIPQ |
| Ac-SKIP | Acetyl-NAPVSKIPQ-$NH_2$ |
| SKIP1 | SKIP |
| SGIP | SGIP |
| NAPVSGIP | NAPVSGIP |

Antibodies and Other Cell Staining Molecules
Primary Antibody List:

Monoclonal anti-βIII-tubulin antibody (T8578, Sigma, Rehovot, Israel), monoclonal anti Tyr-α-tubulin antibody (YL1/2) (VMA1864, Abcys, Paris, France), polyclonal anti Glu-α-tubulin antibody (L4) (AbC0101, Abcys, Paris, France), monoclonal anti-tau (tau-5) (ab80579, Abcam, Mass., USA), monoclonal anti-tau (tau-5) (Biosource International, Camarillo, Calif., USA), monoclonal anti-total tau (AT-5004, MBL, Billerica, Mass., USA), monoclonal [TAU-5] anti tau (ab80579, Abcam), polyclonal anti MAPRE3 (ab13859, ab99287, Abcam), monoclonal anti PSD-95 (ab-2723, Abcam), anti actin (ab1801, Abcam, Mass., USA), monoclonal anti α-tubulin (DM1A) (T6199, Sigma, Rehovot, Israel).

Other Tracers:

Sulfonated DiI: DiIC18(5)-DS/5 mg (D12730, Invitrogen, NY, USA), a lipophilic tracer: long-chain dialkylcarbocyanines, DiI, is used as anterograde and retrograde neuronal tracer in living (M. G. Honig, R. I. Hume, *The Journal of cell biology* 103, 171 (July, 1986); M. G. Honig, R. I. Hume, *Trends in neurosciences* 12, 333 (September, 1989)) and fixed (G. E. Baker, B. E. Reese, *Methods Cell Biol* 38, 325 (1993); P. Godement, J. Vanselow, S. Thanos, F. Bonhoeffer, *Development* 101, 697 (December, 1987)) tissues and cells. DiI labeling does not appreciably affect cell viability, development, or basic physiological properties. The dye uniformly labels neurons via lateral diffusion in the plasma membrane. Coumarin Phalloidin (P2495, Sigma-Aldrich) was used to label actin.

Secondary Antibodies:

The secondary antibodies used were Peroxidase AffiniPure Goat anti-mouse (Jackson ImmunoResearch, Suffolk, UK), Cy3-conjugated Goat Anti-Rat IgG, Cy5-conjugated goat anti-rabbit IgG, Rhodamine Red-X-AffiniPure Fab Fragment Goat Anti-Rabbit IgG (Jackson ImmunoResearch). DyLight 488-labeled secondary goat anti-mouse IgG, DyLight 633-labeled secondary goat anti-rabbit IgG (KPL, Gaithersburg, Md., USA).

Gene Knockdown—RNA Interference and Transfection siRNA Oligos

Double-stranded RNA can initiate post transcriptional gene silencing in mammalian cell cultures via a mechanism known as RNA interference (RNAi). The sequence-specific degradation of homologous mRNA is triggered by 21-nucleotide RNA-duplexes termed short interfering RNA (siRNA). The homologous strand of the siRNA guides a multi-protein complex, RNA-induced silencing complex (RISC), to cleave target mRNA. The siRNA against rat MAPRE3 (NM_001007656) was obtained as an On-Target plus smart pool L-099082-01-0005-0010 (Dharmacon, Thermo Fisher Scientific, Lafayette, Colo., USA). Dharmacon ON-TARGETplus Non-targeting siRNA (D-001810-01-05) was used as a negative control. To control transfection efficiency, a control siRNA Dharmacon siGLO RISC-free siRNA (D-001600-01-05), was used.

Transfection

Transfections were performed using Lipofectamine RNAiMAX (Invitrogen). Transfection was carried out according to manufacturer's protocol. For rat MAPRE3 knockdown, PC12 cells or neurons were plated in growth medium without antibiotics at concentration of $10^4$ cells/$0.32$ cm$^2$ such that they will be 30-50% confluent at the time of transfection. To obtain the highest transfection efficiency and low non-specific effects, siRNA transfection was performed in the following optimized conditions: 50 nM for neurons and 25 nM PC12 of each siRNA construct with 0.2 µl Lipofectamine RNAiMAX (Invitrogen) was added per well of the 96-well plate and scaled up for different 24 or 6-well plates, according to the manufacturer's instructions. The medium was changed one day after transfection. 48 and 72 hours later, cells were harvested to assay for gene knockdown at the RNA and protein levels.

Zinc Toxicity

On the day of the experiment, the growth medium was aspirated and fresh medium containing $ZnCl_2$ (400 µM; Sigma, Rehovot, Israel) with or without NAP was added to the cells. The cells were incubated for 4 hrs at 37° C. 5% $CO_2$. Survival was measured using the MTS assay.

Cell Viability Assay—Metabolic Activity Measurements

Metabolic activity of cells was measured by the CellTiter 96® Aqueous Non-Radioactive Cell Proliferation kit in accordance with the manufacturer's instructions (Promega). The assay uses a colorimetric method for determining the number of viable cells employing a tetrazolium compound [3-(4,5-dimethylthiazol-2-yl)-5-(3-carboxymethoxyphenyl)-2-(4-sulfophenyl)-2H-tetrazolium, MTS] and an electron-coupling reagent, phenazine methosulfate (PMS). MTS is bio-reduced by cells into a formazan product that is detected at 490 nm. The conversion of MTS into the formazan form is accomplished by dehydrogenase enzymes found in metabolically active cells. Thus, the quantity of formazan product as measured by the amount of 490 nm absorbance is directly proportional to the number of living cells in culture (A. H. Cory, T. C. Owen, J. A. Barltrop, J. G. Cory, *Cancer Commun* 3, 207 (July, 1991)).

RNA Extraction

Total RNA from cells was extracted using the RNeasy Plus Mini Kit (Qiagen, Hilden, Germany) according to the manufacturer's protocol. Briefly, cells were lysed and homogenized and genomic DNA was removed using gDNA Eliminator column. After genomic DNA removal, RNA was purified using RNeasy spin columns. A 10 µl aliquot was taken from each sample to examine the RNA content and quality, as indicated below. The rest of the samples were stored for further examination at −80° C.

RNA integrity was determined by fractionation on 1% agarose gel and staining with ethidium bromide (Sigma). Two bands indicating 18S and 28S ribosomal RNA subunits should appear, while a smear without evidence for the two ribosomal RNA bands is indicative for RNA degradation. RNA quantity and quality were analyzed by the Nanodrop ND-1000 UV-Vis spectrophotometer (NanoDrop Technologies, Wilmington, Del., USA). Each sample measurement was performed in duplicates.

Reverse Transcription and Quantitative Real-Time Polymerase Chain Reaction (PCR)

Samples containing equal amount of total RNA were used to synthesize single-strand cDNA using SuperScript III Reverse Transcriptase (RT, Invitrogen) or High Capacity cDNA Reverse Transcription Kit (Applied Biosystems), with random hexamers according to the manufacturer's instructions. In each RT-PCR run, two negative controls were included: sterile water without RNA to rule out contamination in the reaction components and total RNA without the RT enzyme to test for genomic contamination. Real-Time polymerase chain reaction (PCR) was performed using the SYBR® Green PCR Master Mix or Fast SYBR® Green PCR Master Mix and ABI PRISM 7900 or ABI StepOnePlus Sequence Detection Systems instrument and software (Applied Biosystems) accordingly using the default thermocycler program for all genes: 10 minutes of pre-incubation at 95° C. followed by 40 cycles of 15 seconds at 95° C. and 1 minute at 60° C. The comparative Ct method was used for quantification of transcripts. In short, the method compares the Ct value of target gene to a housekeeping gene in a single sample. Because it takes several cycles for enough products to be readily detectable, the plot of fluorescence versus cycle number exhibits a sigmoidal appearance. At later cycles, the reaction substrates become depleted, PCR product no longer doubles, and the curve begins to flatten. The point on the curve in which the amount of fluorescence begins to increase rapidly, usually a few standard deviations above the baseline, is termed the threshold cycle (Ct value).

Real-Time PCR reactions were carried out in a total volume of 15 µl in a 96-well plate (Applied Biosystems) containing 7.5 µl of X2 SYBR® Green PCR Master Mix and ~233 nM of each sense and antisense primers; for the reactions carried out with the StepOnePlus system the volume in each well, the type of plate and Master Mix were adjusted accordingly. Efficiencies of all primers used were calculated as a precursory step using the standard curve method, according to the equation: E (efficiency)=[10(−1/slope)−1]×100 and were near 100% for all primers. Product specificity was confirmed routinely by melting curve analysis. Sequence comparisons were performed with the BLAST software (www.ncbi.hlm.nih.gov/BLAST/).

Relative Quantitation (RQ)

Relative Quantitation (RQ) of gene expression using Comparative CT (ΔΔCt) determines the change in expression of a nucleic acid sequence (target, EB3) in a test sample (treated cells) relative to the same sequence in a calibrator sample (untreated control) (K. J. Livak, T. D. Schmittgen, *Methods* 25, 402 (December, 2001)). Fold-expression changes are calculated using the equation $2^{-\Delta\Delta C_T}$. Relative quantities of the targets are normalized against the relative quantities of the endogenous control (HPRT1). Gene Expression plots show the expression level or fold-difference of the target sample relative to the calibrator. Because the calibrator is compared to itself, the expression level for the calibrator is always 1.

Relative Standard Curve Method

This method requires the least amount of validation because the PCR efficiencies of the target and endogenous control do not have to be equivalent. This method requires that each reaction plate contain standard curves. This approach gives highly accurate quantitative results because unknown sample quantitative values are interpolated from the standard curve(s). The relative standard curve method was used to determine relative target (EB3) quantity in samples. With the relative standard curve method, the software measures amplification of the target (EB3) and of the endogenous control (HPRT1) in samples, in a reference sample, and in a standard dilution series. Measurements are normalized using the endogenous control. Data from the standard dilution series are used to generate the standard curve. Using the standard curve, the software interpolates target quantity in the samples and in the reference sample. The software determines the relative quantity of target in each sample by comparing target quantity in each sample to target quantity in the reference sample.

Primers

Primer pairs (Table 1) were designed using the primer 3 web interface (http://frodo.wi.mit.edu/primer3/) or by using the NCBI primer designing tool (http://www.ncbi.nlm.nih.gov/tools/primer-blast/) and synthesized by Sigma-Genosys. To avoid amplification of contaminating genomic DNA, primers for quantitative real time PCR were designed to target exon-exon junction.

RNA expression levels were normalized to mouse/rat HPRT1 (hypoxanthine-guanine phosphoribosyltransferase) as endogenous control.

TABLE 1

Quantitative Real-Time PCR: primer pairs

| Primer | Sequence |
|---|---|
| Mouse MAPRE1 (NM_007896) | 5'-GCGTTGACAAAATAATTCCT-3' <br> 5'-TGGCAGCTACAGGATCATAC-3' |
| Mouse MAPRE2 (NM_001162941) | 5'-ATACAGCTCAACGAGCAGGTACAT-3' <br> 5'-CAGCAGCTCAATCTCTCTCAACTTC-3' |
| Mouse MAPRE3 (NM_133350) | 5'-GCTGTGTTCACTTGAGGAAG-3' <br> 5'-GAATGATTTTGTCAACACCC-3' |
| Mouse HPRT1 (NM_013556) | 5'-GGATTTGAATCACGTTTGTGTC-3' <br> 5'-CAGGACTCCTCGTATTTGCAG-3' |
| Rat MAPRE1 (NM_138509) | 5'-GAAGAAAGTGAAATTCCAGG-3' <br> 5'-AGGAATTATTTTGTCAACGC-3' |
| Rat MAPRE2 (NM_001101000) | 5'-GGGCGTTTCCAAGACAACCT-3' <br> 5'-CTTGTCGAGCCTCAACAGGAT-3' |
| Rat MAPRE3 (NM_001007656) | 5'-GGACAAAATCATTCCCGTAG-3' <br> 5'-GGTTGTAATCCTTTCCATCA-3' |
| Rat HPRT1 (NM_012583) | 5'-AGGCCAGACTITGTTGGATT-3' <br> 5'-GCTTTTCCACTTTCGCTGAT-3' |

Protein Extraction and Quantification

Total protein (cytoplasmic and nuclear fractions) extraction was performed from cells grown in 6 well culture plates using modified RIPA lysis buffer. Cell pellet was collected by centrifugation (300 g, 5 min, RT), washed twice in ice-cold PBS and subjected to lysis in modified RIPA buffer (50 mM Tris-HCl pH 7.4, 150 mM NaCl, 2 mM EGTA, 1% Triton X-100, 0.1% SDS, 0.1% sodium Deoxycholate) supplemented with protease inhibitor cocktail (Sigma) and 5 mM ethylenediaminetetraacetic acid (EDTA). Cells in modified RIPA buffer (50-150 µl/well) were gently disrupted, using a pipette, and then rotated for 20 min at 4° C. at 600 angle. The resulting homogenate was centrifuged (16,000 g, 15 min, 4° C.), and the supernatant was then collected in aliquots and stored at −80° C. Proteins were quantified using the BCA™ Protein Assay Kit (Pierce, Rockford, Ill., USA). This method is based on the reduction of $Cu^{2+}$ to $Cu^{1+}$ by protein in an alkaline medium (the biuret reaction), that is coupled to the colorimetric detection of the cuprous cation ($Cu^{1+}$) by using a reagent containing bicinchoninic acid (BCA). The purple-colored reaction product of this assay is formed by the chelation of two molecules of BCA with one cuprous ion. The resulting water-soluble complex exhibits a strong absorbance at 562 nm that is nearly linear with increasing protein concentrations over a protein range of 20 µg/ml to 2000 µg/ml (P. K. Smith et al., *Anal Biochem* 150, 76 (October, 1985); K. J. Wiechelman, R. D. Braun, J. D. Fitzpatrick, *Anal Biochem* 175, 231 (Nov. 15, 1988)).

Immunoblotting

For western blot analysis, sample buffer X5 (125 mM Tris-HCl pH 6.8, 25% β-mercaptoethanol (Sigma), 43.5% glycerol, 10% SDS, 0.05% bromophenol blue) was added to protein samples that were further denatured by boiling at 100° C. for 5 minutes. ~10-20 µg protein extract per lane was separated by electrophoresis on a 10% (w/v) polyacrylamide gel (BioRad, Hercules, Calif., USA) containing 0.1% SDS or 4-20% precast iGels (NuSep, Bogart, Ga., USA). Molecular weights were determined using Precision Plus Protein Standards (10-250 kD, Dual Color, BioRad). Following electrophoresis, proteins were transferred to nitrocellulose membrane (Whatman plc, Kent, UK) and nonspecific antigen sites were blocked using a solution containing 5% non-fat dried milk (w/v) in TBST (10 mM Tris pH 8, 150 mM NaCl, and 0.05% Tween 20) for 1 hour at room temperature. Antigen detection was performed over-night at 4° C. using appropriate antibodies. Antibody-antigen complexes were detected using horseradish peroxidase (HRP)

conjugated goat anti-mouse or anti-rabbit IgG secondary antibodies (Jackson ImmunoResearch, West Grove, Pa., USA) and visualized by the Pierce ECL Western Blotting Substrate kit (Pierce) on Kodak Biomax ML Scientific imaging film (Kodak, Chalon-sur-Saône, France). The densitometric analysis of western blots was performed with MiniBIS Pro Gel imaging system and software (DNR, Mahale HaHamisha, Israel).

Recombinant EB3 Production

Recombinant EB3 was prepared as previously described (S. Honnappa et al., Cell 138, 366 (Jul. 23, 2009)). Full-length human EB3 was subcloned into pEX-N-His vector (PrecisionShuttle bacterial expression vector with N-terminal His tag CW300309, OriGene, Rockville, Md., USA). Competent E. coli BL21(DE3) were transformed with the vector on LB agar plates containing 30 mg/ml kanamycin and 100 mg/ml chloramphenicol. Affinity purification of the N-terminal 6×His-tagged fusion proteins by immobilized metal affinity chromatography on $Ni^{2+}$-Sepharose (Amersham) was performed at 4° C. according to the manufacturer's instructions. The 6×His fusion-tag was removed from recombinant proteins and peptides by thrombin (Sigma) cleavage. Protein and peptide samples were gel filtered on a Superdex-75 column (Amersham) equilibrated in 20 mM Tris-HCl (pH 7.5), supplemented with 75 mM NaCl.

Sulfolink Coupling Gel-NAP Affinity Chromatography

The affinity chromatography column included Sulfo-Link® Immobilization Kit for Peptides (44999, Thermo Scientific, Rockford, Ill., USA). Binding of CKKKG-GNAPVSIPQ was performed according to the manufacturers' instruction. Recombinant protein was loaded (2 mg/mL) on the columns (2 mL) and incubated overnight at 4° C.; the columns were then washed with phosphate-buffered saline until all unbound protein was eluted [as confirmed by protein assay (Bradford; Bio-Rad Laboratories, Mannheim, Germany)]. NAP-binding proteins were eluted in IgG Elution buffer (pH 2.8) (Thermo scientific). In order to show specificity, binding was inhibited with either NAP or control peptides. Sodium dodecyl sulfate-polyacrylamide gel electrophoresis (SDS-PAGE) was then performed followed by western blot analysis in order to detect the protein (R. Zamostiano et al., J Biol Chem 276, 708 (Jan. 5, 2001)).

Statistical Analysis

Results were analyzed for statistical significance between two groups by Student's t-test and for multiple comparisons by one way analysis of variance (ANOVA). Data are presented as the mean±SEM from at least 3 independent experiments performed in triplicates in western blot analysis and at least 3 independent experiments in duplicates or more in confocal studies. Statistical analysis of the data was performed by using one-way ANOVA with Dunnett's post-test using GraphPad Prism version 5.00 (GraphPad Software, San Diego Calif. USA, www.graphpad.com), * $P<0.05$,  $P<0.01$, * $P<0.001$.

Results

The EB Binding Groove, a Potential Bioinformatics Tool for Drug Design:

As stated above, EB1 was shown to interact with a conserved binding site in +TIPs—namely, SxIP. Using live cell experiments and in vitro reconstitution assays, it was demonstrated that a short polypeptide motif, Ser-x-Ile-Pro (SxIP), is used by numerous +TIPs, including the tumor suppressor APC, the transmembrane protein STIM1, and the kinesin MCAK, for localization to MT tips in an EB1-dependent manner. Highly conserved C-terminal domain of EB1 recognizes this short linear sequence motif found in a large number of important +TIPs for MT plus-end tracking. The most prominent contacts involve Ser, Ile, and Pro, which occupy the positions 1, 3, and 4 of the SxIP motif (S. Honnappa et al., Cell 138, 366 (Jul. 23, 2009)).

The protein sequences of EB1, 2, and 3 were compared by multiple sequence alignment in order to assess the EB1 binding motif SxIP for EB2 and EB3. The binding domain is conserved in rat, human and mouse, between the EBs. EB3 is slightly more similar to EB1 than EB2 to EB1. The main (SxIP) motif interacting residues are highly conserved between EB1, EB2, EB3, (FIG. 3, yellow rectangle), while the other residues involved in the cavity which are likely to have interaction with the other residues of the binding peptide, are less conserved (FIG. 3, red rectangle). This analysis indicates an extensive homology in the SxIP binding groove between the EB's, suggesting it may be also be a binding motif for EB2, and EB3. The differences between the sequences may explain the specificity of SxIP motif containing proteins with their EB partner (FIG. 3).

TABLE 2

(part I). SxIP motif containing proteins involved in NAP activity via interaction with EB3; additional + TIPS; and other proteins of interest

| Gene Name | Name | UniProt Accession # | Function | Motif |
|---|---|---|---|---|
| SRCN1 | SRC kinase signaling inhibitor 1/SNAP-25-interacting protein/p130Cas-associated protein/p140Cap | Q9C0H9 | Acts as a negative regulator of SRC. Regulates dendritic spine morphology. Involved in calcium-dependent exocytosis. May play a role in neurotransmitter release or synapse maintenance. Binds EB3 | SIP |
| APC2 | Adenomatous polyposis coli protein 2/Adenomatous polyposis coli protein-like | O95996 | Brain-specific adenomatous polyposis coli homologue. Promotes rapid degradation of CTNNB1 and may function as a tumor suppressor. May function in Wnt signaling. Binds EB3. | SSIP |
| APC | Adenomatous polyposis coli protein | P25054 | Tumor suppressor. Participates in Wnt signaling as a negative regulator. Acts as a mediator of ERBB2-dependent stabilization of microtubules at the cell cortex. It is required for the localization of | SQIP |

TABLE 2-continued

| | | | | |
|---|---|---|---|---|
| MACF1 | Microtubule-actin cross-linking factor 1 | Q9UPN3 | MACF1 to the cell membrane and this localization of MACF1 is critical for its function in microtubule stabilization. F-actin-binding protein which may play a role in cross-linking actin to other cytoskeletal proteins and also binds to microtubules. Plays an important role in ERBB2-dependent stabilization of microtubules at the cell cortex. Acts as a positive regulator of Wnt receptor signaling pathway and is involved in the translocation of AXIN1 and its associated complex (composed of APC, CTNNB1 and GSK3B) from the cytoplasm to the cell membrane. Has actin-regulated ATPase activity and is essential for controlling focal adhesions (FAs) assembly and dynamics. | SKIP |
| NAV1 | Neuron navigator 1 | Q8NEY1 | Associates with a subset of microtubule plus ends. Enriched in neuronal growth cones. May be involved in neuronal migration. | SGIP |
| NAV2 | Neuron navigator 2 | Q8IVL1 | Possesses 3' to 5' helicase activity and exonuclease activity. Involved in neuronal development, specifically in the development of different sensory organs. | SFIP |
| NAV3 | Neuron navigator 3 | Q8IVL0 | May regulate IL2 production by T-cells. May be involved in neuron regeneration. Highly expressed in brain. | SGIP |

(part II). Additional + TIPS:

| SxIP + TIPS | Partners | SXIP sequence | Function | Reference |
|---|---|---|---|---|
| Plexin B1 | EB1 | SGIP | Neurite outgrowth | Laht et al., BBA 2012 |
| Plexin B3 | EB1, EB2, EB3 | SGIP | Neurite outgrowth | Laht et al., BBA 2012 |
| hsMACF2 (microtubule actin crosslinking factor)? Similar to ACF7? The SxIP sequence not the same | EB1 | SKIP | | |
| ACF7 | EB1, CLASP 1, CLASP 2 | | Peripheral microtubule outgrowth & stabilization | Mimori-Kiyosue JCB 2001; Zaoui et al, PNAS 2010. |
| CLASP1 | EB1, CLIP-170, CLIP-115, ACF7 | | Stabilization | Mimori-Kiyosue JCB 2005 |
| CLASP2 | EB1, CLIP-170, CLIP-115, ACF7 | SKIP & SRIP | Rescue | Mimori-Kiyosue JCB 2005 |
| hsAPC (adenomatous polyposis coli) | BE1, MCAK | SQIP | Cell polarity and tumorigenesis | Barth et al., *Semin Cell Dev Biol.* 2008 |
| hsSTIM1 (stromal interacting molecule) | EB1 | TRIP | ER remodeling | Grigoriev et al., Curr Biol, 2008 |
| P140Cap | EB3 | | Regulator of Src tyrosine kinase. EB3 regulates spine size by modulating the turnover of | Jaworski et al., Neuron 2009 |

TABLE 2-continued

| | | | p140Cap in spines. | |
|---|---|---|---|---|
| MCAK (KIF2c) | EB1, Tip 150 | SKIP | MT depolymerase | Tanenbaum et al., BioArchi, 2011 |
| Tip150 | EB1, MCAK | ? | Targets MCAK to MT | Jiang et al., EMBO 2009 |
| Navigators | EB1, EB2, EB3 | ? | MT severing, MT transport and cytoskeleton organization | Maes et al., Genomics, 2002 |
| Melanophilin | EB1 | SGIP | Mitotic spindle positioning | Wu et al., JCB 2005 |
| CDK5RAP2 | EB1 | ? | CDK5RAP2-EB1 complex induces microtubule assembly | Fong et al Mol Biol Cell 2009 |
| RhoGEF2 (Dm) | EB1 | ? | GTP/GDP exchange, regulate dynamics | Rogers et al., Curr Biol 2004 |
| DDA (hs) aka PSRC1 proline/serine-rich coiled-coil 1 | EB1, EB3 | SAIP | Recruit Kif2a to the mitotic spindle and spindle poles--depolymerizing | Jang et al., JCB 2008; Hsieh et al., Oncogene 2007. |

| (part III). Other proteins of interest: | | | | |
|---|---|---|---|---|
| Gene Name | Name | UniProt Accession # | Function | Motif |
| MAP1S | Microtubule-associated protein 1S/ Microtubule-associated protein 8 | Q66K74 | Microtubule-associated protein that mediates aggregation of mitochondria resulting in cell death and genomic destruction (MAGD). Plays a role in anchoring the microtubule-organizing center to the centrosomes. | SSIP |
| MAP1LC3A | Microtubule-associated proteins 1A/1B light chain 3A | Q9H492 | Probably involved in formation of autophagosomal vacuoles (autophago somes). | SKIP |
| MAP1A | Microtubule-associated protein 1A | P78559 | Structural protein involved in the filamentous cross-bridging between microtubules and other skeletal elements. | SKIP |

EB Expression Aligns with NAP Activity:

Reverse transcription and quantitative real time PCR analysis of mRNA expression in rat non-differentiated PC12 cells, differentiated PC12 cells treated with NGF and primary cultures of cortical astrocytes and neurons grown for 4 days in vitro (DIV) or 19DIV showed that EB3 is highly enriched in cortical neurons. RNA silencing of EB3 in PC12 cells and primary neuronal cultures compared to cells treated with non-targeting siRNA resulted in up to 50% mRNA expression inhibition of EB3 with no effect on the other EB's (FIG. 4a). Further analysis of mouse cell lines, showed that EB3 is preferentially expressed in mouse P19 cells subjected to neuro-glia differentiation by retinoic acid (RA) compared to non-differentiated or cardiac and skeletal muscle differentiated P19 cells (DMSO). The mouse fibroblast line NIH3T3 also did not show preferential expression of EB3 (FIG. 4b). These results indicate that NAP-responsive cells (I. Gozes et al., *J Mol Neurosci* 20, 315 (2003); I. Divinski, M. Holtser-Cochav, I. Vulih-Schultzman, R. A. Steingart, I. Gozes, *J Neurochem* 98, 973 (August, 2006)) preferentially express EB3, while cells that do not respond to NAP treatment like NIH3T3 (I. Gozes et al., *J Mol Neurosci* 20, 315 (2003); I. Divinski, M. Holtser-Cochav, I. Vulih-Schultzman, R. A. Steingart, I. Gozes, *J Neurochem* 98, 973 (August, 2006)) express EB3 in a low basal non preferential way compared to EB1 and EB2, which are ubiquitously expressed.

Figure 5:
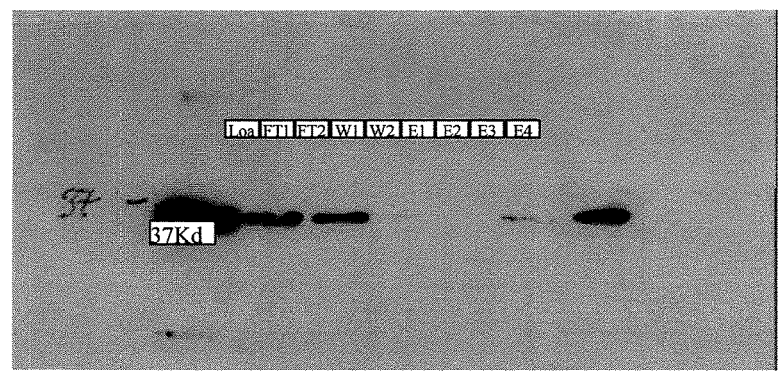
FIG. 5: EB3 binds to NAP. NAP was bound to sulfolink coupling resin and recombinant EB3 (37 Kd) was loaded on the resulting affinity column. Proteins were separated by electrophoresis SDS-PAGE followed western analysis. The figure shows the western results. Column loading material-recombinant EB3 (Load), the column flow through (FT1 and FT2), the column wash (W1 and W2) and the eluted material (E1-4). Each lane was loaded with 40 µl of sample (including sample buffer): Load=~11.5 µg, FT1=~3.1 µg, FT2=~1 µg, W1=~0 µg, W2=~0 µg, E2=~9 µg. Protein concentration was estimated as indicated in the methods section. EB3 was identified by specific antibodies.
Figure 6:
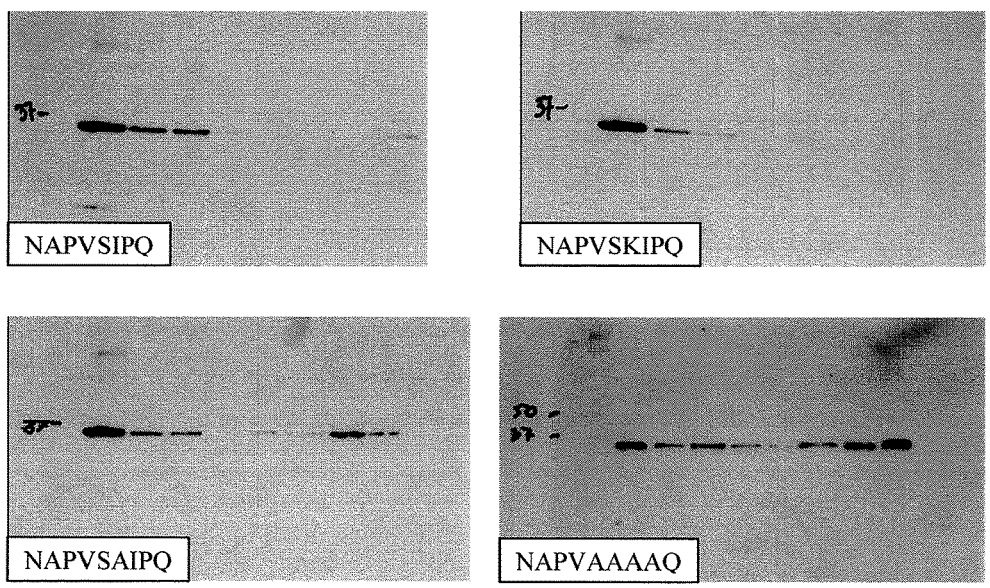
FIG. 6: EB3 binds SIP and SKIP containing sequences. NAP was bound to sulfolink coupling gel and full length human EB3 recombinant protein together with competing peptides were loaded on the resulting affinity column. The figure shows the western analysis results. Column loading material-recombinant EB3+indicated peptide (Load), the column flow through (FT1 and FT2), the column wash (W1 and W2) and the eluted material (E1-3). EB3 was identified by specific antibodies. Left lane was loaded with protein marker (m). The table lists the sample volume and estimated protein amount loaded on each lane of the protein separation gels.

NAP-EB3 Binding on Column Chromatography:

The inventors previous studies showed that NAP interacts with brain/neuron-glia specific tubulin (M. Holtser-Cochav, I. Divinski, I. Gozes, *J Mol Neurosci* 28, 303 (2006); I. Divinski, L. Mittelman, I. Gozes, *J Biol Chem* 279, 28531 (Jul. 2, 2004)). As indicated above, other findings suggested that the SIP moiety in NAPVSIPQ is essential for its activity (M. F. Wilkemeyer et al., *Proc Natl Acad Sci USA* 100, 8543 (Jul. 8, 2003)). This current experiment was set out to expand these previous findings and to further explore NAP protein binding targets, aiming toward a better understanding on NAP mechanisms as an active peptide. As EB3 is highly enriched in neurons and binds to MT, and EB1 was shown to interact with other +TIPs through the binding motif SxIP (Honnappa et al., *Cell* 138, 366 (Jul. 23, 2009)) and comparative sequence analysis showed that EB3 sequence shares high similarity with the SxIP motif binding cavity in EB1 as also verified by Laht et al., (P. Laht, K. Pill, E. Haller, A. Veske, *Biochim Biophys Acta*, (Feb. 21, 2012)), these experiments investigated if EB3 is a NAP binding protein. Full-length human EB3 recombinant protein was produced and NAP interaction with the recombinant EB3 protein was tested using the column chromatography method (I. Divinski, L. Mittelman, I. Gozes, *J Biol Chem* 279, 28531 (Jul. 2, 2004)). 2 mg of recombinant full-length human EB3 were exposed to 2 mg NAP sequences (CKK-KGGNAPVSIPQ) covalently bound to sulfolink coupling gel. Column load, flow through, wash and elution fractions were further analyzed by polyacrylamide gel electrophoresis, followed by western analysis with EB3 antibodies. FIG. 5 shows the western results, indicating that NAP associates with EB3. Further column specificity was shown by competition with NAPVSIPQ/EB3-mimetic peptides. Thus, the affinity column beads were incubated with recombinant EB3 and 2 mg of either: i] soluble NAPVSIPQ (as positive control, which should displace all binding); ii] NAPVSKIPQ (representing an EB3-binding, NAP mimetic); iii] NAPVSAIPQ, a negative control—which does not contain the EB3-binding signature, and iv] NAPVAAAAQ, a negative control—which does not contain any of the EB3-binding signature. Column chromatography, elution and western blots were performed as above. The extract fractions (flow, wash and elution) were separated by electrophoresis followed by protein detection (FIG. 6). Competition with NAPVSIPQ or NAPVSKIPQ showed no binding of EB3 to the column bound NAP (no EB3 in the eluted material). On the other hand, no competition was apparent with NAPVSAIPQ or NAPVAAAAQ, EB3 was bound to NAP and acid-eluted. In order to verify that EB3 was indeed eluted from the column, beads were taken from the column resin mixed with sample buffer and western blot analysis was performed (FIG. 6—"NAPVAAAAQ" most right lane). No EB3 immunoreactivity was observed suggesting there was no EB3 protein binding non-specifically to the resin itself. These findings suggest EB3 to be NAP direct binding target protein through the SxIP binding motif.
Binding to Cellular Proteins to NAP (Affinity Chromatography with Brain Extracts)

Affinity chromatography was carried out as above with rat brain extracts as before (34, 36). However, several additional experiments were undertaken and mass spectrometry was employed to identify additional potential NAP-interacting proteins that elute from the affinity column.

Results:

The experiment was repeated twice (including mass spectrometry) and the results showed specific interaction of NAP with drebrin, that could be associated with the NAP-EB interaction, as drebrin binds directly to EB3, see, e.g., Geraldo et al., *Nature Cell Biology* 10:1181-1189, 2008. Additional proteins that have been shown to bind NAP or D-SAL are listed in Table 3.

TABLE 3

Comparison between binding proteins of NAP and AL-309 (all D-amino acids SALLRSIPA - D-SAL), (D. E. Brenneman et al., *J Pharmacol Exp Ther* 309, 1190 (June, 2004)) on the respective affinity columns (two independent experiments):

| | NAP1 | D-SAL |
|---|---|---|
| Molecular Weight: ~55,000 KD | tubulin, beta 2 tubulin, alpha 3c | tubulin, beta [*Mus musculus*] TubB2, B2c, B3, B5 tubulin, alpha 1B TubA1, A1C |
| ~100 KD | **drebrin 1 [*Rattus norvegicus*]** | |

Specific NAP-binding (or D-SAL) is depicted in bold. Shared NAP and D-SAL binding are indicated.

Drebrin 1 [*Rattus norvegicus*]:

drebrin, located in the dendritic spines of the neuron, plays a role in the synaptic plasticity together with actin filaments. Drebrin regulates the morphological changes of spines. It has been observed to be significantly reduced in the brains of Alzheimer's and Down syndrome patients (K. S. Shim, G. Lubec, *Neurosci Lett* 324, 209 (May 24, 2002)), and has been reported to play a role during neuritogenesis through its binding with EB3 (Geraldo et al., *Nature Cell Biology* 10:1181-1189, 2008).

Figure 8:
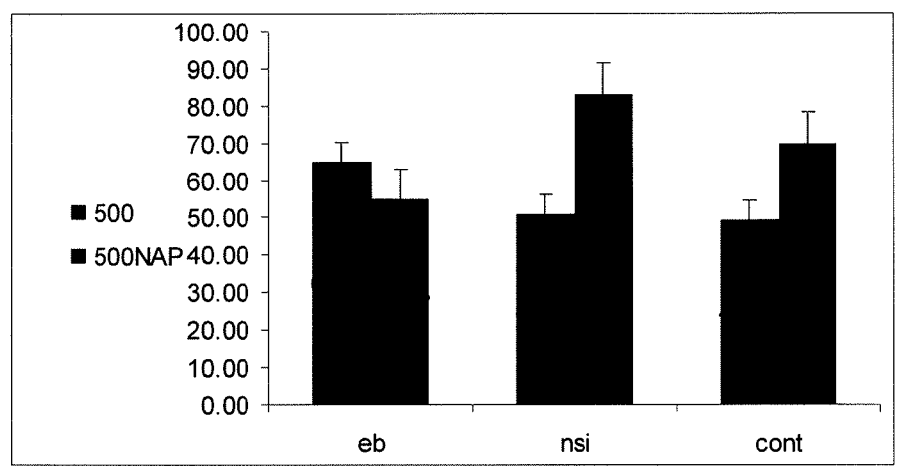
FIG. 8: Zinc treatment (500 microM) resulted in PC12 cell death which was protected against by NAP treatment ($10^{-15}$M). Several controls were used one included non-specific siRNA (nci), one (no treatment, cont), and one RNA silencing of EB3 (eb). Results of mitochondrial activity (MTS), (I. Divinski, M. Holtser-Cochav, I. Vulih-Schultzman, R. A. Steingart, I. Gozes, *J Neurochem* 98, 973 (August, 2006)) are shown—100—is 100% survival—control (n=8 for each experimental point). ANOVA—P<0.001.

NAP Protection Against Zinc Toxicity is Dependent on EB3:

NAP has been previously shown to protect against MT breakdown and tubulin aggregation in the presence of toxic concentration of zinc that were associated with neuronal (Divinski et al., *Neurochem* 98, 973 (August, 2006)) and in glial cells death (Divinski et al., *J Biol Chem* 279, 28531 (Jul. 2, 2004)). Here, in a pheochromocytoma (PC12) cell survival assay, PC12 cells were exposed to increasing zinc concentration for 4 hrs. Significant cell death was observed at zinc concentration >200 μM (data not shown), corroborating previously published data that established the EC50 for zinc cell killing effect at 308±38 μM (Sanchez-Martin et al., *Brain Res Bull* 81, 458 (Mar. 16, 2010)). The inventors chose to work with zinc concentrations that gave consistent and significant cell death, i.e., 400 μM zinc. NAP treatment at concentrations of $10^{-15}$M and $10^{-9}$M showed a significant protection effect against cell death induced by zinc toxicity (FIG. 7a). Further evaluation of the derivative peptides at concentration of $10^{-9}$M in the presence of 400 μM zinc, showed that NAPVSKIPQ (denoted SKIP on the figure) and Acetyl-NAPVSKIPQ-NH$_2$ (denoted Ac-SKIP on the figure) provided protection against zinc toxicity, mimicking NAP activity (FIG. 7a). NAPVSRIPQ and NAPVTRIPQ, which were used as controls (denoted SRIP and TRIP on the figure) were inactive (FIG. 7b). FIG. 8 shows that NAPVSIPQ does not protect against zinc intoxication, when EB3 is silenced.

NAP Effects MT in Dendritic Protrusions in Primary Neuronal Cells:

Most excitatory synapses in the mammalian brain are formed at tiny dendritic protrusions, termed dendritic spines. A dendritic spine is a small, club-like cell protrusion from neuronal dendrites that form the postsynaptic component. Dynamic changes in spine structure are known to occur during normal brain development, and are likely to contribute to synaptic plasticity underlying processes such as learning and memory. These cell protrusions play a critical role in synaptic transmission and plasticity (K. Huang, A. El-Husseini, *Curr Opin Neurobiol* 15, 527 (October, 2005)). MTs, long thought to be absent from dendritic spines until very recently, are capable of controlling spine morphology (J. Jaworski et al., *Neuron* 61, 85 (Jan. 15, 2009)), contributing to the synaptic plasticity at the dendritic spine level (J. Jaworski et al., *Neuron* 61, 85 (Jan. 15, 2009); J. Gu, B. L. Firestein, J. Q. Zheng, *J Neurosci* 28, 12120 (Nov. 12, 2008); C. C. Hoogenraad, F. Bradke, *Trends in cell biology* 19, 669 (December, 2009); X. Hu, C. Viesselmann, S. Nam, E. Merriam, E. W. Dent, *J Neurosci* 28, 13094 (Dec. 3, 2008); P. Penzes, D. P. Srivastava, K. M. Woolfrey, *Neuron* 61, 3 (Jan. 15, 2009)). The cytoskeleton of dendritic spines is particularly important in their synaptic plasticity; without a dynamic cytoskeleton, spines would be unable to rapidly change their volumes or shapes in responses to stimuli. The cytoskeleton of dendritic spines is primarily made of filamentous actin (F-actin). Spiny dendritic protrusions can be classified on the basis of spine lifetime and motility into one of three categories: filopodia, protospines, or spines (M. E. Dailey, S. J. Smith, *The Journal of neuroscience: the official journal of the Society for Neuroscience* 16, 2983 (May 1, 1996)). Mature dendritic spines are formed from dynamic spine precursors (filopodia and protospines) that become stabilized, or occasionally by direct extension from the dendrite shaft. The conversion of filopodia to protospines coincides with the formation of a postsynaptic density (PSD) containing PSD-95 (G. S. Marrs, S. H. Green, M. E. Dailey, *Nat Neurosci* 4, 1006 (October, 2001); L. Qin, G. S. Marrs, R. McKim, M. E. Dailey, *J Comp Neurol* 440, 284 (Nov. 19, 2001)). Location of post synaptic density proteins change in relation to spine type and maturation, conversion of filopodia to spines involves assembly of a core PSD scaffold (time-course: ~0.5-2 hr) and PSDs in developing spines (proto-spines) are highly dynamic: they can rapidly appear or disappear, as well as grow, shrink, move and possibly split and merge (G. S. Marrs, S. H. Green, M. E. Dailey, *Nat Neurosci* 4, 1006 (October, 2001); L. Qin, G. S. Marrs, R. McKim, M. E. Dailey, *J Comp Neurol* 440, 284 (Nov. 19, 2001); G. S. Mans et al., *Mol Cell Neurosci* 32, 230 (July, 2006); S. J. Schachtele, J. Losh, M. E. Dailey, S. H. Green, *J Comp Neurol* 519, 3327 (Nov. 1, 2011)). Here, we asked whether both dynamic (tyrosinated—Tyr-MT) and stable (de-tyrosinated, Glu-MT) MTs can be found in dendritic protrusions. PSD-95 was used as a marker for mature dendritic spines. Neurons were exposed to NAP for 2 hrs. Using advanced techniques in confocal microscopy, both Tyr-MT and Glu-MT were shown to be present in dendritic protrusions either in the presence of or in the absence of NAP (FIG. 9).

The inventors' recent findings suggest NAP control of the tubulin tyrosination cycle (Oz and Gozes, 2012, JBC, invited revision). Hence, the fact that dynamic MT and stable MTs are found in the dendritic protrusions suggests potential involvement in spine dynamics.

NAP Effect on PSD-95 Density in Primary Cortical Neuron Culture is EB3-Dependent:

Increased neuronal activity enhances both the number of spines invaded by MTs and the time that the MTs spend in the spines. EB3 knockdown significantly reduced the number of spines in cultured hippocampal neurons (X. Hu, C. Viesselmann, S. Nam, E. Merriam, E. W. Dent, *J Neurosci* 28, 13094 (Dec. 3, 2008)). Aβ oligomers, the hallmark of Alzheimer's disease, bind to synaptic sites (P. N. Lacor et al., *The Journal of neuroscience: the official journal of the Society for Neuroscience* 24, 10191 (Nov. 10, 2004)) and reduce the density of spines in organotypic hippocampal slice cultures (H. Hsieh et al., *Neuron* 52, 831 (Dec. 7, 2006); G. M. Shankar et al., *The Journal of neuroscience: the official journal of the Society for Neuroscience* 27, 2866 (Mar. 14, 2007); B. R. Shrestha et al., *Mol Cell Neurosci* 33, 274 (November, 2006); W. Wei et al., *Nat Neurosci* 13, 190 (February, 2010)), dissociated cultured neurons (B. Calabrese et al., *Mol Cell Neurosci* 35, 183 (June, 2007); N. A. Evans et al., *J Neurosci Methods* 175, 96 (Oct. 30, 2008); P. N. Lacor et al., *The Journal of neuroscience: the official journal of the Society for Neuroscience* 27, 796 (Jan. 24, 2007)) and transgenic mouse models (T. A. Lanz, D. B. Carter, K. M. Merchant, *Neurobiology of disease* 13, 246 (August, 2003); J. S. Jacobsen et al., *Proceedings of the National Academy of Sciences of the United States of America* 103, 5161 (Mar. 28, 2006); T. L. Spires et al., *The Journal of neuroscience: the official journal of the Society for Neuroscience* 25, 7278 (Aug. 3, 2005)). Given the previously observed effect of NAP on neurite outgrowth (M. Pascual, C. Guerri, *J Neurochem* 103, 557 (October, 2007); S. Chen, M. E. Charness, *Proc Natl Acad Sci USA*, (Dec. 1, 2008); W. A. Lagreze et al., *Invest Ophthalmol Vis Sci* 46, 933 (March, 2005); V. L. Smith-Swintosky, I. Gozes, D. E. Brenneman, M. R. D'Andrea, C. R. Plata-Salaman, *J Mol Neurosci* 25, 225 (2005)), the MT involvement in dendritic spine formation (J. Jaworski et al., *Neuron* 61, 85 (Jan. 15, 2009); J. Gu, B. L. Firestein, J. Q. Zheng, *J Neurosci* 28, 12120 (Nov. 12, 2008); C. C. Hoogenraad, F. Bradke, *Trends in cell biology* 19, 669 (December, 2009); X. Hu, C. Viesselmann, S. Nam, E. Merriam, E. W. Dent, *J Neurosci* 28, 13094 (Dec. 3, 2008); P. Penzes, D. P. Srivastava, K. M. Woolfrey, *Neuron* 61, 3 (Jan. 15, 2009)), the inventors questioned if NAP affects dendritic spine density in primary cortical neurons. To measure dendritic spine density, the post synaptic density protein, PSD-95, was used. The presence of PSD-95 clusters in excitatory neurons is well correlated with the number of mature dendritic spines (V. A. Alvarez, B. L. Sabatini, *Annual review of neuroscience* 30, 79 (2007); M. J. Kennedy, M. D. Ehlers, *Annual review of neuroscience* 29, 325 (2006)). Neurons were exposed to increasing concentrations of NAP for 2 hours. Results (FIG. 10a,b) indicate a NAP effect on the density of PSD-95, with respect to the control, in a bell-shaped dose response curve with a high significant effect at a concentration range of $10^{-15}M$-$10^{-6}M$ NAP. The observed effect, reached a peak value of 50% over control at a NAP concentration of 10-12M (FIG. 10b). Peptides derived from hybrids of NAPVSIPQ and +TIPs binding motifs that contain SxIP also possess neurotrophic and neuroprotective activity as follows below. Three novel peptides were tested in addition to NAP as outlined in FIG. 10c.

Results showed activity for NAPVSKIPQ that was paralleled to NAPVSIPQ activity. Importantly, NAPVSAIPQ and NAPVAAAAQ, which did not replace EB3-NAPVSIPQ binding (FIG. 6), did not enhance PSD-95 staining. The affinity chromatography results showed association of NAP with EB3. A recent manuscript has shown EB3 interaction with PSD-95 at the level of the dendritic modeling and plasticity (E. S. Sweet et al., *J Neurosci* 31, 1038 (Jan. 19, 2011)). Thus, EB3 plus-end decorated MTs control actin dynamics and regulate spine morphology and synaptic plasticity, through interaction with PSD-95, and NMDA receptor activation (L. C. Kapitein et al., *J Neurosci* 31, 8194 (Jun. 1, 2011)). Here the inventors show for the first time that silencing EB3 mRNA abolished NAP activity, implicating EB3 in the NAP-related neurotrophic effects (FIG. 10d).

Similar findings were also seen below (FIG. 11): NAP enhances PSD-95 expression in dendrites. Neuronal cultures were grown as above and stained with monoclonal anti-PSD-95) developed by DyLight 488-labeled secondary goat anti-mouse IgG and counter stained with the nuclear stain—DAPI.

Discussion

Cooperation of Binding Proteins at the MT +TIPS:

Honnappa et al. (S. Honnappa et al., *Cell* 138, 366 (Jul. 23, 2009)) showed that the affinity of individual +TIP-EB1 interactions is rather weak (low micromolar range). Their data demonstrate that multiple SxIP motifs, either within the same polypeptide chain or within different polypeptide chains, cooperate to increase the EB-dependent targeting efficiency.

EB-Drebrin-NAP:

The present inventors' original affinity column results (above) have suggested NAP-drebrin interaction. Drebrin is one of the major F-actin-binding proteins in neurons. Two isoforms of drebrin, E and A, are found in mammals, with drebrin A being the form specifically expressed in neurons. The biological functions of drebrin A have been reported in various publications, see, e.g., Kobayashi et al., *J Comp Neurol* 503(5):618, 2007; Bazellieres et al., *J Cell Sci* Advance Online Publication Jan. 24, 2012; Mizui et al., *J Neurochem* 109(2):611, 2009.

Specificity of Interaction:

Besides the NAP-like peptides described above that do not interact with EB3, other peptides that have been assayed include the results below (FIG. 14, inactive NAPVSIAQ (P7A) and NAPVAIPQ (S5A)). Importantly, when tested on astrocytes that have shown MT reorganization after NAP application (2 and 4 hours (I. Divinski, L. Mittelman, I. Gozes, *J Biol Chem* 279, 28531 (Jul. 2, 2004)), the addition of NAPVSIAQ did not mimic NAP activity on MT organization after 4 hours of incubation (FIG. 14).

Tubulin Tyrosination and the Association with EB:

Recent findings by the present inventors suggest NAP control of the tubulin tyrosination cycle (Oz and Gozes (2012) *The ADNP Derived Peptide, NAP Modulates the Tubulin Pool: Implication for Neurotrophic and Neuroprotective Activities* (Translated from eng) PLoS One 7(12): e51458). Hence, the fact that dynamic MT and stable MTs are found in the dendritic protrusions suggests potential involvement in spine dynamics. Tubulin tyrosination is associated with +TIP binding to microtubules (Weisbrich et al., *Nature Structure & Molecular Biology* 14:959, 2007). Indeed, NAP affected spine dynamics as measured at the level of PSD-95, showing increase in PSD-95 puncta after 2 hr incubation. The conversion of filopodia to protospines coincides with the formation of a core postsynaptic density (PSD) which—contains PSD-95 (time-course: ~0.5-2 hr). PSDs in proto-spines are highly dynamic: they can rapidly appear or disappear, as well as grow, shrink, move and possibly split and merge. The location of post synaptic density proteins changes in relation to spine type and maturation. See, e.g., Marrs et al., *Nature Neuroscience* 2001. 4(10): p. 1006, 2001; Qin et al., *The Journal of Comparative Neurology* 440(3):284, 2001; Marrs et al., *Molecular and Cellular Neurosciences* 32(3):230, 2006; and Schachtele et al., *The Journal of Comparative Neurology* 519(16): 3327, 2011. Interestingly, NAP effects on the puncta have been shown throughout the cell, similar in other systems, not associated with NAP treatment, e.g., Sweet et al. (*J Neurosci* 31:1038, 2011), together suggesting that SD-95 alters microtubule dynamics via an association with EB3.

Example 2: A New, Active 4-Amino Acid Peptide SKIP (SEQ ID NO:6)

I. In Vitro Protection
Methods
Cells

Rat pheochromocytoma cell (PC12, ATCC, Bethesda, Md., USA) were grown in 10-cm tissue culture dishes (Corning). The base medium for this cell line was RPMI-1640 Medium (Invitrogen) supplemented with 10% heat-inactivated horse serum, 5% fetal bovine serum and solution containing 100 U/ml penicillin together with 100 mg/ml streptomycin (Biological Industries, Beit Haemek, Israel). The cells were incubated in 95% air; 5% CO2 in a humidified incubator at 37° C. The medium was changed every 2 to 3 days. The cells were subcultured when cell density reached $4 \times 10^6$ cells/ml. The cells were split in a ratio of 1:4.

Zinc Intoxication

On the day before the experiment cells were to be harvested, re-suspended and seeded on tissue culture dishes. For cell viability measurements, cells were seeded on Poly-D-Lysine coated 96-well tissue culture dishes (Sigma-Aldrich) at a concentration of $3 \times 10^4$ cells/well.

Cell Viability Measurements

The cell viability is measured by colorimetric method that determines the number of viable cells in culture. This method is based on the bio-reduction of the tetrazolium compound [3-(4,5-dimethylthiazol-2-yl)-5-(3-carboxymethoxyphenyl)-2-(4-sulfophenyl)-2H-tetrazolium; MTS] by living cells into a colored formazan product. This reaction is occurring in the presence of an electron coupling reagent (phenazine ethosulfate; PES). The amount of formazan product is measured by ELISA plate reader at 490 nm and is directly proportional to the number of living cells in culture (CellTiter 96® AQueous One Solution Cell Proliferation Assay; Promega, Madison, Wis., USA).

Results

The Effect of Zinc on Cell Death in Presence or Absence of SKIP (SEQ ID NO:6) in PC12 Cells PC12 cells were exposed to $ZnCl_2$ in concentration of 400 µM in presence or absence of increasing concentrations of SKIP (SEQ ID NO:6). $ZnCl_2$ concentration of 400 µM was used based on previous results (Oz et al. 2012 *The ADNP Derived Peptide, NAP Modulates the Tubulin Pool: Implication for Neurotrophic and Neuroprotective Activities*. PLoS One 7, e51458). Zinc treatment results in ~20% cell death, which was protected by the addition of SKIP, over a wide range of concentrations (FIGS. 15 A and B). Another analogue that was tested, NAPVSGIPQ (SEQ ID NO:5), also showed protection in the same PC12 cell/$ZnCl_2$ assays at the concentration of $10^{-13}$M, reaching a level of statistical significance (FIG. 19).

II. In Vivo Protection
Methods
Animals

All procedures involving animals were approved by the Animal Care and Use Committee of Tel Aviv University and the National Institutes of Health (Bethesda, Md.). ADNP heterozygous mice, a model for cognitive impairments (Vulih-Shultzman et al., 2007, *J. Pharmacol. Exp. Ther.* 323: 438-449), were housed in a 12-h light/12-h dark cycle facility, and free access to rodent chow and water was available.

SKIP (SEQ ID NO:6) Treatment

SKIP (SEQ ID NO:6) treatment included daily intranasal administrations over a 1 month period to 5-month-old male mice (2 µg/5 µl/mouse/day). For intranasal administration, the peptide was dissolved in a vehicle solution, in which each milliliter included 7.5 mg of NaCl, 1.7 mg of citric acid monohydrate, 3 mg of disodium phosphate dihydrate, and 0.2 mg of benzalkonium chloride solution (50%). SKIP (SEQ ID NO:6) or vehicle solution (DD) was administered to mice hand-held in a semisupine position with nostrils facing the investigator. A pipette tip was used to administer 5 µl/each nostril. The mouse was handheld until the solution was totally absorbed (~10 s). Nasal SKIP (SEQ ID NO:6)

application was performed daily, twice a day, for 1 month (5 days a week). After 1 month, SKIP (SEQ ID NO:6) was applied 2 h before the behavioral tests (described below).

Object Recognition Test

The test includes 2 consecutive days of habituation (five minutes per day) and the experimental day which consists of the three phases. The test was conducted two hours after the daily intranasal SKIP (SEQ ID NO:6). During the first phase (Phase 1, habituation phase), the open field apparatus (arena of 50×50 cm) contained two identical objects (samples) and a mouse was placed in the apparatus facing the wall and allowed to freely explore the objects. At the end of the 5-min session of Phase 1, the mouse was put back into its home cage for 3 hours. Subsequently, the mouse was placed back into the apparatus for 3 min for the second phase (Phase 2, short retention choice phase), during which one of the familiar (sample (objects was replaced with a novel object. Approximately 24 h after the completion of Phase 1 test, the mouse was placed into the apparatus for 3 min for the third phase (Phase 3, long retention choice phase), during which one of the familiar objects was replaced with another novel object. The mouse was kept in its home cage between Phases 2 and 3. The objects (made of plastic or metal, 4×5 cm$^2$) were washed and dried, and the apparatus was wiped clean before the start of each session for each mouse. The positions of the familiar and novel objects during Phases 2 and 3 were counterbalanced within and between groups to exclude the possibility of positional effects, but were kept the same for a given animal. The time spent sniffing/touching each object was measured. The data was analyzed using the following formula: D1=b−a, when 'a' designated the time of exploration of the familiar object and 'b' designated the time of exploration of the novel object. The formula evaluates the discrimination capacity of the mice between the novel object and the familiar object.

Morris Water Maze (MWM)

The apparatus was a pool with a diameter of 140 cm, filled with opaque water (23-24° C.). An escape platform (12×12 cm$^2$) was placed 0.5 cm below the water surface. Two daily tests, constituting two blocks of trials, 90 s each, were performed for 5 consecutive days. The platform location and the animal starting point were held constant within each pair of daily tests, but they were changed from day to day. The mice were allowed to stay on the platform for 20 s before and after each trial. The time taken for an animal to reach the platform (latency) was recorded. The daily improvement (in seconds to reach the hidden platform) for each animal (in comparison to the starting day) was calculated. On the fifth day, a probe test was performed after the second daily trial as follows. The platform was removed from the maze and the distance traveled and the time spent by the mice in the pool's quarter where the platform used to be, were recorded (for a maximal period of 90 s). Mouse behavior in the quarter that is most distant from the target quarter was also measured. All measurements were recorded as the percentage of the total time spent or total path traveled in the pool. To determine the general mobility of the mice in the pool, the swimming behavior of each animal was monitored and the total path length and swim velocity were calculated. Monitoring was performed with the HVS video tracking system (HVS Image Ltd., Hampton, UK).

Elevated Plus-Maze

The maze consisted of two open arms (50 cm×10 cm) and two closed arms 50 cm×10 cm×40 cm), with arms of each type opposite to each other. The maze was elevated to a height of 50 cm from the floor. The experiment was conducted in a dimly lit testing room. Mice were placed into the centre of the maze facing an open arm and were left free to explore it for 5 min. The number of entries into the open and closed arms and the time spent in the open or closed arms were registered. The data were analyzed using the following formula: D2=(b−a)/(b+a), when 'a' designated the time spent in the open arm and 'b' designated the time spent in the closed arm.

Results

Object Recognition Test

In this novel-object test, object recognition was distinguished by the animal spending more time exploring the novel object. This object-recognition procedure takes advantage of an animal's tendency to approach and explore novelty, in order to do so they must remember and differentiate the familiar from the novel object. Animal performance in the object recognition memory task is presented in FIG. 15. ADNP+/− mice showed reduced time spent on the novel object, demonstrating a deficit in working memory (FIG. 16A). Treatment with SKIP for 1 month (twice a day) improved the memory. Two-way ANOVA revealed significant effect of genotype (F(1, 27)=6.5, p=0.017), and treatment (F(1,27)=4.5, p=0.045) in terms of the total time spent exploring all objects across the 3 phases of testing. Measurements of long term memory, 24 hours after the first exposure, revealed significant difference between ADNP-deficient mice and control mice (P<0.05) (FIG. 16B). Furthermore, SKIP (SEQ ID NO:6) treatment resulted in improvement in long term memory for the ADNP-deficient mice, bringing them to the control levels (FIG. 16B).

Morris Water Maze

The test was performed to assess potential spatial learning and memory deficits under the influence of the ADNP-deficient phenotype and possible reversal by the ADNP-derived neuroprotective peptide, SKIP (SEQ ID NO:6). In the study, 4-month-old ADNP+/+ and ADNP+/− male mice were treated by intranasal administration of either vehicle or SKIP (daily treatments, twice a day, for 1 month). The treated mice were subjected to a Morris water maze at the age of 5 month and continued to receive SKIP (SEQ ID NO:6) during the 5 testing days of the water maze. Behavioral assessments were performed in a water maze by measurements of the time required to find a hidden platform. Two daily tests were performed over 5 testing days. The platform location and the animal's starting point were held constant within each pair of daily trials, but the location of the platform and the animal's starting point were changed every day. In the first daily test, indicative of reference memory, ADNP+/− male mice were impaired compared with control animals (FIG. 17A). Furthermore, although the ADNP+/+ mice learned the task after 3 testing days, ADNP+/− male mice did not learn the task (FIG. 16A). SKIP (SEQ ID NO:6) treatment improved learning on the 2nd day, which was not apparent in the vehicle-treated ADNP+/− mice (FIG. 17A). The daily performance of each mouse was calculated as the difference [decrease in latency (seconds) to find the hidden platform, i.e., improvement in performance] from performance of the same mouse on the first testing day. In the second daily test, on the 5th day of the Morris water maze testing there was a statistically significant difference (p<0.05, two tailed t-test) between the control (designated ADNP+/+) mice and the ADNP-deficient (designated ADNP+/−) mice (FIG. 17B). While ADNP+/− mice did not improve their performance on the 5th day in the second daily test, SKIP (SEQ ID NO:6) treatment resulted in improvement in the behavior of the ADNP-deficient mice, bringing them to the control levels (FIG. 17B).

Elevated Plus-Maze

To assess anxiety-related behavior we conducted an elevated plus maze test. In this test, control group (designated ADNP+/+) spent more time in the closed arms compared with the time spent in the open arms (FIG. 18). On the other hand, the ADNP-deficient group (designated ADNP+/−) spent more time in the open arms (FIG. 18). ANOVA test showed a significant difference (P=0.003) of the time spent in the open and closed arms between ADNP+/+ mice and ADNP+/− mice. The test reveals risky behavior of the ADNP-deficient mice as opposed to control behavior. SKIP (SEQ ID NO:6) treatment resulted in reduction in the risky behavior of the ADNP-deficient mice.

Conclusions

SKIP (SEQ ID NO:6), a 4-amino acid peptide provides neuroprotection in vitro and cognitive protection in vivo following nasal administration. SKIP (SEQ ID NO:6) is the EB1/EB3 binding site, indicating neuroprotection through EB/microtubule interaction. Peptides NAPVSIPQ and NAPVSKIPQ have been shown to bind EB3 in vitro in a column chromatography method described in Example 1. Since SKIP (SEQ ID NO:6) is a small peptide that can be readily made with high bioavailability, this peptide, including its modified variants (such as all D-amino acid SKIP and acetylated and/or amidated SKIP, e.g., acetyl-SKIP-NH$_2$) is of significant potential value as a therapeutic agent for neuroprotection.

Example 3: Compounds that have been Identified as Modulators of Cell Death/Survival/Plasticity Based on their Interaction with EB3 or EB1 Protein

TABLE 4

| name | Description | |
| --- | --- | --- |
| TRAZODONE | major depressive disorders | Anti-anxiety Agents<br>Antidepressants, Second-Generation<br>Serotonin Uptake Inhibitors<br>Antidepressive Agents, Second-Generation |
| ACETOPHENAZINE | It is used in the treatment of disorganized and psychotic thinking. It is also used to help treat false perceptions (e.g. hallucinations or delusions). It primarily targets the dopamine D2 receptor. | Acetophenazine blocks postsynaptic mesolimbic dopaminergic D1 and D2 receptors in the brain; depresses the release of hypothalamic and hypophyseal hormones and is believed to depress the reticular activating system thus affecting basal metabolism, body temperature, wakefulness, vasomotor tone, and emesis. |
| Carphenazine | treatment of acute or chronic schizophrenic reactions | Carphenazine blocks postsynaptic mesolimbic dopaminergic D1 and D2 receptors in the brain; depresses the release of hypothalamic and hypophyseal hormones and is believed to depress the reticular activating system thus affecting basal metabolism, body temperature, wakefulness, vasomotor tone, and emesis. |
| Flumazenil | Fumazenil is an imidazobenzodiazepine derivative and a potent benzodiazepine receptor antagonist that competitively inhibits the activity at the benzodiazepine recognition site on the GABA/benzodiazepine receptor complex, thereby reversing the effects of benzodiazepine on the central nervous system. | Flumazenil, an imidazobenzodiazepine derivative, antagonizes the actions of benzodiazepines on the central nervous system. Flumazenil competitively inhibits the activity at the benzodiazepine recognition site on the GABA/benzodiazepine receptor complex. Flumazenil is a weak partial agonist in some animal models of activity, but has little or no agonist activity in man. |
| QUETIAPINE | Quetiapine is indicated for the treatment of schizophrenia as well as for the treatment of acute manic episodes associated with bipolar I disorder | Quetiapine's antipsychotic activity is likely due to a combination of antagonism at D2 receptors in the mesolimbic pathway and 5HT2A receptors in the frontal cortex. Antagonism at D2 receptors relieves positive symptoms while antagonism at 5HT2A receptors relieves negative symptoms of schizophrenia |

TABLE 4-continued

| name | Description | |
|---|---|---|
| RISPERIDONE | antipsychotic drug with high affinity for 5-hydrotryptamine (5-HT) and dopamine D2 receptors. It is used primarily in the management of schizophrenia, inappropriate behavior in severe dementia and manic episodes associated with bipolar I disorder. | Blockade of dopaminergic D2 receptors in the limbic system alleviates positive symptoms of schizophrenia such as hallucinations, delusions, and erratic behavior and speech. Blockade of serotonergic 5-$HT_2$ receptors in the mesocortical tract, |
| FLUVOXAMINE | Fluvoxamine is an antidepressant which functions pharmacologically as a selective serotonin reuptake inhibitor. Though it is in the same class as other SSRI drugs, it is most often used to treat obsessive-compulsive disorder. | inhibition of CNS neuronal uptake of serotonin. |
| THIOTHIXENE | A thioxanthine used as an antipsychotic agent | Thiothixene acts as an antagonist (blocking agent) on different postsysnaptic receptors -on dopaminergic-receptors (subtypes D1, D2, D3 and D4 - different antipsychotic properties on productive and unproductive symptoms), on serotonergic-receptors (5-HT1 and 5-HT2 |
| DILTIAZEM | vasodilating action due to its antagonism of the actions of the calcium ion in membrane functions. It is also teratogenic | Possibly by deforming the channel, inhibiting ion-control gating mechanisms, and/or interfering with the release of calcium from the sarcoplasmic reticulum, diltiazem, like verapamil, inhibits the influx of extracellular calcium across both the myocardial and vascular smooth muscle cell membranes |
| ALMOTRIPTAN | Almotriptan is a triptan drug for the treatment of migraine headaches | Almotriptan binds with high affinity to human 5-$HT_{1B}$ and 5-$HT_{1D}$ receptors leading to cranial blood vessel constriction. |
| METHYSERGIDE | Methysergide is used prophylactically in migraine and other vascular headaches and to antagonize serotonin in the carcinoid syndrome | |

All patents, patent applications, and other publications, including GenBank Accession Numbers, cited in this application are incorporated by reference in the entirety for all purposes.

INFORMAL SEQUENCE LISTING

SEQ ID NO: 1
NAPVSxIPQ
(x is one amino acid of any identity)

SEQ ID NO: 2
NAPVSKIPQ

SEQ ID NO: 3
R$^1$-NAPVSxIPQ-R$^2$

SEQ ID NO: 4
R$^3$-NAPVTxIPQ-R$^4$
(each of R$^1$, R$^2$, R$^3$, and R$^4$ is an amino acid sequence independent of each other, having at least one, up to 40 amino acids of any identity)

INFORMAL SEQUENCE LISTING -continued

SEQ ID NO: 5
NAPVSGIPQ

SEQ ID NO: 6
SKIP

SEQ ID NO: 7
SGIP

SEQ ID NO: 8
SRIP

What is claimed is:

1. An isolated peptide consisting of the amino acid sequence of SKIP (SEQ ID NO: 6), which is acetylated at the N-terminus and amidated at the C-terminus in an effective amount to inhibit cell death or increase cell plasticity.

2. The peptide of claim 1, wherein the amino acid sequence of SKIP (SEQ ID NO:6) comprises at least one D-amino acid.

3. The peptide of claim 2, wherein the amino acid sequence of SKIP (SEQ ID NO:6) is all D-amino acid SKIP.

4. The peptide of claim 1, wherein the cell is a neuronal cell.

5. A composition comprising the peptide of claim 1 and a pharmaceutically acceptable excipient.

6. The composition of claim 5, which is formulated for oral or nasal administration.

7. A method for promoting cell survival or plasticity, comprising contacting a cell with the peptide of claim 1 in an amount that is effective to increase the expression of an EB protein.

8. The method of claim 7, wherein the EB protein is an EB1 protein, or an EB2 protein, or an EB3 protein.

9. The method of claim 7, wherein the cell is a neuronal cell.

10. The method of claim 7, wherein the cell is present in a patient's body.

11. The method of claim 7, wherein the amino acid sequence of SKIP (SEQ ID NO:6) is all D-amino acid SKIP.

12. The method of claim 7, comprising a step of administering the peptide to a patient diagnosed of cognitive impairment.

* * * * *

UNITED STATES PATENT AND TRADEMARK OFFICE
CERTIFICATE OF CORRECTION

PATENT NO. : 10,118,943 B2
APPLICATION NO. : 14/401504
DATED : November 6, 2018
INVENTOR(S) : Gozes et al.

It is certified that error appears in the above-identified patent and that said Letters Patent is hereby corrected as shown below:

On the Title Page

Under abstract "12 Claims, 20 Drawing Sheets" should read --14 Claims, 20 Drawing Sheets--.

In the Claims

Column 88, Line 66, after Claim 12 insert Claims 13 and 14:
--13. A composition comprising the peptide of claim 1 and a pharmaceutically acceptable excipient.
14. The composition of claim 13, which is formulated for oral or nasal administration.--.

Signed and Sealed this
Eighteenth Day of August, 2020

Andrei Iancu
*Director of the United States Patent and Trademark Office*

SEQUENCE LISTING

```
<160> NUMBER OF SEQ ID NOS: 62

<210> SEQ ID NO 1
<211> LENGTH: 9
<212> TYPE: PRT
<213> ORGANISM: Artificial Sequence
<220> FEATURE:
<223> OTHER INFORMATION: synthetic novel peptide core sequence derived
      from hybrid microtubule end-binding protein 3 (EB3)-binding
      microtubule plus-end tracking proteins (+TIPs) and activity-
      dependent neurotrophic factor (ADNF) active core site (NAP)
<220> FEATURE:
<221> NAME/KEY: VARIANT
<222> LOCATION: (6)...(6)
<223> OTHER INFORMATION: Xaa = any amino acid

<400> SEQUENCE: 1

Asn Ala Pro Val Ser Xaa Ile Pro Gln
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic novel peptide core sequence SKIP
      derived from hybrid microtubule end-binding protein 3 (EB3)-
      binding microtubule plus-end tracking proteins (+TIPs) and
      activity-dependent neurotrophic factor (ADNF) active core site
      (NAP)

<400> SEQUENCE: 2

Asn Ala Pro Val Ser Lys Ile Pro Gln
1               5

<210> SEQ ID NO 3
<211> LENGTH: 89
<212> TYPE: PRT
<213> ORGANISM: Artificial Sequence
<220> FEATURE:
<223> OTHER INFORMATION: synthetic novel peptide core sequence derived
      from hybrid microtubule end-binding protein 3 (EB3)-binding
      microtubule plus-end tracking proteins (+TIPs) and activity-
      dependent neurotrophic factor (ADNF) active core site (NAP)
<220> FEATURE:
<221> NAME/KEY: VARIANT
<222> LOCATION: (1)...(39)
```

```
<223> OTHER INFORMATION: Xaa = any amino acid, may be present or absent
<220> FEATURE:
<221> NAME/KEY: VARIANT
<222> LOCATION: (40)...(40)
<223> OTHER INFORMATION: Xaa = any amino acid
<220> FEATURE:
<221> NAME/KEY: VARIANT
<222> LOCATION: (46)...(46)
<223> OTHER INFORMATION: Xaa = any amino acid
<220> FEATURE:
<221> NAME/KEY: VARIANT
<222> LOCATION: (50)...(50)
<223> OTHER INFORMATION: Xaa = any amino acid
<220> FEATURE:
<221> NAME/KEY: VARIANT
<222> LOCATION: (51)...(89)
<223> OTHER INFORMATION: Xaa = any amino acid, may be present or absent

<400> SEQUENCE: 3

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Xaa Ile Pro
        35                  40                  45

Gln Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa
             85

<210> SEQ ID NO 4
<211> LENGTH: 89
<212> TYPE: PRT
<213> ORGANISM: Artificial Sequence
<220> FEATURE:
<223> OTHER INFORMATION: synthetic novel peptide core sequence derived
      from hybrid microtubule end-binding protein 3 (EB3)-binding
      microtubule plus-end tracking proteins (+TIPs) and activity-
      dependent neurotrophic factor (ADNF) active core site (NAP)
<220> FEATURE:
<221> NAME/KEY: VARIANT
<222> LOCATION: (1)...(39)
<223> OTHER INFORMATION: Xaa = any amino acid, may be present or absent
<220> FEATURE:
<221> NAME/KEY: VARIANT
<222> LOCATION: (40)...(40)
<223> OTHER INFORMATION: Xaa = any amino acid
<220> FEATURE:
<221> NAME/KEY: VARIANT
<222> LOCATION: (46)...(46)
<223> OTHER INFORMATION: Xaa = any amino acid
<220> FEATURE:
<221> NAME/KEY: VARIANT
<222> LOCATION: (50)...(50)
<223> OTHER INFORMATION: Xaa = any amino acid
<220> FEATURE:
<221> NAME/KEY: VARIANT
<222> LOCATION: (51)...(89)
<223> OTHER INFORMATION: Xaa = any amino acid, may be present or absent

<400> SEQUENCE: 4

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Thr Xaa Ile Pro
        35                  40                  45
```

```
Gln Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa
                85

<210> SEQ ID NO 5
<211> LENGTH: 9
<212> TYPE: PRT
<213> ORGANISM: Artificial Sequence
<220> FEATURE:
<223> OTHER INFORMATION: synthetic novel peptide core sequence derived
      from hybrid microtubule end-binding protein 3 (EB3)-binding
      microtubule plus-end tracking proteins (+TIPs) and activity-
      dependent neurotrophic factor (ADNF) active core site (NAP)

<400> SEQUENCE: 5

Asn Ala Pro Val Ser Gly Ile Pro Gln
 1               5

<210> SEQ ID NO 6
<211> LENGTH: 4
<212> TYPE: PRT
<213> ORGANISM: Artificial Sequence
<220> FEATURE:
<223> OTHER INFORMATION: synthetic modulator of cell survival/plasticity
      core sequence SKIP1, SxIP sequence motif,
      microtubule tip localization signal

<400> SEQUENCE: 6

Ser Lys Ile Pro
 1

<210> SEQ ID NO 7
<211> LENGTH: 4
<212> TYPE: PRT
<213> ORGANISM: Artificial Sequence
<220> FEATURE:
<223> OTHER INFORMATION: synthetic modulator of cell survival/plasticity
      core sequence SGIP, SxIP sequence motif,
      microtubule tip localization signal, plexin EB
      protein interaction motif

<400> SEQUENCE: 7

Ser Gly Ile Pro
 1

<210> SEQ ID NO 8
<211> LENGTH: 4
<212> TYPE: PRT
<213> ORGANISM: Artificial Sequence
<220> FEATURE:
<223> OTHER INFORMATION: synthetic modulator of cell survival/plasticity
      core sequence, SxIP sequence motif, microtubule
      tip localization signal

<400> SEQUENCE: 8

Ser Arg Ile Pro
 1

<210> SEQ ID NO 9
<211> LENGTH: 9
<212> TYPE: PRT
<213> ORGANISM: Artificial Sequence
<220> FEATURE:
<223> OTHER INFORMATION: synthetic novel peptide core sequence derived
```

```
      from hybrid microtubule end-binding protein 3 (EB3)-binding
      microtubule plus-end tracking proteins (+TIPs) and activity-
      dependent neurotrophic factor (ADNF) active core site (NAP)
<220> FEATURE:
<221> NAME/KEY: VARIANT
<222> LOCATION: (6)...(6)
<223> OTHER INFORMATION: Xaa = any amino acid

<400> SEQUENCE: 9

Asn Ala Pro Val Thr Xaa Ile Pro Gln
1               5

<210> SEQ ID NO 10
<211> LENGTH: 4
<212> TYPE: PRT
<213> ORGANISM: Artificial Sequence
<220> FEATURE:
<223> OTHER INFORMATION: synthetic modulator of cell survival/plasticity
      core sequence, SxIP sequence motif, microtubule
      tip localization signal
<220> FEATURE:
<221> NAME/KEY: ACETYLATION
<222> LOCATION: (1)...(1)
<223> OTHER INFORMATION: acetyl-serine
<220> FEATURE:
<221> NAME/KEY: AMIDATION
<222> LOCATION: (4)...(4)
<223> OTHER INFORMATION: prolinamide

<400> SEQUENCE: 10

Ser Lys Ile Pro
1

<210> SEQ ID NO 11
<211> LENGTH: 9
<212> TYPE: PRT
<213> ORGANISM: Artificial Sequence
<220> FEATURE:
<223> OTHER INFORMATION: synthetic modulator of cell survival/plasticity
      core sequence SRIP, SxIP sequence motif,
      microtubule tip localization signal

<400> SEQUENCE: 11

Asn Ala Pro Val Ser Arg Ile Pro Gln
1               5

<210> SEQ ID NO 12
<211> LENGTH: 38
<212> TYPE: PRT
<213> ORGANISM: Artificial Sequence
<220> FEATURE:
<223> OTHER INFORMATION: synthetic human microtubule actin crosslinking
      factor (MACF2) SxIP motif EB1 binding domain

<400> SEQUENCE: 12

Thr His Arg Pro Thr Pro Arg Ala Gly Ser Arg Pro Ser Thr Ala Lys
1               5                   10                  15

Pro Ser Lys Ile Pro Thr Pro Gln Arg Lys Ser Pro Ala Ser Lys Leu
            20                  25                  30

Asp Lys Ser Ser Lys Arg
            35

<210> SEQ ID NO 13
<211> LENGTH: 39
<212> TYPE: PRT
<213> ORGANISM: Artificial Sequence
<220> FEATURE:
<223> OTHER INFORMATION: synthetic human adenomatous polyposis coli
      (APC) tumor suppressor protein SxIP motif EB1 binding domain
```

<400> SEQUENCE: 13

Tyr Asn Pro Ser Pro Arg Lys Ser Ser Ala Asp Ser Thr Ser Ala Arg
 1               5                  10                  15

Pro Ser Gln Ile Pro Thr Pro Val Asn Asn Asn Thr Lys Lys Arg Asp
             20                  25                  30

Ser Lys Thr Asp Ser Thr Glu
         35

<210> SEQ ID NO 14
<211> LENGTH: 39
<212> TYPE: PRT
<213> ORGANISM: Artificial Sequence
<220> FEATURE:
<223> OTHER INFORMATION: synthetic human CLIP associating protein 2
      (CLASP2) SxIP motif EB1 binding domain

<400> SEQUENCE: 14

Ser Ser Gly Val Gln Arg Val Leu Val Asn Ser Ala Ser Ala Gln Lys
 1               5                  10                  15

Arg Ser Lys Ile Pro Arg Ser Gln Gly Cys Ser Arg Glu Ala Ser Pro
             20                  25                  30

Ser Arg Leu Ser Val Ala Arg
         35

<210> SEQ ID NO 15
<211> LENGTH: 39
<212> TYPE: PRT
<213> ORGANISM: Artificial Sequence
<220> FEATURE:
<223> OTHER INFORMATION: synthetic human CLIP associating protein 2
      (CLASP2) SxIP motif EB1 binding domain

<400> SEQUENCE: 15

Gln Gly Cys Ser Arg Glu Ala Ser Pro Ser Arg Leu Ser Val Ala Arg
 1               5                  10                  15

Ser Ser Arg Ile Pro Arg Pro Ser Val Ser Gln Gly Cys Ser Arg Glu
             20                  25                  30

Ala Ser Arg Glu Ser Ser Arg
         35

<210> SEQ ID NO 16
<211> LENGTH: 39
<212> TYPE: PRT
<213> ORGANISM: Artificial Sequence
<220> FEATURE:
<223> OTHER INFORMATION: synthetic human stromal interaction molecule 1
      (STIM1) SxIP motif EB1 binding domain

<400> SEQUENCE: 16

Asp Thr Pro Ser Pro Val Gly Asp Ser Arg Ala Leu Gln Ala Ser Arg
 1               5                  10                  15

Asn Thr Arg Ile Pro His Leu Ala Gly Lys Lys Ala Val Ala Glu Glu
             20                  25                  30

Asp Asn Gly Ser Ile Gly Glu
         35

<210> SEQ ID NO 17
<211> LENGTH: 39
<212> TYPE: PRT
<213> ORGANISM: Artificial Sequence
<220> FEATURE:
<223> OTHER INFORMATION: synthetic mititic centromere associated kinesin (MCAK, KIF2c) MT depolymerase SxIP motif EB1 binding domain

<400> SEQUENCE: 17

Pro Leu Gln Glu Asn Val Thr Ile Gln Lys Gln Lys Arg Arg Ser Val
1               5                   10                  15

Asn Ser Lys Ile Pro Ala Pro Lys Glu Ser Leu Arg Ser Arg Ser Thr
            20                  25                  30

Arg Met Ser Thr Val Ser Glu
        35

<210> SEQ ID NO 18
<211> LENGTH: 35
<212> TYPE: PRT
<213> ORGANISM: Artificial Sequence
<220> FEATURE:
<223> OTHER INFORMATION: synthetic human regulator of Src tyrosine
      kinase p140Cap SxIP motif EB1 binding domain

<400> SEQUENCE: 18

Gly Ser Asn Glu Thr Ser Ser Pro Val Ser Glu Lys Pro Ser Ala Ser
1               5                   10                  15

Arg Thr Ser Ile Pro Val Leu Thr Ser Phe Gly Ala Arg Asn Ser Ser
            20                  25                  30

Ile Ser Phe
        35

<210> SEQ ID NO 19
<211> LENGTH: 39
<212> TYPE: PRT
<213> ORGANISM: Artificial Sequence
<220> FEATURE:
<223> OTHER INFORMATION: synthetic human DDA3 (proline/serine-rich
      coiled coil 1 (PSRC1)) SxIP motif EB1 binding domain

<400> SEQUENCE: 19

Pro Arg Pro Gln Gly Ala Ala Ala Lys Ser Ser Ser Gln Leu Pro Ile
1               5                   10                  15

Pro Ser Ala Ile Pro Arg Pro Ala Ser Arg Met Pro Leu Thr Ser Arg
            20                  25                  30

Ser Val Pro Pro Gly Arg Gly
        35

<210> SEQ ID NO 20
<211> LENGTH: 39
<212> TYPE: PRT
<213> ORGANISM: Artificial Sequence
<220> FEATURE:
<223> OTHER INFORMATION: synthetic mouse melanophilin (Melan) SxIP motif
      EB1 binding domain

<400> SEQUENCE: 20

Leu Arg Ala Ala Gly Leu Thr Val Lys Pro Ser Gly Lys Pro Arg Arg
1               5                   10                  15

Lys Ser Gly Ile Pro Ile Phe Leu Pro Arg Val Thr Glu Lys Leu Asp
            20                  25                  30

Arg Ile Pro Lys Thr Pro Pro
        35

<210> SEQ ID NO 21
<211> LENGTH: 268
<212> TYPE: PRT
<213> ORGANISM: Mus musculus
<220> FEATURE:

<223> OTHER INFORMATION: microtubule-associated protein RP/EB family
member 1 (MAPRE1, MARE1), adenomatous polyposis coli
(APC)-binding protein EB1, end-binding protein 1 (EB1)

<400> SEQUENCE: 21

Met Ala Val Asn Val Tyr Ser Thr Ser Val Thr Ser Asp Asn Leu Ser
1               5                   10                  15

Arg His Asp Met Leu Ala Trp Ile Asn Glu Ser Leu Gln Leu Asn Leu
            20                  25                  30

Thr Lys Ile Glu Gln Leu Cys Ser Gly Ala Ala Tyr Cys Gln Phe Met
        35                  40                  45

Asp Met Leu Phe Pro Gly Ser Ile Ala Leu Lys Lys Val Lys Phe Gln
    50                  55                  60

Ala Lys Leu Glu His Glu Tyr Ile Gln Asn Phe Lys Ile Leu Gln Ala
65                  70                  75                  80

Gly Phe Lys Arg Met Gly Val Asp Lys Ile Ile Pro Val Asp Lys Leu
                85                  90                  95

Val Lys Gly Lys Phe Gln Asp Asn Phe Glu Phe Val Gln Trp Phe Lys
            100                 105                 110

Lys Phe Phe Asp Ala Asn Tyr Asp Gly Lys Glu Tyr Asp Pro Val Ala
        115                 120                 125

Ala Arg Gln Gly Gln Glu Thr Ala Val Ala Pro Ser Leu Val Ala Pro
    130                 135                 140

Ala Leu Ser Lys Pro Lys Lys Pro Leu Gly Ser Ser Thr Ala Ala Pro
145                 150                 155                 160

Gln Arg Pro Ile Ala Thr Gln Arg Thr Thr Ala Ala Pro Lys Ala Gly
                165                 170                 175

Pro Gly Met Val Arg Lys Asn Pro Gly Val Gly Asn Gly Asp Asp Glu
            180                 185                 190

Ala Ala Glu Leu Met Gln Gln Val Lys Val Leu Lys Leu Thr Val Glu
        195                 200                 205

Asp Leu Glu Lys Glu Arg Asp Phe Tyr Phe Gly Lys Leu Arg Asn Ile
    210                 215                 220

Glu Leu Ile Cys Gln Glu Asn Glu Gly Glu Asn Asp Pro Val Leu Gln
225                 230                 235                 240

Arg Ile Val Asp Ile Leu Tyr Ala Thr Asp Glu Gly Phe Val Ile Pro
                245                 250                 255

Asp Glu Gly Gly Pro Gln Glu Gln Glu Gln Glu Tyr
            260                 265

<210> SEQ ID NO 22
<211> LENGTH: 268
<212> TYPE: PRT
<213> ORGANISM: Rattus norvegicus
<220> FEATURE:
<223> OTHER INFORMATION: microtubule-associated protein RP/EB family
member 1 (MAPRE1, MARE1), adenomatous polyposis coli
(APC)-binding protein EB1, end-binding protein 1 (EB1)

<400> SEQUENCE: 22

Met Ala Val Asn Val Tyr Ser Thr Ser Val Thr Ser Asp Asn Leu Ser
1               5                   10                  15

Arg His Asp Met Leu Ala Trp Ile Asn Glu Ser Leu Gln Leu Asn Leu
            20                  25                  30

Thr Lys Ile Glu Gln Leu Cys Ser Gly Ala Ala Tyr Cys Gln Phe Met
        35                  40                  45

Asp Met Leu Phe Pro Gly Ser Ile Ala Leu Lys Lys Val Lys Phe Gln

```
                    50                  55                  60

Ala Lys Leu Glu His Glu Tyr Ile Gln Asn Phe Lys Ile Leu Gln Ala
 65                  70                  75                  80

Gly Phe Lys Arg Met Gly Val Asp Lys Ile Ile Pro Val Asp Lys Leu
                 85                  90                  95

Val Lys Gly Lys Phe Gln Asp Asn Phe Glu Phe Val Gln Trp Phe Lys
                100                 105                 110

Lys Phe Phe Asp Ala Asn Tyr Asp Gly Lys Glu Tyr Asp Pro Val Ala
                115                 120                 125

Ala Arg Gln Gly Gln Glu Thr Ala Val Ala Pro Ser Leu Val Ala Pro
130                 135                 140

Ala Leu Ser Lys Pro Lys Lys Pro Leu Gly Ser Gly Ser Ala Ala Pro
145                 150                 155                 160

Gln Arg Pro Ile Ala Thr Gln Arg Thr Thr Ala Ala Pro Lys Ala Gly
                165                 170                 175

Pro Gly Met Val Arg Lys Asn Pro Gly Met Gly Asn Gly Asp Asp Glu
                180                 185                 190

Ala Ala Glu Leu Met Gln Gln Val Lys Val Leu Lys Leu Thr Val Glu
                195                 200                 205

Asp Leu Glu Lys Glu Arg Asp Phe Tyr Phe Gly Lys Leu Arg Asn Ile
210                 215                 220

Glu Leu Ile Cys Gln Glu Asn Glu Gly Glu Asn Asp Pro Val Leu Gln
225                 230                 235                 240

Arg Ile Val Asp Ile Leu Tyr Ala Thr Asp Glu Gly Phe Val Ile Pro
                245                 250                 255

Asp Glu Gly Gly Pro Gln Glu Glu Gln Glu Glu Tyr
                260                 265

<210> SEQ ID NO 23
<211> LENGTH: 268
<212> TYPE: PRT
<213> ORGANISM: Homo sapiens
<220> FEATURE:
<223> OTHER INFORMATION: microtubule-associated protein RP/EB family
      member 1 (MAPRE1, MARE1), adenomatous polyposis coli
      (APC)-binding protein EB1, end-binding protein 1 (EB1)

<400> SEQUENCE: 23

Met Ala Val Asn Val Tyr Ser Thr Ser Val Thr Ser Asp Asn Leu Ser
 1                   5                  10                  15

Arg His Asp Met Leu Ala Trp Ile Asn Glu Ser Leu Gln Leu Asn Leu
                 20                  25                  30

Thr Lys Ile Glu Gln Leu Cys Ser Gly Ala Ala Tyr Cys Gln Phe Met
                 35                  40                  45

Asp Met Leu Phe Pro Gly Ser Ile Ala Leu Lys Lys Val Lys Phe Gln
                 50                  55                  60

Ala Lys Leu Glu His Glu Tyr Ile Gln Asn Phe Lys Ile Leu Gln Ala
 65                  70                  75                  80

Gly Phe Lys Arg Met Gly Val Asp Lys Ile Ile Pro Val Asp Lys Leu
                 85                  90                  95

Val Lys Gly Lys Phe Gln Asp Asn Phe Glu Phe Val Gln Trp Phe Lys
                100                 105                 110

Lys Phe Phe Asp Ala Asn Tyr Asp Gly Lys Asp Tyr Asp Pro Val Ala
                115                 120                 125

Ala Arg Gln Gly Gln Glu Thr Ala Val Ala Pro Ser Leu Val Ala Pro
130                 135                 140
```

```
Ala Leu Asn Lys Pro Lys Pro Leu Thr Ser Ser Ala Pro
145                 150                 155                 160

Gln Arg Pro Ile Ser Thr Gln Arg Thr Ala Ala Pro Lys Ala Gly
            165                 170                 175

Pro Gly Val Val Arg Lys Asn Pro Gly Val Gly Asn Gly Asp Asp Glu
        180                 185                 190

Ala Ala Glu Leu Met Gln Gln Val Asn Val Leu Lys Leu Thr Val Glu
    195                 200                 205

Asp Leu Glu Lys Glu Arg Asp Phe Tyr Phe Gly Lys Leu Arg Asn Ile
210                 215                 220

Glu Leu Ile Cys Gln Glu Asn Glu Gly Glu Asn Asp Pro Val Leu Gln
225                 230                 235                 240

Arg Ile Val Asp Ile Leu Tyr Ala Thr Asp Glu Gly Phe Val Ile Pro
                245                 250                 255

Asp Glu Gly Gly Pro Gln Glu Glu Gln Glu Glu Tyr
            260                 265
```

<210> SEQ ID NO 24
<211> LENGTH: 281
<212> TYPE: PRT
<213> ORGANISM: Mus musculus

<400> SEQUENCE: 24

```
Met Ala Val Asn Val Tyr Ser Thr Ser Val Thr Ser Glu Asn Leu Ser
 1               5                  10                  15

Arg His Asp Met Leu Ala Trp Val Asn Asp Ser Leu His Leu Asn Tyr
            20                  25                  30

Thr Lys Ile Glu Gln Leu Cys Ser Gly Ala Ala Tyr Cys Gln Phe Met
        35                  40                  45

Asp Met Leu Phe Pro Gly Cys Val His Leu Arg Lys Val Lys Phe Gln
    50                  55                  60

Ala Lys Leu Glu His Glu Tyr Ile His Asn Phe Lys Val Leu Gln Ala
65                  70                  75                  80

Ala Phe Lys Lys Met Gly Val Asp Lys Ile Ile Pro Val Glu Lys Leu
                85                  90                  95

Val Lys Gly Lys Phe Gln Asp Asn Phe Glu Phe Ile Gln Trp Phe Lys
            100                 105                 110

Lys Phe Phe Asp Ala Asn Tyr Asp Gly Lys Asp Tyr Asn Pro Leu Leu
        115                 120                 125

Ala Arg Gln Gly Gln Asp Val Ala Pro Pro Asn Pro Gly Asp Gln
    130                 135                 140

Ile Phe Asn Lys Ser Lys Lys Leu Ile Gly Thr Ala Val Pro Gln Arg
145                 150                 155                 160

Thr Ser Pro Thr Gly Pro Lys Asn Met Gln Thr Ser Gly Arg Leu Ser
                165                 170                 175

Asn Val Ala Pro Pro Cys Ile Leu Arg Lys Asn Pro Pro Ser Ala Arg
            180                 185                 190

Asn Gly Gly His Glu Ala Asp Ala Gln Ile Leu Glu Leu Asn Gln Gln
        195                 200                 205

Leu Leu Asp Leu Lys Leu Thr Val Asp Gly Leu Glu Lys Glu Arg Asp
    210                 215                 220

Phe Tyr Phe Ser Lys Leu Arg Asp Ile Glu Leu Ile Cys Gln Glu His
225                 230                 235                 240

Glu Ser Glu Asn Ser Pro Val Ile Ser Gly Ile Ile Gly Ile Leu Tyr
```

Ala Thr Glu Glu Gly Phe Ala Pro Pro Glu Asp Asp Glu Ile Glu Glu
                    260                 265                 270

His Gln Gln Glu Asp Gln Asp Glu Tyr
            275                 280

<210> SEQ ID NO 25
<211> LENGTH: 281
<212> TYPE: PRT
<213> ORGANISM: Rattus norvegicus
<220> FEATURE:
<223> OTHER INFORMATION: microtubule-associated protein RP/EB family
      member 3 (MAPRE3, MARE3), adenomatous polyposis coli
      (APC)-binding protein EB3, end-binding protein 3 (EB3)

<400> SEQUENCE: 25

Met Ala Val Asn Val Tyr Ser Thr Ser Val Thr Ser Glu Asn Leu Ser
  1               5                  10                  15

Arg His Asp Met Leu Ala Trp Val Asn Asp Ser Leu His Leu Asn Tyr
                 20                  25                  30

Thr Lys Ile Glu Gln Leu Cys Ser Gly Ala Ala Tyr Cys Gln Phe Met
             35                  40                  45

Asp Met Leu Phe Pro Gly Cys Val His Leu Arg Lys Val Lys Phe Gln
 50                  55                  60

Ala Lys Leu Glu His Glu Tyr Ile His Asn Phe Lys Val Leu Gln Ala
 65                  70                  75                  80

Ala Phe Lys Lys Met Gly Val Asp Lys Ile Ile Pro Val Glu Lys Leu
                 85                  90                  95

Val Lys Gly Lys Phe Gln Asp Asn Phe Glu Phe Ile Gln Trp Phe Lys
            100                 105                 110

Lys Phe Phe Asp Ala Asn Tyr Asp Gly Lys Asp Tyr Asn Pro Leu Leu
            115                 120                 125

Ala Arg Gln Gly Gln Asp Val Ala Pro Pro Asn Pro Gly Asp Gln
130                 135                 140

Ile Phe Asn Lys Ser Lys Lys Leu Ile Gly Thr Ala Val Pro Gln Arg
145                 150                 155                 160

Thr Ser Pro Thr Gly Pro Lys Asn Met Gln Thr Ser Gly Arg Leu Ser
                165                 170                 175

Asn Val Ala Pro Pro Cys Ile Leu Arg Lys Asn Pro Pro Ser Ala Arg
            180                 185                 190

Asn Gly Gly His Glu Ala Asp Ala Gln Ile Leu Glu Leu Asn Gln Gln
            195                 200                 205

Leu Leu Asp Leu Lys Leu Thr Val Asp Gly Leu Glu Lys Glu Arg Asp
210                 215                 220

Phe Tyr Phe Ser Lys Leu Arg Asp Ile Glu Leu Ile Cys Gln Glu His
225                 230                 235                 240

Glu Ser Glu Asn Ser Pro Val Ile Ser Gly Ile Ile Gly Ile Leu Tyr
                245                 250                 255

Ala Thr Glu Glu Gly Phe Ala Pro Pro Glu Asp Asp Glu Ile Glu Glu
                260                 265                 270

His Gln Gln Glu Asp Gln Asp Glu Tyr
            275                 280

<210> SEQ ID NO 26
<211> LENGTH: 281
<212> TYPE: PRT
<213> ORGANISM: Homo sapiens
<220> FEATURE:
<223> OTHER INFORMATION: microtubule-associated protein RP/EB family
      member 3 (MAPRE3, MARE3), adenomatous polyposis coli
      (APC)-binding protein EB3, end-binding protein 3 (EB3)

<400> SEQUENCE: 26

Met Ala Val Asn Val Tyr Ser Thr Ser Val Thr Ser Glu Asn Leu Ser
 1               5                  10                  15

Arg His Asp Met Leu Ala Trp Val Asn Asp Ser Leu His Leu Asn Tyr
             20                  25                  30

Thr Lys Ile Glu Gln Leu Cys Ser Gly Ala Ala Tyr Cys Gln Phe Met
         35                  40                  45

Asp Met Leu Phe Pro Gly Cys Val His Leu Arg Lys Val Lys Phe Gln
 50                  55                  60

Ala Lys Leu Glu His Glu Tyr Ile His Asn Phe Lys Val Leu Gln Ala
 65                  70                  75                  80

Ala Phe Lys Lys Met Gly Val Asp Lys Ile Ile Pro Val Glu Lys Leu
             85                  90                  95

Val Lys Gly Lys Phe Gln Asp Asn Phe Glu Phe Ile Gln Trp Phe Lys
        100                 105                 110

Lys Phe Phe Asp Ala Asn Tyr Asp Gly Lys Asp Tyr Asn Pro Leu Leu
            115                 120                 125

Ala Arg Gln Gly Gln Asp Val Ala Pro Pro Asn Pro Gly Asp Gln
130                 135                 140

Ile Phe Asn Lys Ser Lys Lys Leu Ile Gly Thr Ala Val Pro Gln Arg
145                 150                 155                 160

Thr Ser Pro Thr Gly Pro Lys Asn Met Gln Thr Ser Gly Arg Leu Ser
                165                 170                 175

Asn Val Ala Pro Pro Cys Ile Leu Arg Lys Asn Pro Pro Ser Ala Arg
            180                 185                 190

Asn Gly Gly His Glu Thr Asp Ala Gln Ile Leu Glu Leu Asn Gln Gln
        195                 200                 205

Leu Val Asp Leu Lys Leu Thr Val Asp Gly Leu Glu Lys Glu Arg Asp
210                 215                 220

Phe Tyr Phe Ser Lys Leu Arg Asp Ile Glu Leu Ile Cys Gln Glu His
225                 230                 235                 240

Glu Ser Glu Asn Ser Pro Val Ile Ser Gly Ile Ile Gly Ile Leu Tyr
                245                 250                 255

Ala Thr Glu Glu Gly Phe Ala Pro Pro Glu Asp Asp Glu Ile Glu Glu
            260                 265                 270

His Gln Gln Glu Asp Gln Asp Glu Tyr
        275                 280

<210> SEQ ID NO 27
<211> LENGTH: 326
<212> TYPE: PRT
<213> ORGANISM: Mus musculus
<220> FEATURE:
<223> OTHER INFORMATION: microtubule-associated protein RP/EB family
      member 2 (MAPRE2, MARE2), adenomatous polyposis coli
      (APC)-binding protein EB2, end-binding protein 2 (EB2)

<400> SEQUENCE: 27

Met Pro Gly Pro Thr Gln Thr Leu Ser Pro Asn Gly Glu Asn Asn Asn
 1               5                  10                  15

Asp Ile Ile Gln Asp Asn Gly Thr Ile Ile Pro Phe Arg Lys His Thr
             20                  25                  30

Val Arg Gly Glu Arg Ser Tyr Ser Trp Gly Met Ala Val Asn Val Tyr
            35                  40                  45

Ser Thr Ser Ile Thr Gln Glu Thr Met Ser Arg His Asp Ile Ile Ala
 50                  55                  60

Trp Val Asn Asp Ile Val Ser Leu Asn Tyr Thr Lys Val Glu Gln Leu
 65                  70                  75                  80

Cys Ser Gly Ala Ala Tyr Cys Gln Phe Met Asp Met Leu Phe Pro Gly
                 85                  90                  95

Cys Ile Ser Leu Lys Lys Val Lys Phe Gln Ala Lys Leu Glu His Glu
                100                 105                 110

Tyr Ile His Asn Phe Lys Leu Leu Gln Ala Ser Phe Lys Arg Met Asn
                115                 120                 125

Val Asp Lys Val Ile Pro Val Glu Lys Leu Val Lys Gly Arg Phe Gln
130                 135                 140

Asp Asn Leu Asp Phe Ile Gln Trp Phe Lys Lys Phe Tyr Asp Ala Asn
145                 150                 155                 160

Tyr Asp Gly Lys Glu Tyr Asp Pro Val Glu Ala Arg Gln Gly Gln Asp
                165                 170                 175

Ala Ile Pro Pro Pro Asp Pro Gly Glu Gln Ile Phe Asn Leu Pro Lys
                180                 185                 190

Lys Ser His His Ala Asn Ser Pro Thr Ala Gly Ala Ala Lys Ser Ser
                195                 200                 205

Pro Ala Ser Lys Pro Gly Ser Thr Pro Ser Arg Pro Ser Ser Ala Lys
                210                 215                 220

Arg Ala Ser Ser Ser Gly Ser Ala Ser Arg Ser Asp Lys Asp Leu Glu
225                 230                 235                 240

Thr Gln Val Ile Gln Leu Asn Glu Gln Val His Ser Leu Lys Leu Ala
                245                 250                 255

Leu Glu Gly Val Glu Lys Glu Arg Asp Phe Tyr Phe Gly Lys Leu Arg
                260                 265                 270

Glu Ile Glu Leu Leu Cys Gln Glu His Gly Gln Glu Asn Asp Asp Leu
                275                 280                 285

Val Gln Arg Leu Met Glu Val Leu Tyr Ala Ser Asp Glu Gln Glu Gly
290                 295                 300

Gln Thr Glu Glu Pro Glu Ala Glu Gln Ala His Asp Gln Gln Pro
305                 310                 315                 320

Gln Gln Gln Glu Glu Tyr
                325

<210> SEQ ID NO 28
<211> LENGTH: 326
<212> TYPE: PRT
<213> ORGANISM: Rattus norvegicus
<220> FEATURE:
<223> OTHER INFORMATION: microtubule-associated protein RP/EB family
      member 2 (MAPRE2, MARE2), adenomatous polyposis coli
      (APC)-binding protein EB2, end-binding protein 2 (EB2)

<400> SEQUENCE: 28

Met Pro Gly Pro Thr Gln Thr Leu Ser Pro Asn Gly Glu Asn Asn Asn
 1               5                  10                  15

Asp Ile Ile Gln Asp Asn Gly Thr Ile Ile Pro Phe Arg Lys His Thr
                20                  25                  30

Val Arg Gly Glu Arg Ser Tyr Ser Trp Gly Met Ala Val Asn Val Tyr
                35                  40                  45

Ser Thr Ser Ile Thr Gln Glu Thr Met Ser Arg His Asp Ile Ile Ala

```
                    50                  55                  60
Trp Val Asn Asp Ile Val Ser Leu Asn Tyr Thr Lys Val Glu Gln Leu
 65                  70                  75                  80

Cys Ser Gly Ala Ala Tyr Cys Gln Phe Met Asp Met Leu Phe Pro Gly
                     85                  90                  95

Cys Ile Ser Leu Lys Lys Val Lys Phe Gln Ala Lys Leu Glu His Glu
                100                 105                 110

Tyr Ile His Asn Phe Lys Leu Leu Gln Ala Ser Phe Lys Arg Met Asn
            115                 120                 125

Val Asp Lys Val Ile Pro Val Glu Lys Leu Val Lys Gly Arg Phe Gln
130                 135                 140

Asp Asn Leu Asp Phe Ile Gln Trp Phe Lys Lys Phe Tyr Asp Ala Asn
145                 150                 155                 160

Tyr Asp Gly Lys Glu Tyr Asp Pro Val Glu Ala Arg Gln Gly Gln Asp
                165                 170                 175

Ala Ile Pro Pro Pro Asp Pro Gly Glu Gln Ile Phe Asn Leu Pro Lys
            180                 185                 190

Lys Ser His His Ala Asn Ser Pro Thr Ala Gly Ala Ala Lys Ser Ser
        195                 200                 205

Pro Ala Ala Lys Pro Gly Ser Thr Pro Ser Arg Pro Ser Ser Ala Lys
210                 215                 220

Arg Ala Ser Ser Gly Ser Ala Ser Arg Ser Asp Lys Asp Leu Glu
225                 230                 235                 240

Thr Gln Val Ile Gln Leu Asn Glu Gln Val His Ser Leu Lys Leu Ala
                245                 250                 255

Leu Glu Gly Val Glu Lys Glu Arg Asp Phe Tyr Phe Gly Lys Leu Arg
            260                 265                 270

Glu Ile Glu Leu Leu Cys Gln Glu His Gly Gln Glu Asn Asp Asp Leu
        275                 280                 285

Val Gln Arg Leu Met Glu Val Leu Tyr Ala Ser Asp Glu Gln Glu Gly
290                 295                 300

Gln Thr Glu Glu Pro Glu Val Glu Glu Gln Thr His Asp Gln Gln Pro
305                 310                 315                 320

Gln Gln Gln Glu Glu Tyr
                325

<210> SEQ ID NO 29
<211> LENGTH: 327
<212> TYPE: PRT
<213> ORGANISM: Homo sapiens
<220> FEATURE:
<223> OTHER INFORMATION: microtubule-associated protein RP/EB family
      member 2 (MAPRE2, MARE2), adenomatous polyposis coli
      (APC)-binding protein EB2, end-binding protein 2 (EB2)

<400> SEQUENCE: 29

Met Pro Gly Pro Thr Gln Thr Leu Ser Pro Asn Gly Glu Asn Asn Asn
 1               5                  10                  15

Asp Ile Ile Gln Asp Asn Asn Gly Thr Ile Ile Pro Phe Arg Lys His
                20                  25                  30

Thr Val Arg Gly Glu Arg Ser Tyr Ser Trp Gly Met Ala Val Asn Val
            35                  40                  45

Tyr Ser Thr Ser Ile Thr Gln Glu Thr Met Ser Arg His Asp Ile Ile
        50                  55                  60

Ala Trp Val Asn Asp Ile Val Ser Leu Asn Tyr Thr Lys Val Glu Gln
65                  70                  75                  80
```

```
Leu Cys Ser Gly Ala Ala Tyr Cys Gln Phe Met Asp Met Leu Phe Pro
                85                  90                  95

Gly Cys Ile Ser Leu Lys Lys Val Lys Phe Gln Ala Lys Leu Glu His
            100                 105                 110

Glu Tyr Ile His Asn Phe Lys Leu Leu Gln Ala Ser Phe Lys Arg Met
            115                 120                 125

Asn Val Asp Lys Val Ile Pro Val Glu Lys Leu Val Lys Gly Arg Phe
        130                 135                 140

Gln Asp Asn Leu Asp Phe Ile Gln Trp Phe Lys Lys Phe Tyr Asp Ala
145                 150                 155                 160

Asn Tyr Asp Gly Lys Glu Tyr Asp Pro Val Glu Ala Arg Gln Gly Gln
                165                 170                 175

Asp Ala Ile Pro Pro Asp Pro Gly Glu Gln Ile Phe Asn Leu Pro
                180                 185                 190

Lys Lys Ser His His Ala Asn Ser Pro Thr Ala Gly Ala Ala Lys Ser
            195                 200                 205

Ser Pro Ala Ala Lys Pro Gly Ser Thr Pro Ser Arg Pro Ser Ser Ala
        210                 215                 220

Lys Arg Ala Ser Ser Gly Ser Ala Ser Lys Ser Asp Lys Asp Leu
225                 230                 235                 240

Glu Thr Gln Val Ile Gln Leu Asn Glu Gln Val His Ser Leu Lys Leu
                245                 250                 255

Ala Leu Glu Gly Val Glu Lys Glu Arg Asp Phe Tyr Phe Gly Lys Leu
            260                 265                 270

Arg Glu Ile Glu Leu Leu Cys Gln Glu His Gly Gln Glu Asn Asp Asp
                275                 280                 285

Leu Val Gln Arg Leu Met Asp Ile Leu Tyr Ala Ser Glu Glu His Glu
        290                 295                 300

Gly His Thr Glu Glu Pro Glu Ala Glu Gln Ala His Glu Gln Gln
305                 310                 315                 320

Pro Pro Gln Gln Glu Glu Tyr
                325

<210> SEQ ID NO 30
<211> LENGTH: 8
<212> TYPE: PRT
<213> ORGANISM: Artificial Sequence
<220> FEATURE:
<223> OTHER INFORMATION: synthetic activity-dependent neurotrophic
      factor (ADNF) active core site (NAP), SIP

<400> SEQUENCE: 30

Asn Ala Pro Val Ser Ile Pro Gln
1               5

<210> SEQ ID NO 31
<211> LENGTH: 9
<212> TYPE: PRT
<213> ORGANISM: Artificial Sequence
<220> FEATURE:
<223> OTHER INFORMATION: synthetic novel peptide core sequence AAAA
      derived from hybrid microtubule end-binding protein 3
      (EB3)-binding microtubule plus-end tracking proteins (+TIPs) and
      activity-dependent neurotrophic factor (ADNF) active core site
      (NAP)

<400> SEQUENCE: 31

Asn Ala Pro Val Ala Ala Ala Ala Gln
1               5
```

<210> SEQ ID NO 32
<211> LENGTH: 9
<212> TYPE: PRT
<213> ORGANISM: Artificial Sequence
<220> FEATURE:
<223> OTHER INFORMATION: synthetic novel peptide core sequence SAIP
      derived from hybrid microtubule end-binding protein 3
      (EB3)-binding microtubule plus-end tracking proteins (+TIPs) and
      activity-dependent neurotrophic factor (ADNF) active core site
      (NAP)

<400> SEQUENCE: 32

Asn Ala Pro Val Ser Ala Ile Pro Gln
 1               5

<210> SEQ ID NO 33
<211> LENGTH: 9
<212> TYPE: PRT
<213> ORGANISM: Artificial Sequence
<220> FEATURE:
<223> OTHER INFORMATION: synthetic novel peptide core sequence Ac-SKIP
      derived from hybrid microtubule end-binding protein 3
      (EB3)-binding microtubule plus-end tracking proteins (+TIPs) and
      activity-dependent neurotrophic factor (ADNF) active core site
      (NAP)
<220> FEATURE:
<221> NAME/KEY: ACETYLATION
<222> LOCATION: (1)...(1)
<223> OTHER INFORMATION: acetyl-asparagine

<400> SEQUENCE: 33

Asn Ala Pro Val Ser Lys Ile Pro Gln
 1               5

<210> SEQ ID NO 34
<211> LENGTH: 9
<212> TYPE: PRT
<213> ORGANISM: Artificial Sequence
<220> FEATURE:
<223> OTHER INFORMATION: synthetic novel peptide core sequence TRIP
      derived from hybrid microtubule end-binding protein 3
      (EB3)-binding microtubule plus-end tracking proteins (+TIPs) and
      activity-dependent neurotrophic factor (ADNF) active core site
      (NAP)

<400> SEQUENCE: 34

Asn Ala Pro Val Thr Arg Ile Pro Gln
 1               5

<210> SEQ ID NO 35
<211> LENGTH: 8
<212> TYPE: PRT
<213> ORGANISM: Artificial Sequence
<220> FEATURE:
<223> OTHER INFORMATION: synthetic novel peptide core sequence P7A
      derived from hybrid microtubule end-binding protein 3
      (EB3)-binding microtubule plus-end tracking proteins (+TIPs) and
      activity-dependent neurotrophic factor (ADNF) active core site
      (NAP)

<400> SEQUENCE: 35

Asn Ala Pro Val Ser Ile Ala Gln
 1               5

<210> SEQ ID NO 36
<211> LENGTH: 9
<212> TYPE: PRT
<213> ORGANISM: Artificial Sequence
<220> FEATURE:

<223> OTHER INFORMATION: synthetic activity-dependent neurotrophic
      factor (ADNF) active core site (SAL)

<400> SEQUENCE: 36

Ser Ala Leu Leu Arg Ser Ile Pro Ala
1               5

<210> SEQ ID NO 37
<211> LENGTH: 8
<212> TYPE: PRT
<213> ORGANISM: Artificial Sequence
<220> FEATURE:
<223> OTHER INFORMATION: synthetic novel peptide core sequence derived
      from hybrid microtubule end-binding protein 3 (EB3)-binding
      microtubule plus-end tracking proteins (+TIPs) and activity-
      dependent neurotrophic factor (ADNF) active core site (NAP)

<400> SEQUENCE: 37

Asn Ala Pro Val Ser Lys Ile Pro
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic novel peptide core sequence Ac-SKIP
      derived from hybrid microtubule end-binding protein 3
      (EB3)-binding microtubule plus-end tracking proteins (+TIPs) and
      activity-dependent neurotrophic factor (ADNF) active core site
      (NAP)
<220> FEATURE:
<221> NAME/KEY: ACETYLATION
<222> LOCATION: (1)...(1)
<223> OTHER INFORMATION: acetyl-asparagine
<220> FEATURE:
<221> NAME/KEY: AMIDATION
<222> LOCATION: (8)...(8)
<223> OTHER INFORMATION: prolinamide

<400> SEQUENCE: 38

Asn Ala Pro Val Ser Lys Ile Pro Gln
1               5

<210> SEQ ID NO 39
<211> LENGTH: 8
<212> TYPE: PRT
<213> ORGANISM: Artificial Sequence
<220> FEATURE:
<223> OTHER INFORMATION: synthetic novel peptide core sequence derived
      from hybrid microtubule end-binding protein 3 (EB3)-binding
      microtubule plus-end tracking proteins (+TIPs) and activity-
      dependent neurotrophic factor (ADNF) active core site (NAP)

<400> SEQUENCE: 39

Asn Ala Pro Val Ser Gly Ile Pro
1               5

<210> SEQ ID NO 40
<211> LENGTH: 20
<212> TYPE: DNA
<213> ORGANISM: Artificial Sequence
<220> FEATURE:
<223> OTHER INFORMATION: synthetic quantitative real-time PCR mouse
      MAPRE1 primer

<400> SEQUENCE: 40
gcgttgacaa ataattcct                                              20

-continued

```
<210> SEQ ID NO 41
<211> LENGTH: 20
<212> TYPE: DNA
<213> ORGANISM: Artificial Sequence
<220> FEATURE:
<223> OTHER INFORMATION: synthetic quantitative real-time PCR mouse
      MAPRE1 primer

<400> SEQUENCE: 41
tggcagctac aggatcatac                                                    20

<210> SEQ ID NO 42
<211> LENGTH: 24
<212> TYPE: DNA
<213> ORGANISM: Artificial Sequence
<220> FEATURE:
<223> OTHER INFORMATION: synthetic quantitative real-time PCR mouse
      MAPRE2 primer

<400> SEQUENCE: 42
atacagctca acgagcaggt acat                                               24

<210> SEQ ID NO 43
<211> LENGTH: 25
<212> TYPE: DNA
<213> ORGANISM: Artificial Sequence
<220> FEATURE:
<223> OTHER INFORMATION: synthetic quantitative real-time PCR mouse
      MAPRE2 primer

<400> SEQUENCE: 43
cagcagctca atctctctca acttc                                              25

<210> SEQ ID NO 44
<211> LENGTH: 20
<212> TYPE: DNA
<213> ORGANISM: Artificial Sequence
<220> FEATURE:
<223> OTHER INFORMATION: synthetic quantitative real-time PCR mouse
      MAPRE3 primer

<400> SEQUENCE: 44
gctgtgttca cttgaggaag                                                    20

<210> SEQ ID NO 45
<211> LENGTH: 20
<212> TYPE: DNA
<213> ORGANISM: Artificial Sequence
<220> FEATURE:
<223> OTHER INFORMATION: synthetic quantitative real-time PCR mouse
      MAPRE3 primer

<400> SEQUENCE: 45
gaatgatttt gtcaacaccc                                                    20

<210> SEQ ID NO 46
<211> LENGTH: 22
<212> TYPE: DNA
<213> ORGANISM: Artificial Sequence
<220> FEATURE:
<223> OTHER INFORMATION: synthetic quantitative real-time PCR mouse
      HPRT1 endogenous control primer

<400> SEQUENCE: 46
ggatttgaat cacgtttgtg tc                                                 22

<210> SEQ ID NO 47
```

```
<211> LENGTH: 21
<212> TYPE: DNA
<213> ORGANISM: Artificial Sequence
<220> FEATURE:
<223> OTHER INFORMATION: synthetic quantitative real-time PCR mouse
      HPRT1 endogenous control primer

<400> SEQUENCE: 47
caggactcct cgtatttgca g                                          21

<210> SEQ ID NO 48
<211> LENGTH: 20
<212> TYPE: DNA
<213> ORGANISM: Artificial Sequence
<220> FEATURE:
<223> OTHER INFORMATION: synthetic quantitative real-time PCR rat MAPRE1
      primer

<400> SEQUENCE: 48
gaagaaagtg aaattccagg                                            20

<210> SEQ ID NO 49
<211> LENGTH: 20
<212> TYPE: DNA
<213> ORGANISM: Artificial Sequence
<220> FEATURE:
<223> OTHER INFORMATION: synthetic quantitative real-time PCR rat MAPRE1
      primer

<400> SEQUENCE: 49
aggaattatt ttgtcaacgc                                            20

<210> SEQ ID NO 50
<211> LENGTH: 20
<212> TYPE: DNA
<213> ORGANISM: Artificial Sequence
<220> FEATURE:
<223> OTHER INFORMATION: synthetic quantitative real-time PCR rat MAPRE2
      primer

<400> SEQUENCE: 50
gggcgtttcc aagacaacct                                            20

<210> SEQ ID NO 51
<211> LENGTH: 21
<212> TYPE: DNA
<213> ORGANISM: Artificial Sequence
<220> FEATURE:
<223> OTHER INFORMATION: synthetic quantitative real-time PCR rat MAPRE2
      primer

<400> SEQUENCE: 51
cttgtcgagc ctcaacagga t                                          21

<210> SEQ ID NO 52
<211> LENGTH: 20
<212> TYPE: DNA
<213> ORGANISM: Artificial Sequence
<220> FEATURE:
<223> OTHER INFORMATION: synthetic quantitative real-time PCR rat MAPRE3
      primer

<400> SEQUENCE: 52
ggacaaaatc attcccgtag                                            20

<210> SEQ ID NO 53
<211> LENGTH: 20
```

```
<212> TYPE: DNA
<213> ORGANISM: Artificial Sequence
<220> FEATURE:
<223> OTHER INFORMATION: synthetic quantitative real-time PCR rat MAPRE3
      primer

<400> SEQUENCE: 53
ggttgtaatc ctttccatca                                              20

<210> SEQ ID NO 54
<211> LENGTH: 20
<212> TYPE: DNA
<213> ORGANISM: Artificial Sequence
<220> FEATURE:
<223> OTHER INFORMATION: synthetic quantitative real-time PCR rat HPRT1
      endogenous control primer

<400> SEQUENCE: 54
aggccagact tgttggatt                                               20

<210> SEQ ID NO 55
<211> LENGTH: 20
<212> TYPE: DNA
<213> ORGANISM: Artificial Sequence
<220> FEATURE:
<223> OTHER INFORMATION: synthetic quantitative real-time PCR rat HPRT1
      endogenous control primer

<400> SEQUENCE: 55
gcttttccac tttcgctgat                                              20

<210> SEQ ID NO 56
<211> LENGTH: 14
<212> TYPE: PRT
<213> ORGANISM: Artificial Sequence
<220> FEATURE:
<223> OTHER INFORMATION: synthetic NAP sequence bound to sulfolink
      coupling gel for affinity chromatography

<400> SEQUENCE: 56

Cys Lys Lys Lys Gly Gly Asn Ala Pro Val Ser Ile Pro Gln
 1               5                  10

<210> SEQ ID NO 57
<211> LENGTH: 4
<212> TYPE: PRT
<213> ORGANISM: Artificial Sequence
<220> FEATURE:
<223> OTHER INFORMATION: synthetic adenomatous polyposis coli (APC)
      SxIP sequence motif

<400> SEQUENCE: 57

Ser Gln Ile Pro
 1

<210> SEQ ID NO 58
<211> LENGTH: 4
<212> TYPE: PRT
<213> ORGANISM: Artificial Sequence
<220> FEATURE:
<223> OTHER INFORMATION: synthetic stromal interacting molecule 1
      (STIM1) SxIP sequence motif

<400> SEQUENCE: 58

Thr Arg Ile Pro
 1
```

```
<210> SEQ ID NO 59
<211> LENGTH: 4
<212> TYPE: PRT
<213> ORGANISM: Artificial Sequence
<220> FEATURE:
<223> OTHER INFORMATION: synthetic DDA3 (proline/serine-rich coiled
      coil 1 (PSRC1)) SxIP sequence motif

<400> SEQUENCE: 59

Ser Ala Ile Pro
 1

<210> SEQ ID NO 60
<211> LENGTH: 4
<212> TYPE: PRT
<213> ORGANISM: Artificial Sequence
<220> FEATURE:
<223> OTHER INFORMATION: synthetic microtubule-associated protein
      1S/microtubule-associated protein 8 (MAP1S) SxIP
      sequence motif

<400> SEQUENCE: 60

Ser Ser Ile Pro
 1

<210> SEQ ID NO 61
<211> LENGTH: 4
<212> TYPE: PRT
<213> ORGANISM: Artificial Sequence
<220> FEATURE:
<223> OTHER INFORMATION: synthetic microtubule-associated protein 1A
      SxIP sequence motif

<400> SEQUENCE: 61

Ser Pro Ile Pro
 1

<210> SEQ ID NO 62
<211> LENGTH: 8
<212> TYPE: PRT
<213> ORGANISM: Artificial Sequence
<220> FEATURE:
<223> OTHER INFORMATION: synthetic novel peptide core sequence S5A
      derived from hybrid microtubule end-binding protein 3
      (EB3)-binding microtubule plus-end tracking proteins (+TIPs) and
      activity-dependent neurotrophic factor (ADNF) active core site
      (NAP)

<400> SEQUENCE: 62

Asn Ala Pro Val Ala Ile Pro Gln
 1               5
```